US009017679B2

(12) United States Patent
Podack et al.

(10) Patent No.: US 9,017,679 B2
(45) Date of Patent: Apr. 28, 2015

(54) IMMUNOMODULATING TUMOR NECROSIS FACTOR RECEPTOR 25 (TNFR25) AGONISTS, ANTAGONISTS, AND IMMUNOTOXINS

(75) Inventors: Eckhard R. Podack, Coconut Grove, FL (US); Vadim Deyev, Miami, FL (US); Robert Levy, Cooper City, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 13/457,583

(22) Filed: Apr. 27, 2012

(65) Prior Publication Data

US 2012/0321645 A1 Dec. 20, 2012

Related U.S. Application Data

(60) Continuation of application No. 12/534,228, filed on Aug. 3, 2009, now abandoned, which is a division of application No. 11/512,412, filed on Aug. 30, 2006, now abandoned.

(60) Provisional application No. 60/712,084, filed on Aug. 30, 2005.

(51) Int. Cl.
*A61K 39/395* (2006.01)
*C07K 16/28* (2006.01)
*C07K 16/24* (2006.01)
*A61K 39/00* (2006.01)

(52) U.S. Cl.
CPC ............ *C07K 16/2878* (2013.01); *C07K 16/241* (2013.01); *A61K 2039/505* (2013.01); *C07K 2316/95* (2013.01); *C07K 2316/96* (2013.01); *C07K 2317/74* (2013.01)

(58) Field of Classification Search
None
See application file for complete search history.

(56) References Cited

U.S. PATENT DOCUMENTS

| | | |
|---|---|---|
| 4,190,495 A | 2/1980 | Curtiss, III |
| 4,376,110 A | 3/1983 | David et al. |
| 4,518,584 A | 5/1985 | Mark et al. |
| 4,575,013 A | 3/1986 | Bartley |
| 4,654,307 A | 3/1987 | Morgan |
| 4,719,179 A | 1/1988 | Barany |
| 4,737,462 A | 4/1988 | Mark et al. |
| 4,745,051 A | 5/1988 | Smith et al. |
| 4,761,367 A | 8/1988 | Edgell et al. |
| 4,870,009 A | 9/1989 | Evans et al. |
| 4,952,496 A | 8/1990 | Studier et al. |
| 5,093,246 A | 3/1992 | Cech et al. |
| 5,109,124 A | 4/1992 | Ramachandran et al. |
| 5,118,627 A | 6/1992 | Browne |
| 5,122,463 A | 6/1992 | Varshavsky et al. |
| 5,168,062 A | 12/1992 | Stinski |
| 5,169,784 A | 12/1992 | Summers et al. |
| 5,173,403 A | 12/1992 | Tang et al. |
| 5,175,269 A | 12/1992 | Stavrianopoulos |
| 5,176,996 A | 1/1993 | Hogan et al. |
| 5,187,153 A | 2/1993 | Cordell et al. |
| 5,198,343 A | 3/1993 | DeGryse |
| 5,204,254 A | 4/1993 | Schmid et al. |
| 5,212,058 A | 5/1993 | Baker et al. |
| 5,212,286 A | 5/1993 | Lewicki et al. |
| 5,215,907 A | 6/1993 | Tang et al. |
| 5,218,088 A | 6/1993 | Gorenstein et al. |
| 5,220,013 A | 6/1993 | Ponte et al. |
| 5,223,483 A | 6/1993 | Thomas et al. |
| 5,229,279 A | 7/1993 | Peoples et al. |
| 5,242,687 A | 9/1993 | Tykocinski et al. |
| 5,243,041 A | 9/1993 | Fernandez-Pol |
| 5,244,805 A | 9/1993 | Miller |
| 5,256,775 A | 10/1993 | Froehler |
| 5,264,564 A | 11/1993 | Matteucci |
| 5,266,317 A | 11/1993 | Tomalski et al. |
| 5,278,050 A | 1/1994 | Summers |
| 5,362,718 A | 11/1994 | Skotnicki et al. |
| 5,434,065 A | 7/1995 | Mahan et al. |
| 5,510,099 A | 4/1996 | Short et al. |
| 5,567,440 A | 10/1996 | Hubbell et al. |
| 5,656,481 A | 8/1997 | Baetge et al. |
| 5,693,622 A | 12/1997 | Wolff et al. |
| 5,700,657 A | 12/1997 | Beaudry et al. |

(Continued)

FOREIGN PATENT DOCUMENTS

| | | |
|---|---|---|
| CA | 2451138 | 1/2003 |
| CN | 101253199 | 8/2008 |

(Continued)

OTHER PUBLICATIONS

Deyev et al. TNFR25 expression on CD4(+)CD25(+) T cells: Down modulation of regulatory activity. Blood, (Nov. 16, 2006) vol. 108, No. 11, Part 1, pp. 903A.*
Watts, Annu. Rev. Immunol. 2005. 23:23-68.*
Pulendran, Immunological Reviews 2004 vol. 199: 227-250.*
Wen, T. et al: "4-1BB Ligand-mediated costimulation of Human T Cells induces CD4 and CD8 T cell expansion, cytokine production, and the development of cytolytic effector function," The Journal of Immunology, 2002, vol. 168:4897-4906.
Shuford, W.W. et al: "4-1BB costimulatory signals preferentially induce CD8+ T cell proliferation and lead to the amplication in vivo of cytotoxic T cell responses," J. Exp. Med., 1997, vol. 186:47-55.
Miller, R.E. et al: "4-1BB-specific monoclonal antibody promotes the generation of tumor-specific immune responses by direct activation of CD8 T cells in a CD40-dependent manner," The Journal of Immunology, 2002, vol. 169:1792-1800.

(Continued)

*Primary Examiner* — Zachary Skelding
(74) *Attorney, Agent, or Firm* — Fish & Richardson P.C.

(57) ABSTRACT

Compositions and methods utilizing immunomodulating agents can either stimulate or indirectly augment the immune system or have an immunosuppressive effect. TNFR25 agonists disclosed herein have an anti-inflammatory and healing effect. They can be used to treat disease caused by asthma and chronic inflammation such as inflammatory bowel diseases including ulcerative colitis and Crohn's Disease. TNFR25 antagonists disclosed herein are capable of inhibiting CD8 T cell-mediated cellular immune responses and can for example, mitigate organ or tissue rejection following a tissue transplantation.

15 Claims, 26 Drawing Sheets

(56) References Cited

U.S. PATENT DOCUMENTS

| | | | |
|---|---|---|---|
| 5,714,323 | A | 2/1998 | Ohshima et al. |
| 5,773,246 | A | 6/1998 | Keene et al. |
| 5,859,208 | A | 1/1999 | Fiddes et al. |
| 5,955,056 | A | 9/1999 | Short et al. |
| 5,985,644 | A | 11/1999 | Roseman et al. |
| 6,254,874 | B1 | 7/2001 | Mekalanos et al. |
| 6,534,061 | B1 | 3/2003 | Goddard et al. |
| 6,713,061 | B1 | 3/2004 | Yu et al. |
| 7,226,617 | B2 | 6/2007 | Ding et al. |
| 7,300,774 | B1 | 11/2007 | Kornbluth |
| 7,357,927 | B2 | 4/2008 | Yu et al. |
| 7,385,032 | B2 | 6/2008 | Tschopp |
| 7,723,454 | B2 | 5/2010 | Keller et al. |
| 7,736,657 | B2 | 6/2010 | Gaide et al. |
| 2002/0009773 | A1 | 1/2002 | Yu |
| 2002/0015703 | A1 | 2/2002 | Rennert |
| 2002/0111325 | A1 | 8/2002 | Li et al. |
| 2002/0150534 | A1 | 10/2002 | Yu et al. |
| 2003/0092044 | A1 | 5/2003 | Goddard et al. |
| 2003/0129189 | A1 | 7/2003 | Yu et al. |
| 2003/0170203 | A1 | 9/2003 | Yu |
| 2004/0013655 | A1 | 1/2004 | Shiozawa |
| 2004/0156847 | A1 | 8/2004 | Miura et al. |
| 2005/0123536 | A1 | 6/2005 | Law et al. |
| 2005/0158831 | A1 | 7/2005 | Kornbluth |
| 2005/0282223 | A1 | 12/2005 | Tittle et al. |
| 2006/0233751 | A1 | 10/2006 | Bluestone et al. |
| 2007/0128184 | A1 | 6/2007 | Podack et al. |
| 2008/0003221 | A1 | 1/2008 | Podack |
| 2008/0233119 | A2 | 9/2008 | Podack |
| 2009/0317388 | A1 | 12/2009 | Burkly et al. |
| 2011/0243951 | A1 | 10/2011 | Podack et al. |
| 2012/0029472 | A1 | 2/2012 | Podack et al. |
| 2012/0135011 | A1* | 5/2012 | Podack et al. ............ 424/174.1 |
| 2012/0263718 | A1 | 10/2012 | Siegel et al. |
| 2012/0328559 | A1 | 12/2012 | Podack |
| 2013/0142793 | A1 | 6/2013 | Ledbetter et al. |
| 2014/0193410 | A1 | 7/2014 | Podack et al. |

FOREIGN PATENT DOCUMENTS

| | | |
|---|---|---|
| EP | 1405645 | 4/2004 |
| EP | 1246925 | 5/2008 |
| JP | 2009-505678 | 2/2009 |
| WO | WO89/07142 | 8/1989 |
| WO | WO91/13160 | 9/1991 |
| WO | WO93/01286 | 1/1993 |
| WO | WO94/09010 | 4/1994 |
| WO | WO95/16691 | 6/1995 |
| WO | WO95/30762 | 11/1995 |
| WO | WO96/01899 | 1/1996 |
| WO | WO96/39154 | 12/1996 |
| WO | WO96/41807 | 12/1996 |
| WO | WO97/03211 | 1/1997 |
| WO | WO98/02441 | 1/1998 |
| WO | WO99/15530 | 4/1999 |
| WO | WO99/23105 | 5/1999 |
| WO | WO99/43839 | 9/1999 |
| WO | WO00/64465 | 11/2000 |
| WO | WO01/14387 | 3/2001 |
| WO | WO01/35995 | 5/2001 |
| WO | WO01/85207 | 11/2001 |
| WO | WO02/11767 | 2/2002 |
| WO | WO02/094192 | 11/2002 |
| WO | WO02/100345 | 12/2002 |
| WO | WO03/000286 | 1/2003 |
| WO | WO03/039491 | 5/2003 |
| WO | WO03/043583 | 5/2003 |
| WO | WO03/068977 | 8/2003 |
| WO | WO2005/018571 | 3/2005 |
| WO | WO2006/127900 | 11/2006 |
| WO | WO2007/027751 | 3/2007 |
| WO | WO2007/041317 | 4/2007 |
| WO | WO2011/017303 | 2/2011 |
| WO | WO2012/170072 | 12/2012 |

OTHER PUBLICATIONS

Papadakis, K.A. et al: "TL1A synergizes with IL-12 and IL-18 to enhance IFN-gamma production in human T cells and NK cells," The Journal of Immunology, 2004, vol. 172:7002-7007.

Sanchez-Fueyo, A. et al.: "CD4+CD25+ regulatory T cells in transplantation tolerance," Immunologia, vol. 23, 2004, No. 2:231-238.

Bull, M. J. et al: "The death receptor 3-TNF-like protein 1A pathway drives adverse bone pathology in inflammatory arthritis," J. Exp. Med., vol. 205, No. 11:2457-2464, 2008.

Al-Lamki, Rafia S. et al.: "TL1A both promotes and protects from renal inflammation and injury," J Am Soc Nephrol, 2008, vol. 19:953-960.

Jin, S. et al.: "TL1A/TNFSF15 directly induces proinflammatory cytokines, including TNFalpha, from CD3+CD161+T cells to exacerbate gut inflammation," Society for Mucosal Immunology, 2012, pp. 1:14.

Zhang, Jun et al.: "Role of TL1A in the pathogenesis of rheumatoid arthritis," The Journal of Immunology, 2009, vol. 183:5350-5357.

Pappu, Bhanu P. et al.: "TL1A-DR3 interaction regulates Th17 cell function and Th17-mediated autoimmune disease," J. Exp. Med, 2008, vol. 205, No. 5:1049-1062.

"TNFRSF25" entry in National Library of Medicine—Medical Subject Headings, "Receptors, Tumor Necrosis Factor, Member 25," National Library of Medicine [online], 2013 [retrieved on May 3, 2013]. Retrieved from the Internet: < URL: http://www.nlm.nih.gov/cgi/mesh/2013/MB_cgi?mode=&index=23859&field=all&HM=&II=&PA=&form=&input=>, 3 pages.

Akbari et al., "Essential role of NKT cells producing IL-4 and IL-13 in the development of allergen-induced airway hyperreactivity," *Nat Med.*, 9(5):582-588, Mar. 31, 2003.

Al-Lamki et al., "Expression of silencer of death domains and death-receptor-3 in normal kidney and in rejecting renal transplants," *Am J Pathol.*, 163(2):401-411, Aug. 2003.

Allan et al., "CD4+ T-regulatory cells: toward therapy for human diseases," *Immunol Rev.*, 223:391-421, Jun. 2008.

Bamias et al., "Expression, localization, and functional activity of TL1A, a novel Th1-polarizing cytokine in inflammatory bowel disease,", *J Immunol.*, 171(9):4868-4874, Nov. 1, 2003.

Benghiat et al., "Critical influence natural regulatory CD25+ T cells on the fate of allografts in the absence of immunosuppression," *Transplantation*, 79(6):648-654, Mar. 27, 2005.

Berg et al., "ACRP30/adiponectin: an adipokine regulating glucose and lipid metabolism," *Trends Endocrinol Metab.*, 13(2):84-89, Mar. 2002.

Bodmer et al., "TRAMP, a novel apoptosis-mediating receptor with sequence homology to tumor necrosis factor receptor 1 and Fas(Apo-1/CD95)," *Immunity.*, 6(1):79-88, Jan. 1997.

Branch, "A good antisense molecule is hard to find," *Trends Biochem Sci.*, 23(2):45-50, Feb. 1998.

Chen, "TGF-Beta1 Regulation of chemokine receptors in rat microglia and human macrophages," University of Florida, 2001, 119 pages [Dissertation].

Chew et al., "A novel secreted splice variant of vascular endothelial cell growth inhibitor," *FASEB J.*, 16(7):742-744. Epub Mar. 26, 2002.

Chinnaiyan et al., "Signal transduction by DR3, a death domain-containing receptor related to TNFR-1 and CD95," *Science.*, 274(5289):990-992, Nov. 8, 1996.

Cobrin and Abreu, "Defects in mucosal immunity leading to Crohn's disease," *Immunol Rev.*, 206:277-295, Aug. 2005.

Cui, "Requirement for Valpha14 NKT cells in IL-12-mediated rejection of tumors," *Science.*, 278(5343):1623-1626, Nov. 28, 1997.

Del Prete et al., CD30-mediated signaling promotes the development of human T helper type 2-like T cells, *J Exp Med.*, 182(6):1655-1661, Dec. 1, 1995.

Fang, "Death receptor 3 (TNFR-SF25) delivers a late-acting costimulatory signal for Th2 cytokine production during the development of allergic asthma" University of Miami, Dec. 2004, 153 pages [Dissertation].

(56) References Cited

OTHER PUBLICATIONS

Grünig et al., "Requirement for IL-13 independently of IL-4 in experimental asthma," *Science.*, 282(5397):2261-2263, Dec. 18, 1998.
Harlin et al., "TCR-independent CD30 signaling selectively induces IL-13 production via a TNF receptor-associated factor/p38 mitogen-activated protein kinase-dependent mechanism," *J Immunol.*, 169(5):2451-2459, Sep. 1, 2002.
Huang, "Structural chemistry and therapeutic intervention of protein-protein interactions in immune response, human immunodeficiency virus entry, and apoptosis," *Pharmacol Ther.*, 86(3):201-215, Jun. 2000.
Khan et al., "Cloning, expression, and functional characterization of TL1A-Ig;" *J Immunol.*, 190(4):1540-1550, Epub Jan. 14, 2013.
Kitson et al., "A death-domain-containing receptor that mediates apoptosis," *Nature*, 384(6607):372-375, Nov. 28, 1996.
Leonard et al., "Allergen-induced CD30 expression on T cells of atopic asthmatics," *Clin Exp Allergy.*, 27(7):780-786, Jul. 1997.
Li et al., "Effects of Th2 cytokines on chemokine expression in the lung: IL-13 potently induces eotaxin expression by airway epithelial cells," *J Immunol.*, 162(5):2477-2487, Mar. 1, 1999.
Marsters et al., "Apo-3, a new member of the tumor necrosis factor receptor family, contains a death domain and activates apoptosis and NF-kappa B," *Curr Biol.*, 6(12):1669-1676, Dec. 1, 1996.
Mattes et al., "IL-13 induces airways hyperreactivity independently of the IL-4R alpha chain in the allergic lung," *J Immunol.*, 167(3):1683-1692, Aug. 1, 2001.
Meloni et al., "Peripheral CD4+ CD25+ Treg cell expansion in lung transplant recipients is not affected by calcineurin inhibitors," *Int Immunopharmacol.*, 6(13-14):2002-10. Epub Aug. 17, 2006.
Meloni et al., "Regulatory CD4+CD25+ T cells in the peripheral blood of lung transplant recipients: correlation with transplant outcome," *Transplantation*, 77(5):762-766, Mar. 15, 2004.
Migone et al., "TL1A is a TNF-like ligand for DR3 and TR6/DcR3 and functions as a T cell costimulator," *Immunity.*, 16(3):479-492, Mar. 2002.
Nam et al., "CD30 deficiency diminishes airway eosinophillia in a mouse model of pulmonary inflammation," *FASEB J.*, 17(7): C14, Abstract 30.24, May 6-10, 2003, Denver, Colorado.
Papadakis et al., "Dominant role for TL1A/DR3 pathway in IL-12 plus IL-18-induced IFN-gamma production by peripheral blood and mucosal CCR9+ T lymphocytes," *J Immunol.*, 174(8):4985-4990, Apr. 15, 2005.
Prehn et al., "Potential role for TL1A, the new TNF-family member and potent costimulator of IFN-gamma, in mucosal inflammation," *Clin Immunol.*, Jul. 2004, 112(1):66-77.
Purello-D'Ambrosio et al., "Effect of fluticasone propionate on soluble CD30 release in patients with severe allergic asthma," *J Investig Allergol Clin Immunol.*, 10(5):283-285, Sep.-Oct. 2000.
R&D Systems, "Adiponectin/Acrp30: Products," R&D Systems [online], as appeared on Jan. 26, 2013 [retrieved on Sep. 9, 2014]. Retrieved from the Internet: < URL: http://web.archive.org/web/20130126225534/http://rndsystems.com/product_results.aspx?m=1034>, 2 pages.
Schreiber et al. "T cell costimulation by TNFR superfamily (TNFRSF)4 and TNFRSF25 in the context of vaccination," *J Immunol.*, 189(7):3311-3318, Epub Sep. 5, 2012.
Schreiber et al., "Therapeutic Treg expansion in mice by TNFRSF25 prevents allergic lung inflammation," *J Clinc Invest.*, 120(10):3629-36240, Oct. 2010.
Screaton et al., "LARD: a new lymphoid-specific death domain containing receptor regulated by alternative pre-mRNA splicing," *Proc Natl Acad Sci U S A.*, 94(9):4615-4619, Apr. 29, 1997.
Takedatsu et al., "TL1A (TNFSF15) regulates the development of chronic colitis by modulating both T-helper 1 and T-helper 17 activation," *Gastroenterology*, 135(2):552-567, Epub May 7, 2008.
Tan et al., "Characterization of a novel TNF-like ligand and recently described TNF ligand and TNF receptor superfamily genes and their constitutive and inducible expression in hematopoietic and non-hematopoietic cells," *Gene*, 204(1-2):35-46, Dec. 19, 1997.
Wang et al., "DR3 regulates negative selection during thymocyte development," *Mol Cell Biol.*, 21(10):3451-3461, May 2001.
Wen et al., "TL1A-induced NF-kappaB activation and c-IAP2 production prevent DR3-mediated apoptosis in TF-1 cells," *J Biol Chem.* 278(40):39251-39258, Epub Jul. 25, 2003.
Wills-Karp et al., "Interleukin-13: central mediator of allergic asthma," *Science*, 282(5397):2258-2261, Dec. 18, 1998.
Wolf et al., "Tregs expanded in vivo by TNFRSF25 agonists promote cardiac allograft survival," *Transplantation.*, 94(6):569-574, Sep. 27, 2012.
International Preliminary Report on Patentability for PCT/US2006/033828, issued Mar. 4, 2008, 10 pages.
International Search Report and Written Opinion for PCT/US2006/033828, mailed Jun. 20, 2007, 15 pages.

* cited by examiner

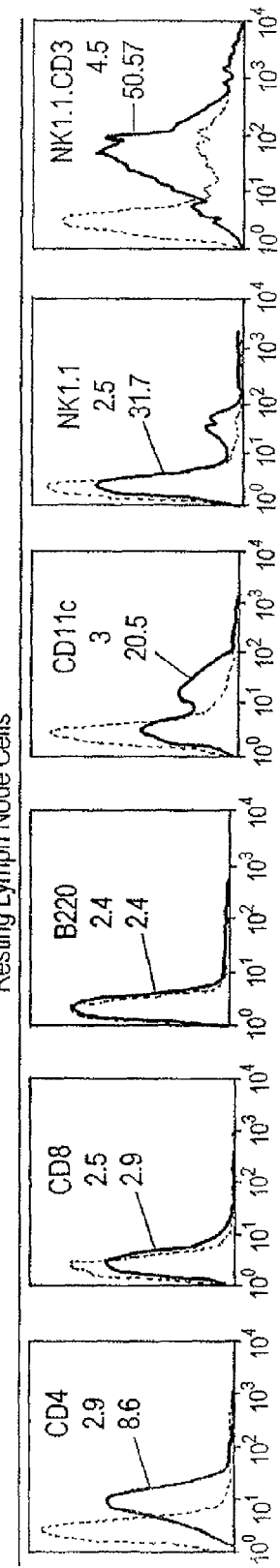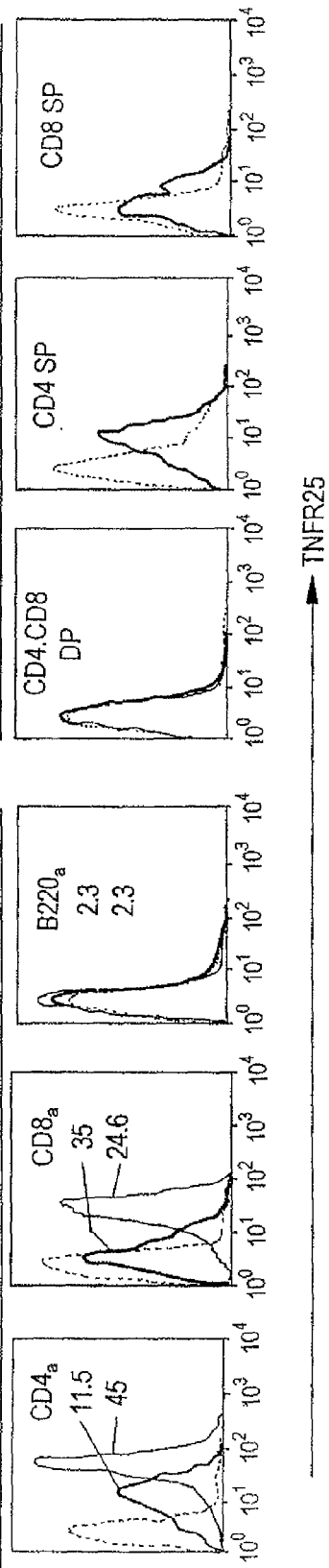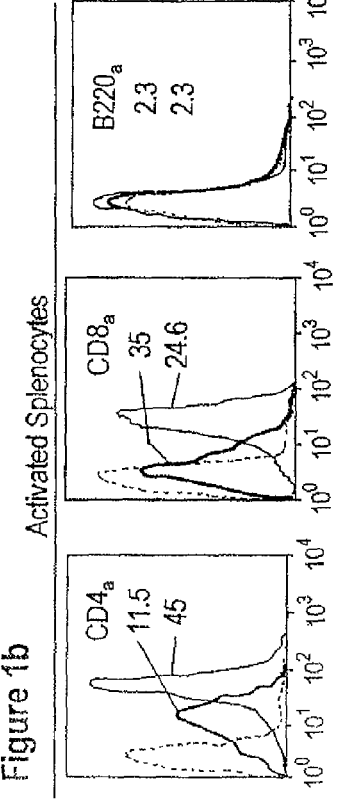
Figure 1a
Figure 1b
Figure 1c

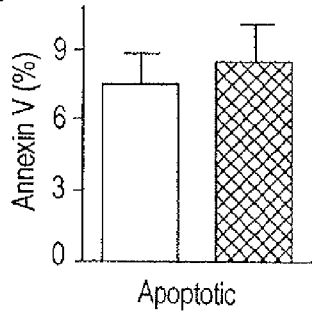
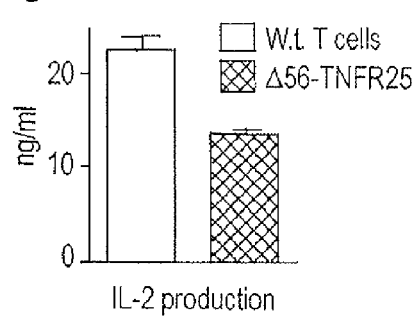
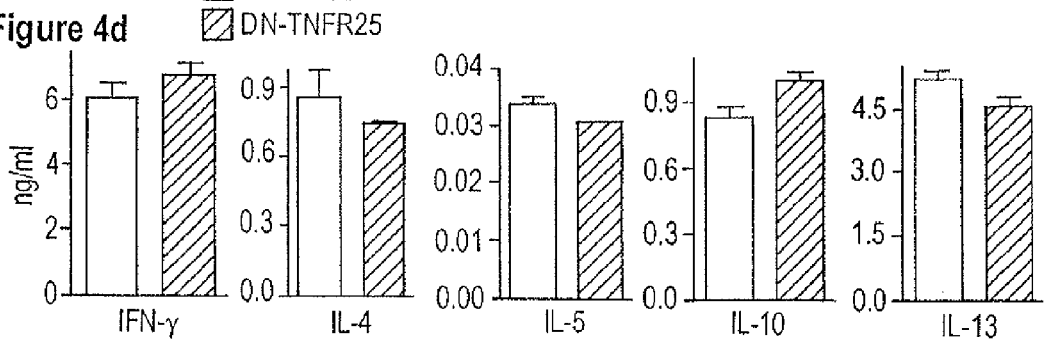
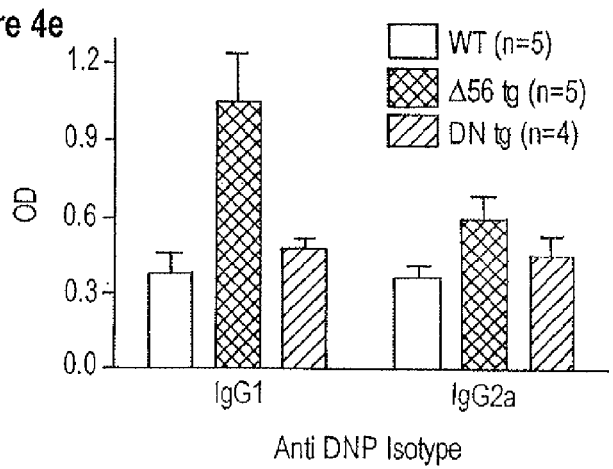

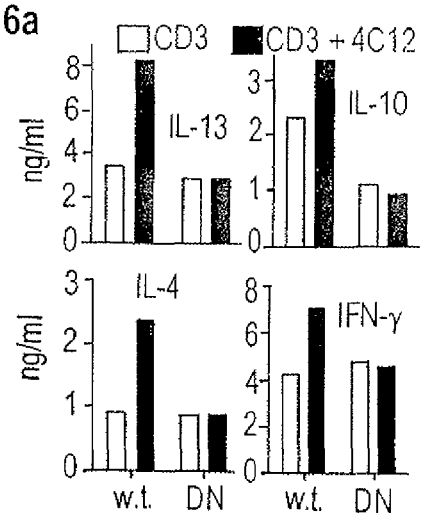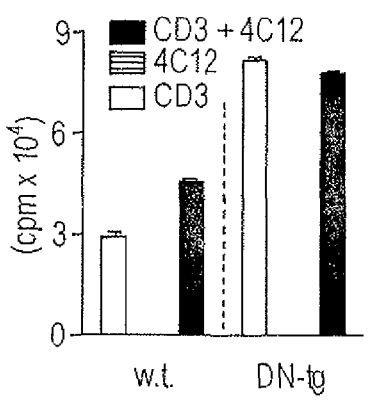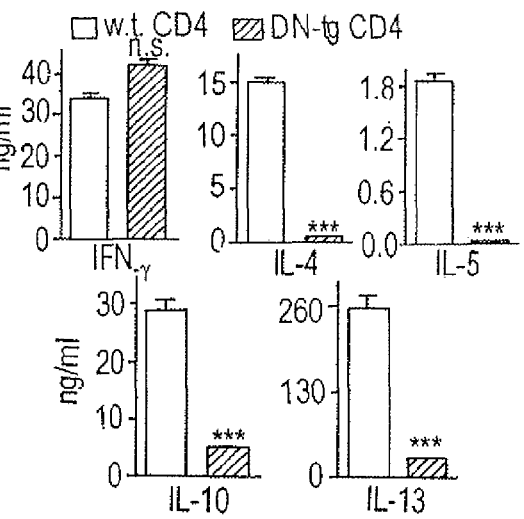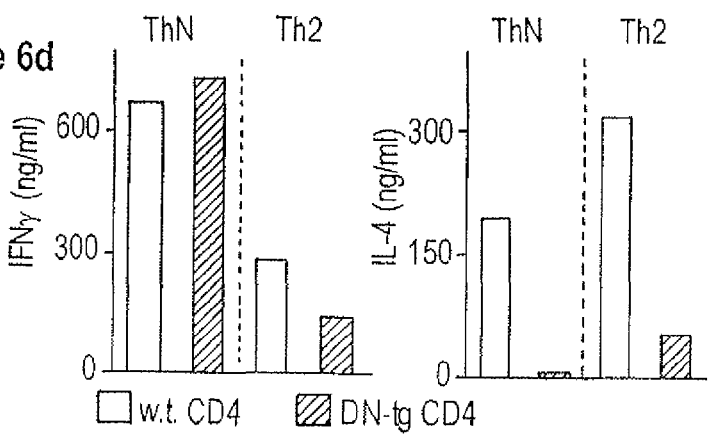

OVa-specific IgE

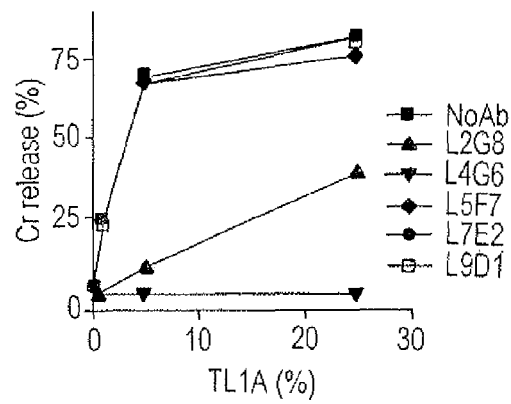
Figure 7d
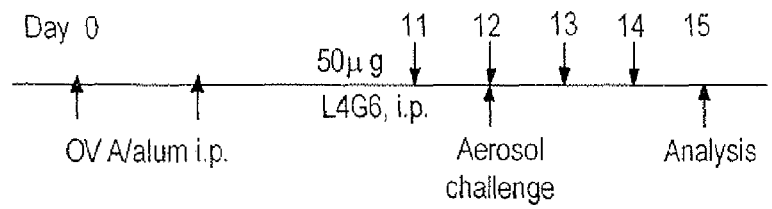
Figure 7e
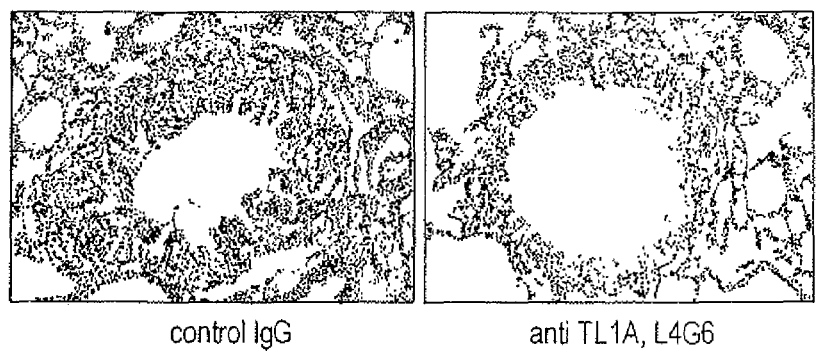
Figure 7f
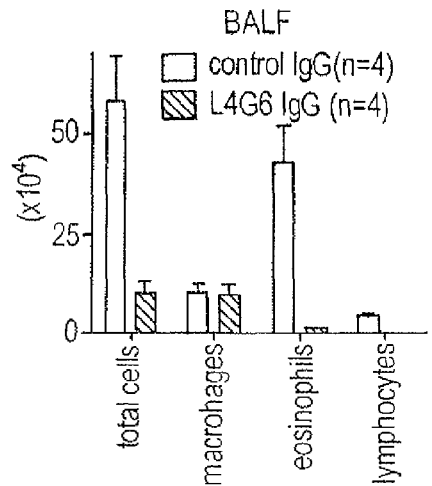
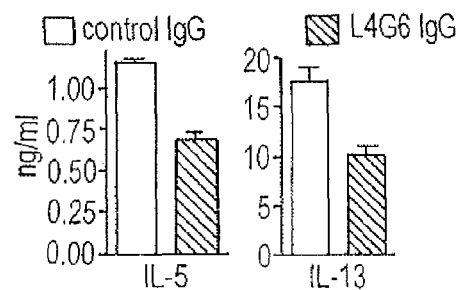
Figure 7g

Figure 17

SEQ ID NO: 1 - Mouse TNFER25 cDNA; NM_033042

```
   1 gggagttgtt ctggatggcg cggggcgggg cgggcagcag ctactctagt ctaggaacat
  61 aggggctgag ctggttgggg aagccccggg ttacgcgacc gaccagagcc gcactcacaa
 121 gggcccaggc ggtacacacc gcaatggagg cacggctgct gcgggctgc gtggtggagc
 181 ctctgttcct accactgctg ctgctgctgc tgctgctgct gctgcttggt ggccagggcc
 241 agggcggcat gtctggcagg tgtgactgtg ccagtgagtc ccagaagagg tatgcccgt
 301 tttgttcag gggctgccca aagggacact acatgaaggc ccctgcgca gaaccctgtg
 361 gcaactccac ctgccttccc tgtccctcgg acacttctt gaccagagac aaccacttta
 421 agactgactg taccgctgc caagtctgtg atgaagagc ccttcaagtg accettgaga
 481 actgctcggc aaagtcggac accactgtg gctgccagtc aggctggtgt gttgactgct
 541 ccaccgtgcc atgtgggaaa agctcacctt tctcttgtgt cccatgcggg gctacgacac
 601 cagtccatga ggctccaacc cccggccct gcctgctgg cttctatata cgtggcaatg
 661 actgcacgtc ctgccccacg ggcttcagca gcgtttgccc taaggcttgc actgctgtct
 721 gtggctggaa gcagatgttt tgggtccagg tgcttctagg agtcgcgttc cttttgggg
 781 ctatcctgat ctgtgcatat tgtcgatggc agccttgtaa ggccgtggtc actgcagaca
 841 cagctgggac ggagcccctg gcctcaccac agactgccca tctctcagcc tcagacagcg
 901 cccacaccct cttggcacct ccaagcagta ctgggaaaat ctgtaccact gtccagttgg
 961 taggcaacaa ctggaccct ggcttatccc agactcagga ggtggtctgc ggacaggcct
1021 cacaaccctg ggatcagctg ccaaacagaa ctcttggaac tcctctggca tctccgctct
1081 cgccagcgcc cctgcgggc tctccggctg ctgtgctcca gcctggcccg cagctctacg
1141 atgtgatgga tgcggtccca gcacgaaggt ggaaggagtt cgtgcgcacg ctgggctgc
1201 gggaagcgga aattgaagcc gtggaggtgg aaatctgccg cttccgagac cagcagtatg
1261 agatgctcaa gcgctggcgt cagcagcagc ctgcaggct cggtgccatc tatgcggctc
1321 tggagcgcaa gggtctggaa ggctgtgccg aggacctgcg cagccgcctg cagcgtggcc
1381 cgtgatggaa ggtccatcat ccactttgac accctagtga cccttgaagg agccttaagt
1441 attgttactt atgcgtgtag acatttatg tcaattacta acccctgcc gtggtcctgc
1501 gtagcagggc tgctgcctc acttttgctt atctgcagca cggagctcct gctaagggaa
1561 gcgtcatgga gaaataccag aaggggccaa gtgattggtt gctcagctgt taattagccc
1621 gagtttggac ttggtattaa atttcataag aaaagcagct gcttg
```

SEQ ID NO: 2 - Human TNFER25 cDNA; NM_148965

```
   1 cgggccctgc gggcgcgggg ctgaaggcgg aaccacgacg ggcagagagc acggagccgg
  61 gaagcccctg ggcgccgtc ggagggctat ggagcagcgg ccgcggggct gcgcggcggt
 121 ggcggcggcg ctcctcctgg tgctgctggg ggccgggcc cagggcggca ctcgtagccc
 181 caggtgtgac tgtgccggtg acttccacaa gaagattggt ctgttttgtt gcagaggctg
 241 cccagcgggg cactacctga aggccccttg cacggagccc tgcggcaact ccacctgcct
 301 tgtgtgtccc caagacacct tcttggcctg ggagaaccac cataattctg aatgtgcccg
 361 ctgccaggcc tgtgatgagc aggcctccca ggtggcgctg gagaactgtt cagcagtggc
 421 cgacacccgc tgtggctgta agccaggctg gttcgtggag tgccaggtca gccaatgtgt
 481 cagcagttca cccttctact gccaaccatg cctagactgc ggggcctgc acgccacac
 541 acggctactc tgttcccgca gagatactga ctgtgggacc tgcctgcctg gcttctatga
 601 acatggcgat ggctgcgtgt cctgccccac gccaccccg tccttgcag gagcaccctg
 661 gggagctgtc cagagcgctg tgccgctgtc tgtggctgga ggcagagtag gtgtgttctg
 721 ggtccaggtg ctcctggctg gccttgtggt cccctcctg cttggggcca cctgacctg
 781 cacataccgc cactgctggc ctcacaagcc cctggttact gcagatgaag ctgggatgga
 841 ggctctgacc ccaccacgg ccaccatct gtcaccttg gacagcgcc acaccettct
 901 agcacctcct gacagcagtg agaagatctg caccgtccag ttggtgggta acagctggac
 961 ccctggctac cccgagaccc aggaggcgct ctgccgcag gtgacatggt cctggaccca
1021 gttgcccagc agagctcttg gccccgctgc tgcgcccaca ctctcgccag agtccccagc
1081 cggctcgcca gccatgatgc tgcagccggg cccgcagctc tacgacgtga tggacgcggt
1141 cccagcgcgg cgctggaagg agttcgtgcg cacgctgggg ctgcgcgagg cagagatcga
1201 agccgtggag gtggagatcg gccgcttcag agaccagcag tacgagatgc tcaagcgctg
1261 gcgccagcag cagcccgcgg gcctcggagc cgtttacgcg ccctggagc gcatggggct
```

Figure 17 Continue

```
1321  ggacggctgc  gtggaagact  tgcgcagccg  cctgcagcgc  ggcccgtgac  acggcgccca
1381  cttgccacct  aggcgctctg  gtggcccttg  cagaagccct  aagtacgtt   acttatgcgt
1441  gtagacattt  tatgtcactt  attaagccgc  tggcacggcc  ctgcgtagca  gcaccagccg
1501  gccccacccc  tgctcgcccc  tatcgctcca  gccaaggcga  agaagcacga  acgaatgtcg
1561  agaggggtg   aagacatttc  tcaacttctc  ggccggagtt  tggctgagat  cgcggtatta
1621  aatctgtgaa  agaaaacaaa  acaaaacaaa  aaaaaaaaa   aaaaa
```

SEQ ID NO: 3 - Mouse TL1A cDNA; AF520786

```
  1  atggcagagg  agctggggtt  gggcttcgga  gaagcagtcc  cagtggaagt  gctgccggaa
 61  ggctgtagac  acaggccaga  ggccagggcc  gggctagctg  ccaggagcaa  agcctgcctg
121  gctctcacct  gctgcctgtt  gtcatttccc  atcctcgcag  gacttagcac  cctcctaatg
181  gctggccagc  tccgggtccc  cggaaaagac  tgtatgcttc  gggccataac  agaagagaga
241  tctgagcctt  caccacagca  agttttactca cctcccagag  gcaagccgag  agcacacctg
301  acaattaaga  aacaaacccc  agcaccacat  ctgaaaaatc  agctctctgc  tctacactgg
361  gaacatgacc  tagggatggc  cttcaccaag  aacgggatga  agtacatcaa  caaatccctg
421  gtgatcccag  agtcaggaga  ctatttcatc  tactcccaga  tcacattccg  agggaccaca
481  tctgtgtgtg  gtgacatcag  tcggggagga  cgaccaaaca  agccagactc  catcactgtg
541  gtcatcacca  aggtagcaga  cagctaccct  gagcctgccc  gcctactaac  agggtccaag
601  tctgtgtgtg  aaataagcaa  caactggttc  cagtccctct  accttggggc  catgttctcc
661  ttggaagaag  gggacagact  aatggtaaac  gtcagtgaca  tctccttggt  ggattacaca
721  aaagaagata  aactttcttt  tggagctttc  ttgctataa
```

SEQ ID NO: 4 - Mouse DN TNFR25 cDNA

```
atggagg     cacggctgct  gcggggctgc  gtggtggagc
ctctgttcct  accactgctg  ctgctgctgc  tgctgctgct  gctgcttggt  ggccagggcc
agggcggcat  gtctggcagg  tgtgactgtg  ccagtgagtc  ccagaagagg  tatgggccgt
tttgttgcag  gggctgccca  aagggacact  acatgaaggc  ccctgcgca   gaacctgtg
gcaactccac  ctgccttccc  tgtccctcgg  acaccttctt  gaccagagac  aaccacttta
agactgactg  tacccgctgc  caagtctgtg  atgaagaggc  ccttcaagtg  acccttgaga
actgctcggc  aaagtcggac  acccactgtg  gctgccagtc  aggctggtgt  gttgactgct
ccaccgtgcc  atgtgggaaa  agctcacctt  tctcttgtgt  cccatgcggg  gctacgacac
cagtccatga  ggctccaacc  ccccggccct  gcctgcctgg  cttctatata  cgtggcaatg
actgcacgtc  ctgccccacg  ggcttcagca  gcgtttgccc  taaggcttgc  actgctgtct
gtggctggaa  gcagatgttt  tgggtccagg  tgcttctagg  agtcgcgttc  cttttttggg
ctatcctgat  ctgtgcatat
```

SEQ ID NO: 5 - Human DN TNFR25 cDNA (extracellular + transmembrance only)

```
atggagcagcgg  ccgcggggct  gcgcggcggt
ggcggcggcg   ctcctcctgg   tgctgctggg  ggcccgggcc  cagggcggca  ctcgtagccc
caggtgtgac   tgtgccggtg   acttccacaa  gaagattggt  ctgttttgtt  gcagaggctg
cccagcgggg   cactacctga   aggcccttg   cacggagccc  tgcggcaact  ccacctgcct
tgtgtgtccc   caagacacct   tcttggcctg  ggagaaccac  ataattctg   aatgtgcccg
ctgccaggcc   tgtgatgagc   aggcctccca  ggtggcgctg  agaactgtt   cagcagtggc
cgacacccgc   tgtggctgta   agccaggctg  gtttgtgag   tgccaggtca  gccaatgtgt
cagcagttca   cccttctact   gccaaccatg  cctagactgc  ggggccctgc  acggccacac
acggctactc   tgttcccgca   gagatactga  ctgtgggacc  tgcctgcctg  gcttctatga
acatggcgat   ggctgcgtgt   cctgccccac  gccaccccg   tcccttgcag  gagcacctg
gggagctgtc   cagagcgctg   tgccgctgtc  tgtggctgga  ggcagagtag  gtgtgttctg
ggtccaggtc   ctcctggctg   gccttgtggt  ccctctcctg  cttggggcca  ccctgaccta
caca
```

Figure 17 Continue

SEQ ID NO: 6 - Human DN TNFR25 cDNA (extracellular only)

```
       at ggagcagcgg ccgcggggct gcgcggcggt
ggcggcggcg ctcctcctgg tgctgctggg ggcccgggcc cagggcggca ctcgtagccc
caggtgtgac tgtgccggtg acttccacaa gaagattggt ctgttttgtt gcagaggctg
cccagcgggg cactacctga aggccccttg cacggagccc tgcggcaact ccacctgcct
tgtgtgtccc caagacacct tcttggcctg ggagaaccac cataattctg aatgtgcccg
ctgccaggcc tgtgatgagc aggcctccca ggtggcgctg gagaactgtt cagcagtggc
cgacacccgc tgtggctgta agccaggctg gtttgtggag tgccaggtca gccaatgtgt
cagcagttca cccttctact gccaaccatg cctagactgc ggggccctgc accgccacac
acggctactc tgttcccgca gagatactga ctgtgggacc tgcctgcctg gcttctatga
acatcggcgat ggctgcgtgt cctgccccac gccaccccg tcccttgcag agcaccctg
gggagctgtc cagagcgctg tgccgctgtc tgtggctgga ggcagagtag gtgtgttctg
g
```

SEQ ID NO: 7 - Human TL1A; cDNA; AF520785

```
   1 gagagcgaaa agggaaggag gagactgagt gattaagtca cccactgtga agagctggtc
  61 ttctatttaa tgggggctct ctctgcccag gagtcagagg tgcctccagg agcagcagga
 121 gcatggccga ggatctggga ctgagctttg gggaaacagc cagtgtggaa atgctgccag
 181 agcacggcag ctgcaggccc aaggccagga gcagcagcgc acgctgggct ctcacctgct
 241 gcctggtgtt gctccccttc cttgcaggac tcaccacata cctgcttgtc agccagctcc
 301 gggcccaggg agaggcctgt gtgcagttcc aggctctaaa aggacaggag tttgcacctt
 361 cacatcagca agtttatgca cctcttagag cagacggaga taagccaagg cacacctga
 421 cagttgtgag acaaactccc acacagcact ttaaaaatca gttcccagct ctgcactggg
 481 aacatgaact aggcctggcc ttcaccaaga accgaatgaa ctataccaac aaattcctgc
 541 tgatcccaga gtcgggagac tacttcattt actcccaggt cacattccgt gggatgacct
 601 ctgagtgcag tgaaatcaga caagcaggcc gaccaaacaa gccagactcc atcactgtgg
 661 tcatcaccaa ggtaacagac agctaccctg agccaaccca gctcctcatg gggaccaagt
 721 ctgtatgcga agtaggtagc aactggttcc agcccatcta cctcggagcc atgttctctc
 781 tgcaagaagg ggacaagcta atggtgaacg tcagtgacat ctctttggtg gattacacaa
 841 aagaagataa aaccttcttt ggagccttct actatagga ggagagcaaa tatcattata
 901 tgaaagtcct ctgccacga gttcctaatt ttcttgttc aaatgtaatt ataaccaggg
 961 gttttcttgg ggccgggagt agggggcatt ccacagggac aacggtttag ctatgaaatt
1021 tggggcccaa aatttcacac ttcatgtgcc ttactgatga gagtactaac tggaaaaggc
1081 tgaagagagc aaatatatta ttaagatggg ttggaggatt ggcgagtttc taaatattaa
1141 gacactgatc actaaatgaa tggatgatct actcgggtca ggattgaaag agaaatattt
1201 caacacctcc ctgctataca atggtcacca gtggtccagt tattgttcaa tttgatcata
1261 aatttgcttc aattcaggag ctttgaagga agtccaagga agctctaga aaacagtata
1321 aactttcaga ggcaaaatcc ttccaattt tttccacata ctttcatgcc ttgcctaaaa
1381 aaaatgaaaa gagagttggt atgtctcatg aatgttcaca cagaaggagt tggttttcat
1441 gtcatctaca gcatatgaga aaagctacct ttcttttgat tatgtacaca gatatctaaa
1501 taaggaagta tgagtttcac atgtatatca aaaatacaac agttgcttgt attcagtaga
1561 gttttcttgc ccacctattt tgtgctgggt ctaccttaa cccagaagac actatgaaaa
1621 acaagacaga ctccactcaa aatttatatg aacaccacta gatacttcct gatcaaacat
1681 cagtcaacat actctaaaga ataactccaa gtcttggcca ggcgcagtgg ctcacacctg
1741 taatcccaac actttgggag gccaaggtgg gtggatcatc taaggccggg agttcaagac
1801 cagcctgacc aacgtggaga acccccatct ctactaaaaa tacaaaatta gccggcgtg
1861 gtagcgcatg gctgtaatcc tggctactca ggaggccgag gcagaagaat tgcttgaact
1921 ggggacggcag aggttgcggt gagcccagat cgcgccattg cactccagcc tgggtaacaa
1981 gagcaaaact ctgtccaaaa aaaaaaaaa aaaaaa
```

SEQ ID NO: 16 - mDN-TNFR25 cDNA

```
ATGGAGGCAC GGCTGCTGCG GGGCTGCGTG GTGGAGCCTC TGTTCCTACC ACTGCTGCTG
CTGCTGCTGC TGCTGCTTGG TGGCCAGGGC CAGGGCGGCA TGTCTGGCAG GTGTGACTGT
GCCAGTGAGT CCCAGAAGAG GTATGGCCCG TTTTGTTGCA GGGCTGCCCC AAAGGGACAC
```

Figure 17 Continue

```
TACATGAAGG CCCCCTGCGC AGAACCCTGT GGCAACTCCA CCTGCCTTCC CTGTCCCTCG
GACACCTTCT TGACCAGAGA CAACCACTTT AAGACTGACT GTACCCGCTG CCAAGTCTGT
GATGAAGAGG CCCTTCAAGT GACCCTTGAG AACTGCTCGG CAAAGTCGGA CACCCACTGT
GGCTGCCAGT CAGGCTGGTG TGTTGACTGC TCCACCGAGC CATGTGGGAA AAGCTCACCT
TTCTCTTGTG TCCCATGCGG GGCTACAACA CCAGTCCATG AGGCTCCAAC CCCCCGGCCC
TGCCTGCCTG GCTTCTATAT ACGTGGCAAT GACTGCACGT CCTGCCCCAC GGGCTTCAGC
AGCGTTTGCC CTAAGGCTTG CACTGCTGTC TGTGGCTGGA AGCAGATGTT TTGGGTCCAG
GTGCTTCTAG GAGTCGCGTT CCTTTTTGGG GCTATCCTGA TCTGTGCATA TGGCTCTGGA
AGCGGGAGCG TCGACGATCT TTACGACGAT GATAAATAGT AA
```

IMMUNOMODULATING TUMOR NECROSIS FACTOR RECEPTOR 25 (TNFR25) AGONISTS, ANTAGONISTS, AND IMMUNOTOXINS

PRIORITY

This application is a continuation of U.S. application Ser. No. 12/534,228 filed on Aug. 3, 2009, which is a division of U.S. application Ser. No. 11/512,412, filed Aug. 30, 2006, now abandoned, which claims priority to U.S. Application Ser. No. 60/712,084, filed Aug. 30, 2005, all of which are incorporated herein by reference in their entirety.

BACKGROUND OF THE INVENTION

1. Field of the Invention

This invention relates to Tumor Necrosis Factor Receptor Super Family 25 (TNFR25) agonists, immunotoxins, antagonists and their use in treating cancer, inflammation and effecting immunosupression, respectively.

2. Background

Many disorders of the human immune system fall into two broad categories: those characterized by an attenuated immune response and those characterized by overzealous immune responses. Immunodeficiency is characterized by an attenuated response. There are congenital (inborn) and acquired forms of immune deficiency. Chronic granulomatous disease, in which phagocytes have trouble destroying pathogens, is an example of the former. AIDS ("Acquired Immune Deficiency Syndrome"), an infectious disease, caused by the HIV virus that destroys CD4+ T cells, is an example of the latter. An additional disease that may be characterized by an attenuated immune response is cancer. In contrast to healthy individuals, cancer patients' immune systems are no longer capable of effectively recognizing and/or destroying tumor cells.

Despite high hopes, there are no medications to date that directly increase the activity of the immune system. However, biological therapies have recently been used to recruit the immune system, either directly or indirectly, to fight diseases such as cancer. Monoclonal (MAb) antibodies are now frequently used as a biologic therapy. For example, monoclonal antibodies may react with specific types of cancer cells, and have direct or indirect antitumor effects.

Tumor vaccines may be employed therapeutically or for prophylaxis after primary therapy. Anti-tumor vaccines may need to induce cellular immunity in the form of tumor-specific cytotoxic T cells of the CD4 or CD8 phenotype. It is thought that effective anti-tumor immunity requires the generation and maintenance for long periods of times of such cytotoxic cells. In addition evidence indicates that the innate arm of the immune system must be activated in order to generate effective anti-tumor vaccines. Vaccines that enhance or generate humoral responses produce antibodies that can be detected over a relatively long period. To be effective, these antibodies need to be capable of targeting cell surface antigens in live cell assays. Maintaining specific cellular immune responses to antigen epitopes (adaptive immunity) may require more frequent immunizations, although memory cells can sustain the ability to respond and rechallenge the immunizing epitope. As such, it would of substantial benefit to have access to therapies that would be capable of boosting cancer specific cellular immune responses to tumor vaccines.

On the other end of the scale, an overactive immune system figures in a number of other disorders, particularly autoimmune disorders such as lupus erythematosus, type I diabetes (sometimes called "juvenile onset diabetes"), multiple sclerosis, psoriasis, rheumatoid arthritis and inflammatory bowel diseases such as Crohn's Disease and ulcerative colitis (UC). In these, the immune system fails to properly distinguish between self and non-self and attacks a part of the patient's own body. Other examples of overzealous immune responses in disease include hypersensitivities such as allergies and asthma.

Suppression of the immune system is often used to control autoimmune disorders or inflammation when this causes excessive tissue damage. Immunosuppressive medication intentionally induces an immunodeficiency in order to prevent rejection of transplanted organs. Commonly used immunosuppressants include glucocorticoids, azathioprine, methotrexate, cyclosporin, cyclophosphamide and mercaptopurine. In organ transplants, selective T cell inhibition prevents organ rejection, and cyclosporin, tacrolimus, mycophenolate mofetil and various others are used.

T lymphocytes play a central role in regulating immune responses. Helper T cells express the CD4 surface marker and provide help to B cells for antibody production and help CD8 T cells to develop cytotoxic activity. Other CD4 T cells inhibit antibody production and cytotoxicity. T cells regulate the equilibrium between attack of infected or tumorigenic cells and tolerance to the body's cells. A disregulated immune attack can lead to autoimmunity, while diminished immune responsiveness results in chronic infection and cancer.

Tumor Necrosis Factor Receptor 25 (TNFR25) also interchangeably referred to herein as Death receptor 3 (DR3), as discussed herein, is a regulator of T cell function. Death receptor 3 (DR3) (Chinnaiyan et al., Science 274:990, 1996) is a member of the TNF-receptor family. It is also known as TRAMP (Bodmer et al., Immunity 6:79, 1997), wsl-1 (Kitson et al., Nature 384:372, 1996), Apo-3 (Marsters et al., Curr Biol 6:1669, 1996), and LARD (Screaton et al., Proc Natl Acad Sci USA 94:4615, 1997) and contains a typical death domain. Transfection of 293 cells with human DR3 (hDR3) induced apoptosis and activated NF-κB. The cognate ligand for DR3 has recently been identified as TL1A (Migone et al., Immunity 16:479, 2002) and has been shown to have costimulatory activity for DR3 on T cells through the induction of NF-κB and suppression of apoptosis by expression cIAP2 (Wen et al., J Biol Chem 25:25, 2003). TL1A also binds to the decoy receptor 3 (DcR3/TR-6), indicating that fine-tuning of biological TL1A accessibility is of critical importance. Multiple spliced forms of human DR3 mRNA have been observed, indicating regulation at the post transcriptional level (Screaton et al., Proc Natl Acad Sci USA 94:4615, 1997).

Many TNF-receptor family members have the ability to induce cell death by apoptosis or induce costimulatory signals for T cell function. The regulation of these opposing pathways has recently been clarified for TNF-R1, the prototypic death domain-containing receptor that can cause apoptosis or proliferation of receptor positive T cells (Micheau and Tschopp. Cell 114:181, 2003). NF-κB activation by a signaling complex composed of TNF-R1 via TRADD, TRAF2 and RIP induces FLIPL association with a second signaling complex composed of TNFRI, TRADD and FADD, preventing caspase 8 activation as long as the NF-κB signaling persists. DR3 has been shown to be able to induce apoptosis in transfected cells and to induce NF-κB and all three MAP-kinase pathways (Chinnaiyan et al., Science 274:990, 1996; Bodmer et al., Immunity 6:79, 1997; Kitson et al., Nature 384:372, 1996; Marsters et al., Curr Biol 6:1669, 1996; Screaton et al., Proc Natl Acad Sci USA 94:4615, 1997; Wen et al., J Biol Chem 25:25, 2003). Blocking of NF-κB, but not of MAP-kinase and inhibition of protein synthesis resulted in DR3- mediated cell death, indicating that NF-κB signals mediate anti-apoptotic effects through the synthesis of anti-apoptotic proteins.

Expression of human DR3 mRNA is pronounced in lymphoid tissues, mainly in the spleen, lymph nodes, thymus, and small intestine, indicating an important role for DR3 in lymphocytes. Murine DR3 has been deleted by homologous recombination in embryonic stem cells (Wang et al., Mol Cell Biol 21:3451, 2001). DR3−/− mice show diminished negative selection by anti-CD3 in the thymus but normal negative selection by superantigens and unimpaired positive selection of thymocytes. Mature peripheral T cells were unaffected by DR3 deficiency. Despite a significant amount of preliminary research, the physiological function of DR3 remains poorly characterized.

All scientific publications including patent documents cited herein are incorporated by reference in their entirety for all purposes.

SUMMARY OF THE INVENTION

One aspect of the invention relates to an antibody that binds a Tumor Necrosis Factor Receptor 25 (TNFR25) antigen and that can act as a TNFR25 agonist. In one embodiment, the antibody is capable of increasing OT-I CD8 cell expansion when cross-primed by gp96-Ig-ovalbumin relative to a control antibody. In a further embodiment, the antibody is purified monoclonal antibody 4C12.

Another aspect of this invention relates to a TNFR25-specific toxin comprising a toxic agent linked to polypeptide that binds the TNRF25 receptor. In one embodiment of this aspect, the toxin-comprising portion includes the monoclonal antibody 4C12 or an immunospecific portion of 4C12. In another embodiment, the toxic agent is selected from a radioactive isotope, ricin, abrin, diphtheria toxin, *Pseudomonas* exotoxin, or metal ion. In a further embodiment, the polypeptide that binds the TNRF25 receptor is the TL1A protein or a fragment or variant thereof. In another aspect of the invention, the TNFR25-specific toxin is used in a method of treating cancer in a patient. Specifically, the method includes depleting a patient of CD4+/CD25+ T regulatory cells (Tregs) by providing the patient with the TNFR25-specific toxin and also providing the patient with a chemotherapeutic agent.

Yet another aspect of this invention relates to a method of activating TNFR25 receptor expressed on a cell comprising contacting the cell with a TNFR25 agonist. The agonist may be selected from a monoclonal antibody 4C12; an antibody that binds TNFR25 and that can increase OT-I CD8 cell expansion when cross-primed by gp96-Ig-ovalbumin relative to a control antibody; a soluble TL1A protein; an expression vector with an expression cassette capable of driving the transgenic expression of a TNFR25 agonist antibody; an expression vector with an expression cassette capable of driving the transgenic expression of a soluble TL1A; or an expression vector with an expression cassette capable of driving the transgenic expression of a TNFR25. This method further includes observing an increase in TNFR25 receptor signaling.

An additional aspect of this invention relates to an antibody that is capable of acting as a TNFR25 antagonist. In one embodiment, the antibody binds a TL1A and is capable of decreasing OT-I CD8 cell expansion when cross-primed by gp96-Ig-ovalbumin relative to a control antibody. In a further embodiment, the antibody is the purified monoclonal antibody L4G6.

A further aspect of the invention relates to a method of inhibiting TNFR25 receptor signaling in a cell. The method includes contacting the cell with a TNFR25 antagonist. The method further includes observing a decrease in TNFR25 receptor signaling.

Another aspect of this invention relates to a tumor vaccine comprising a tumor antigen and a TNFR25 agonist as a biological response modifier. A further embodiment of this vaccine also includes an adjuvant.

In yet another aspect of this invention, after isolating a tumor specific antigen, a vaccine comprising a tumor specific antigen and a TNFR25 agonist, is used to immunize a patient against the tumor.

A further aspect of this invention relates to a method of treating and/or preventing gut inflammation comprising providing a patient in need thereof a with an effective amount of a therapeutic composition comprising a TNFR25 agonist.

A further aspect of this invention relates to a therapeutic composition for the facilitation of an organ transplant comprising a TNFR25 antagonist and an immunosuppressant. In one embodiment of this aspect, the immunosuppressant is glucocorticoid, azathioprine, methotrexate, cyclosporin, cyclophosphamide, mercaptopurine, tacrolimus or mycophenolate mofetil.

In another aspect of the invention, a TNFR25 antagonist composition is used in a method of transplanting a tissue from a donor into a host. This method includes the steps of obtaining tissue from a donor; providing a host with a TNFR25 antagonist composition; and transplanting the tissue into the host.

Another aspect of this invention relates to a method of inhibiting the clonal expansion of a population of cognate CD8 T cells. This method includes exposing the CD8 T cells to their cognate antigen and exposing the CD8 T cells to a TNFR25 antagonist. In a further embodiment, the cognate antigen is associated with tissue to be transplanted from a donor into a host.

Another aspect of the invention relates to an isolated TNFR25 antagonist comprising a polypeptide encoded by a nucleic acid comprising sequence that hybridizes under stringent conditions to SEQ ID NOs: 4, 5, 6 and/or 16, and wherein the sequence encodes an amino acid sequence capable of binding a TL1A protein. In one embodiment, the sequence hybridizes under stringent conditions to SEQ ID NO: 4. In another embodiment, the sequence hybridizes under stringent conditions to SEQ ID NO: 5. In a further embodiment, the sequence hybridizes under stringent conditions to SEQ ID NO: 6. In a further embodiment, the sequence hybridizes under stringent conditions to SEQ ID NO: 16. In yet another embodiment, the TL1A is human or mouse TL1A.

Another aspect of the invention relates to a method of treating and/or preventing lung inflammation comprising providing a patient in need thereof a with an effective amount of a therapeutic composition comprising the TNFR25 antagonist comprising a polypeptide encoded by a nucleic acid comprising sequence that hybridizes under stringent conditions to SEQ ID NOs: 4, 5, 6 and/or 16, and wherein the sequence encodes an amino acid sequence capable of binding a TL protein.

Another aspect of the invention relates to a method of transplanting a tissue from a donor into a host comprising obtaining the tissue from the donor; providing the host with the TNFR25 antagonist comprising a polypeptide encoded by a nucleic acid comprising sequence that hybridizes under stringent conditions to SEQ ID NOs: 4, 5, 6 and/or 16, and wherein the sequence encodes an amino acid sequence capable of binding a TL1A protein; and transplanting the tissue into the host.

Another aspect of the invention relates to a composition comprising a polypeptide encoded by a sequence that hybridizes under stringent conditions to SEQ ID NOs: 3 and/or 7, and wherein the sequence encodes an amino acid sequence capable of binding a TNFR25 receptor protein; and a toxic agent. In one embodiment, the toxic agent is selected from the group consisting of a radioactive isotope, ricin, abrin, diphtheria toxin, *Pseudomonas* exotoxin, and metal ion.

Another aspect of the invention relates to a method of treating cancer in a patient comprising depleting a patient of CD4+/CD25+ T regulatory cells (Tregs) by providing the patient with a composition comprising the toxin of claim 39; and providing a patient with a chemotherapeutic agent.

A further aspect of the invention relates to a method of treating and/or preventing gut inflammation comprising providing a patient in need thereof a with an effective amount of a composition comprising a polypeptide encoded by a sequence that hybridizes under stringent conditions to SEQ ID NOs: 3 and/or 7, and wherein the sequence encodes an amino acid sequence capable of binding a TNFR25 receptor protein. In one embodiment, the inflammation is a result of irritable bowel syndrome. In another embodiment, the gut inflammation is a result of Crohn's disease.

A further aspect of the invention relates to a tumor vaccine comprising a tumor antigen and a polypeptide encoded by a sequence that hybridizes under stringent conditions to SEQ ID NOs: 3 and/or 7, and wherein the sequence encodes an amino acid sequence capable of binding a TNFR25 receptor protein, as a biological response modifier.

Still another aspect of the invention relates to an expression vector comprising a nucleic acid sequence that hybridizes under stringent conditions to SEQ ID NOs: 3 and/or 7, and that encodes an amino acid sequence capable of binding a TNFR25 receptor protein.

Yet a further aspect of the invention relates to an expression vector comprising a nucleic acid that hybridizes under stringent conditions to SEQ ID NOs: 4, 5, 6 and/or 16, and wherein the sequence encodes an amino acid sequence capable of binding a TL1A protein Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. The present invention may be practiced without some or all of these specific details. In other instances, well known process operations have not been described in detail, in order not to unnecessarily obscure the present invention. Accordingly, the drawings and description are to be regarded as illustrative in nature, and not as restrictive.

BRIEF DESCRIPTION OF THE DRAWINGS

FIG. 1A depicts the expression of murine TNFR25 in lymph node cells. MFI is indicated by black numbers for isotype control antibody as primary antibody and in shaded for anti-TNFR25. Detection of TNFR25 required a triple sandwich of primary hamster anti-TNFR25 monoclonal antibody, followed by goat anti-hamster biotin and PE-labeled Strept-Avidin. 1B depicts the expression of TNFR25 on activated lymphocytes. Activation of splenocytes was done with immobilized anti-CD3 (5 µg/ml) and anti CD28 (1 µg/ml) or LPS (1 µg/ml) for 24 hours. Cells were gated for CD4 or CD8 or B220 positive and 7-AAD negative cells (subscript a stands for activated CD4, CD8 or B cells). In the histograms, MFI for expression of TNFR25 on resting splenocytes and on activated splenocytes is shown. 1C depicts the expression of TNFR25 on thymocytes. Thymocytes were gated on CD4/CD8 double negative, double positive or single positive cells and evaluated for anti-TNFR25 fluorescence.

FIG. 17 shows SEQ ID NOs: 1-7 and SEQ ID NO: 16 and selected public database accession numbers.

DETAILED DESCRIPTION OF THE INVENTION

Figure 2A:
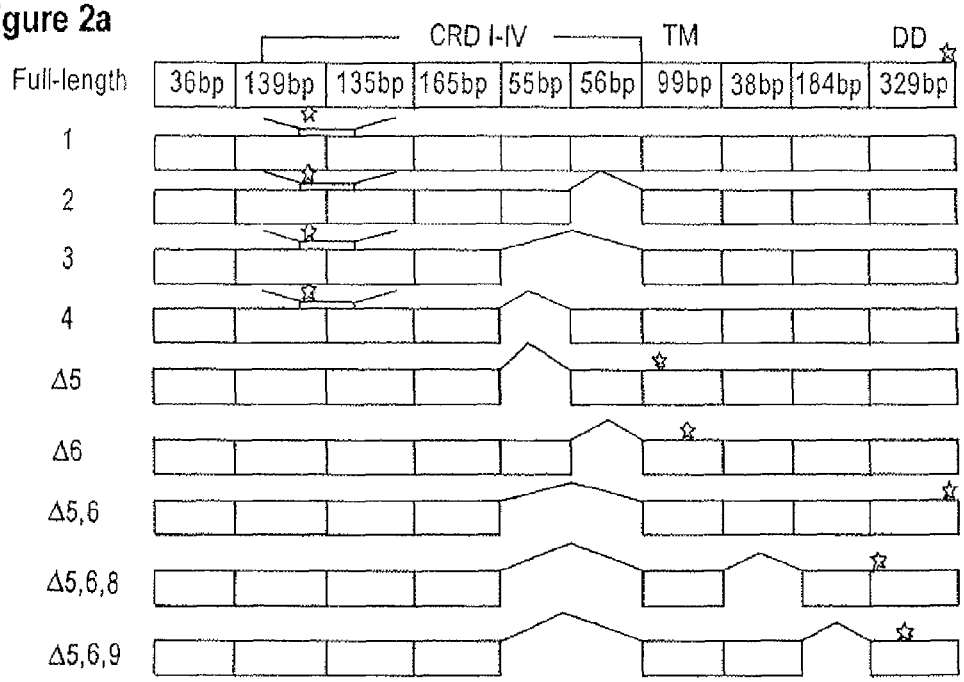
FIG. 2A depicts splice forms of murine TNFR25. Splice forms were obtained by RT-PCR of mRNA obtained from resting murine splenocytes and murine cell lines. CRD: cysteine-rich domain; TM: transmembrane domain; DD: death domain. Asterisks: in frame stop codon. In splice forms 1-4 the intron between exon 2 and 3 is not spliced out and contains a premature stop codon. Splice forms 1-4 are likely to be nonfunctional proteins. Murine 45 and 46 (corresponding to human Δ6 and Δ6,7) lack a complete transmembrane domain and are predicted to be secreted forms that could act as soluble decoy receptor for TL1A. Δ5,6 (potentially corresponding to human Δ3) and FL splice forms are studied as transgenes in this report. Δ5,6,8 and Δ5,6,9 (no human homologues) are predicted to be membrane anchored but lack the death domain and may have altered signaling properties or may act as dominant negative splice forms. The preferred DN TNFR25 disclosed herein was truncated after the TM domain. 2B depicts activation-induced alternative splicing of TNFR25. Both mouse and human TNFR25 are spliced after activation. The human splicing is shown here because splice forms of TNFR25 are separated better in size after gel electrophoresis than murine forms. Splice forms were confirmed by sequencing. PBL were isolated by Ficoll-Hypaque gradient centrifugation. Five million cells were used in each sample and mRNAs were extracted and converted to cDNA using the Invitrogen cDNA synthesis kit. Activation of PBL by PHA (5 µg/ml), immobilized anti-CD3 (5 µg/ml) and soluble anti-CD28 (1 µg/ml), or PMA (10 ng/ml) and ionomycin (400 ng/ml) as indicated. The cells were harvested at the indicated time points and RT-PCRs were performed; β-actin was used as the internal control. 2C depicts activation-induced splicing is PKC-dependent and protein synthesis-independent. Freshly isolated PBL cells were stimulated with PMA (10 ng/ml) alone, or ionomycin (400 ng/ml) alone or in combination. PBL were pretreated with H7 (50 µM), or cycloheximide (10 µg/ml) for half an hour, then PMA and ionomycin were added into the cell culture. The cells were harvested after 12 hours for RT-PCR analysis.

It is an object of the invention to provide novel compositions and methods utilizing immunomodulating agents that can either stimulate or indirectly augment the immune system or in other cases, have an immunosuppressive effect. TNFR25 agonists disclosed herein represent biological response modifiers that alter the interaction between the body's cellular immune defenses and cancer cells to boost, direct, or restore the body's ability to fight the cancer when given with tumor vaccines. TNFR25-specific toxic agents disclosed herein are capable of increasing the effectiveness of a chemotherapeutic regimen by depleting a cancer patient of naturally occurring immunosuppressive cells. TNFR25 agonists disclosed herein can also have a healing effect. They can be used, among other things, to treat disease that caused by chronic inflammation such as inflammatory bowel disease. TNFR25 antagonists disclosed herein are capable of inhibiting CD8 T cell-mediated cellular immune responses and can for example, to treat asthma and mitigate organ or tissue rejection following a tissue transplantation.

1. Definitions

In describing the present invention, the following terms will be employed, and are intended to be defined as indicated below.

An "antigen" includes any substance that may be specifically bound by an antibody molecule. Thus, the term "antigen" encompasses biologic molecules including, but not limited to, simple intermediary metabolites, sugars, lipids, autoacids, and hormones, as well as macromolecules such as complex carbohydrates, phopholipids, nucleic acids and proteins.

An "antigenic composition" may comprise an antigen (e.g, a peptide or polypeptide), a nucleic acid encoding an antigen (e.g, an antigen expression vector), or a cell expressing or presenting an antigen. See U.S. Pub. No. 2003/0185840, which is hereby incorporated by reference in its entirety.

An "immunogen" is a macromolecular antigen that is capable of initiating lymphocyte activation resulting in an antigen-specific immune response. An immunogen therefore includes any molecule which contains one or more epitopes that will stimulate a host's immune system to initiate a secretory, humoral and/or cellular antigen-specific response.

The term "antibody" encompasses polyclonal and monoclonal antibody preparations. Antibodies of the invention may be prepared in any mammal, including mice, rats, rabbits, goats and humans. The antibody may be a member of one of the following immunoglobulin classes: IgG, IgM, IgA, IgD, or IgE, and the subclasses thereof, and preferably is an IgG1 antibody.

The term antibody also refers to functional equivalents of the antibodies described in this specification. Functional equivalents have binding characteristics comparable to those of the antibodies, and include, for example, chimerized, hybrid, humanized and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424. Functional equivalents include polypeptides with amino acid sequences substantially the same as the amino acid sequence of the variable or hypervariable regions of the antibodies of the invention. "Substantially the same" amino acid sequence is defined herein as a sequence with at least 70%, preferably at least about 80%, and more preferably at least about 90% homology to another amino acid sequence, as determined by the FASTA search method in accordance with Pearson and Lipman, Proc. Natl. Acad. Sci. USA 85, 2444-2448 (1988).

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins.

Methods of making polyclonal and monoclonal antibodies are known in the art. Polyclonal antibodies are generated by immunizing a suitable animal, such as a mouse, rat, rabbit, sheep or goat, with an antigen of interest. In order to enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., in order to enhance the immunogenicity thereof.

Rabbits, sheep and goats are preferred for the preparation of polyclonal sera when large volumes of sera are desired. These animals are good design choices also because of the availability of labeled anti-rabbit, anti-sheep and anti-goat antibodies. Immunization is generally performed by mixing or emulsifying the antigen in saline, preferably in an adjuvant such as Freund's complete adjuvant ("FCA"), and injecting the mixture or emulsion parenterally (generally subcutaneously or intramuscularly). The animal is generally boosted 2-6 weeks later with one or more injections of the antigen in saline, preferably using Freund's incomplete adjuvant ("FIA"). Antibodies may also be generated by in vitro immunization, using methods known in the art. Polyclonal antisera is then obtained from the immunized animal.

Monoclonal antibodies are generally prepared using the method of Kohler and Milstein, Nature (1975) 256:495-497, or a modification thereof or Campbell in "Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1985); as well as by the recombinant DNA method described by Huse et al in Science 246, 1275-1281 (1989).

Typically, a mouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-screting hybridomas are then cultured either in vitro (e.g., in tissue culture bottles or hollow fiber reactors), or in vivo (e.g., as ascites in mice).

The "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the terms "immuno-specific," "immunological binding" and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')2" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent VH::VL heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked VH::VL heterodimer which is expressed from a gene fusion including VH- and VL-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

"Cognate antigen" as used herein refers to an antigen for which a CD8 T cell receptor (TCR) is immuno-specific. Such antigen, which are generally derived from e.g. pathogen, transplanted tissues (alloantigen) and tumor cells, are recognized by the immune system as non-self. Binding of the cognate antigen to its CD8 T cell receptor results in the clonal expansion of that T cell. A growing population of cognate CD8 T cells is then in a position to mount a cellular immunological response against the source of the offending cognate antigen.

Antibodies of the invention can also be used to make "immunotoxins." The hybrid molecule combines the specificity of an antibody or antigen with the toxicity of the toxin. As such, immunotoxin molecules have an antigen binding portion and a toxic agent portion. Immunotoxins are preferably specific for a cell surface molecule, e.g., TNFR25, and facilitate the delivery of a toxic agent to a cell expressing the aforementioned cell surface molecule.

Preferably, the "toxic agents" have a cytostatic and/or cytotoxic effect on the cell to which it is delivered. Preferred toxic agents are, for example, radioactive isotopes, fluorescers, chemiluminescers, enzymes, enzyme substrates, enzyme cofactors, enzyme inhibitors, dyes, and metal ions. Toxic agents include but are not limited to Iodine-131, Indium-111, and Technetium-99m, Technetium-99m, Indium-111, Yttrium-90, doxorubicin (Yang et al. (1988) Proc. Natl. Acad. Sci. USA 85:1189-1193), daunorubicin (Diener et al. (1985) Science 231:148-150; Dillman et al. (1988) Cancer Res. 48:6097-6102), methotrexate (Uadia et al. (1985) J Natl Cancer Inst. 74:29-35; Deguchi et al. (1986) Cancer Res. 46:3751-3755), and chlorambucil (Symth et al. (1986) J Immunol. 137:3361-3366). Other toxic agents include ricin, abrin, diphtheria toxin and *Pseudomonas* exotoxin, or an enzymatically active portion (A chains) thereof. See, e.g., U.S. Pat. No. 4,753,894 to Frankel et al.; Nevelle, et al. (1982) Immunol Rev 62:75-91; Ross et al. (1980) European J Biochem 104; Vitteta et al. (1982) Immunol Rev 62:158-183; Raso et al. (1982) Cancer Res 42:457-464, and Trowbridge et al. (1981) Nature 294:171-173. Also included are enzymatically active toxins and fragments thereof such as modeccin, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, and enomycin.

"Toxic agents" can also be chemotherapeutic agents. The term "chemotherapeutic agent" as used herein generally relates to compounds administered to stop, slow or reverse unwanted proliferation of cells. Preferably such agents have an anti-proliferative effect.

Chemotherapeutic agents may be anti-metabolites such as 5-FU, for example. 5-FU-based chemotherapy comprises administration of 5-FU, its derivatives, alone or with other chemotherapeutics, such as leucovorin or with a DPD inhibitor such as uracil, 5-ethynyluracil, bromovinyluracil, thymine, benzyloxybenzyluracil (BBU) or 5-chloro-2,4-dihydroxypyridine. Furthermore, it has been found that co-administration of a 5'-deoxy-cytidine derivative of the formula (I) with 5-FU or a derivative thereof significantly improves delivery of a chemotherapeutic agent selectively to tumor tissues as compared with the combination of 5-FU or a derivative thereof with a DPD inhibitor 5-ethynyluracil.

Alternatively, genotoxic agents are those that form persistent genomic lesions and are preferred for use as chemotherapeutic agents in the clinical management of unwanted cellular proliferation. The rate of cellular repair of genotoxin-induced DNA damage, as well as the rate of cell growth via the cell division cycle, affects the outcome of genotoxin therapy. A general class of genotoxic compounds that are used for treating many cancers are DNA alkylating agents and DNA intercalating agents. Psoralens are genotoxic compounds known to be useful in the photochemotherapeutic treatment of cutaneous diseases such as psoriasis, vitiligo, fungal infections and cutaneous T cell lymphoma. Harrison's Principles of Internal Medicine, Part 2 Cardinal Manifestations of Disease, Ch. 60 (12th ed. 1991). Another general class of genotoxic compounds, members of which can alkylate or intercalate into DNA, includes synthetically and naturally sourced antibiotics. Of particular interest herein are antineoplastic antibiotics, which include but are not limited to the following classes of compounds represented by: amsacrine; actinomycin A, C, D (alternatively known as dactinomycin) or F (alternatively KS4); azaserine; bleomycin; carminomycin (carubicin), daunomycin (daunorubicin), or 14-hydroxydaunomycin (adriamycin or doxorubicin); mitomycin A, B or C; mitoxantrone; plicamycin (mithramycin); and the like. Still another general class of genotoxic agents that are commonly used and that alkylate DNA, are those that include the haloethylnitrosoureas, especially the chloroethylnitrosoureas. Representative members of this broad class include carmustine, chlorozotocin, fotemustine, lomustine, nimustine, ranimustine and streptozotocin. Haloethylnitrosourea first agents can be analogs or derivatives of any of the foregoing representative compounds.

Tumors currently manageable by platinum coordination compounds such as cisplatin or oxaliplatin include testicular, endometrial, cervical, gastric, squamous cell, adrenocortical and small cell lung carcinomas along with medulloblastomas and neuroblastomas. Other cytotoxic anti-cancer therapeutic agents include, for example, BEP (bleomycin, etoposide, cisplatin) for testicular cancer, MVAC (methotrexate, vinblastine, doxorubicin, cisplatin) for bladder cancer, MVP (mitomycin C, vinblastine, cisplatin) for non-small cell lung cancer treatment.

Yet another general class of genotoxic agents, members of which alkylate DNA, includes the sulfur and nitrogen mustards. These compounds damage DNA primarily by forming covalent adducts at the N7 atom of guanine Representative members of this broad class include chlorambucil, cyclophosphamide, ifosfamide, melphalan, mechloroethamine, novembicin, trofosfamide and the like. Oligonucleotides or analogs thereof that interact covalently or noncovalently with specific sequences in the genome of selected cells can also be used as genotoxic agents, if it is desired to select one or more predefined genomic targets as the locus of a genomic lesion.

Another class of agents, members of which alkylate DNA, include the ethylenimines and methylmelamines. These classes include altretamine (hexamethylmelamine), triethylenephosphoramide (TEPA), triethylenethiophosphoramide (ThioTEPA) and triethylenemelamine, for example.

Additional classes of DNA alkylating agents include the alkyl sulfonates, represented by busulfan; the azinidines, represented by benzodepa; and others, represented by, e.g., mitoguazone, mitoxantrone and procarbazine. Each of these classes includes analogs and derivatives of the respective representative compounds.

In one embodiment, chemotherapeutic agents are inhibitors of receptor tyrosine kinases such as EGFR and HER2-neu and are employed as selective inhibitors of the growth of proliferative cells. For example, erbstatin, an EGF receptor tyrosine kinase inhibitor, reduces the growth of EGFR expressing human carcinoma cells. Various derivatives of styrene are also stated to possess tyrosine kinase inhibitory properties and to be of use as anti-tumour agents. Two such styrene derivatives are Class I RTK inhibitors whose effectiveness have been demonstrated by attenuating the growth of human squamous cell carcinoma injected into nude mice. Certain 4-anilinoquinazoline derivatives are useful as inhibitors of receptor tyrosine kinases. The very tight structure-activity relationships shown by these compounds indicates a clearly-defined binding mode, where the quinazoline ring binds in the adenine pocket and the anilino ring binds in an adjacent, unique lipophilic pocket. Three 4-anilinoquinazoline analogues (two reversible and one irreversible inhibitor) have been evaluated clinically as anticancer drugs. Additionally, the monoclonal antibody trastazumab (Herceptin™) for the treatment of HER2-neu overexpressing metastatic breast cancers. Scheurle, et al., Anticancer Res 20:2091-2096, 2000.

An "expression vector" is any genetic element, e.g., a plasmid, chromosome, virus, behaving either as an autonomous unit of polynucleotide replication within a cell. (i.e., capable of replication under its own control) or being rendered capable of replication by insertion into a host cell chromosome, having attached to it another polynucleotide segment, so as to bring about the replication and/or expression of the attached segment. Suitable vectors include, but are not limited to viruses, plasmids and cosmids.

Expression vectors contain an "expression cassette" which includes a polynucleotide sequence to be transcribed operably linked to polynucleotide sequences which are necessary to effect ligation or insertion of the vector into a desired host cell and to effect the transcription of the polynucleotide to be expressed. Such sequences include promoter sequences to effect transcription, enhancer sequences to increase transcription, ribosomal binding site sequences and transcription and translation termination sequences. Alternatively, expression vectors may be capable of directly expressing nucleic acid sequence products encoded therein without ligation or integration of the vector into host cell DNA sequences.

The term "operably linked" refers to the linkage of a DNA segment to another DNA segment in such a way as to allow the segments to function in their intended manners. A DNA sequence encoding a gene product is operably linked to a regulatory sequence when it is ligated to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers may be located upstream, downstream or embedded within the coding regions of the DNA sequence. A DNA for a signal sequence is operably linked to DNA coding for a polypeptide if the signal sequence is expressed as a preprotein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

"Small molecule" as used herein refers to molecular weight synthetic compounds designed to interact with a specific protein known to be involved in a given disease condition. Libraries of such compounds may be readily synthesized by combinatorial chemistry for example, and screened for TNFR25 agonist/antagonist activity using conventional techniques.

The terms "TNFR-SF25", "TNFR25" or "DR3" are all used interchangeably herein for a member of the TNF receptor family whose complete biological function was previously not known. See U.S. Pat. No. 6,713,061, and Borysenko, et al., Biochem Biophys Res Commun. 2005 Mar. 18; 328(3):794-9, Sheikh, et al., Curr. Cancer Drug Targets. 2004 February; 4(1):97-104, which are incorporated by reference in their entirety. However, the inventors, however, have made a number of important discoveries. The cDNA sequence encoding mouse TNFR25 is shown as SEQ ID NO: 1. The cDNA encoding human TNFR25 is shown as SEQ ID NO: 2.

Unlike that of any other member of the TNF-R family, DR3 expression was found to be controlled by alternative mRNA splicing. Resting T cells express little or no DR3 protein, but contained high levels of randomly spliced DR3 mRNA. Upon T cell activation via the T cell receptor, protein kinase C (PKC) is activated. PKC activation in turn mediates correct splicing of full-length DR3 and surface expression of the protein. This unique regulation of DR3 expression allows for rapid DR3 protein expression on T cells and enables environmental regulation of DR3 expression via influencing PKC levels responsible for DR3 splicing and expression.

DR3 is also involved in co-stimulating T cell polarization and in stimulating the production of IL-13 and IL-10 in Th2 polarized cells. This is an important observation because among other things, IL-10 production plays a critical role in suppressing inflammatory bowel disease.

Transgenic expression of TNFR25 in T cells mediates TH2 polarization of cytokine and antibody production upon T cell activation and antigen exposure. In addition transgenic TNFR25 partially inhibits TCR driven proliferation of CD4 and CD8 cells and reduced total T cell numbers in lymphoid organs without inducing apoptosis. CD8 cells were more affected by TNFR25 than CD4 cells. As such, TNFR25 signals are important in effector responses to pathogens by shaping the ensuing polarization towards TH2 or towards a mixed TH1/TH2 response.

TNFR25 transgenic mice are highly susceptible to antigen induced airway inflammation in an asthma model in mice and produced increased quantities of IL-13 and eosinophils in the lung upon antigen exposure by inhalation. Transgenic mice expressing a dominant negative form of TNFR25 showed increased resistance to airway hyperreactivity when compared to wild type mice.

"TL1A" is referred to herein as a TNF-like factor that acts as a costimulator of IFN-gamma secretion through binding to the death domain-containing receptor, DR3. TL1A, like TNF, is also presumed to circulate as a homotrimeric soluble form. As such, "soluble TL1A" as used herein, refers to homotrimeric TL1A. The term is not limited to any species specific form. However, the cDNA sequence for the human TL1A monomer is provided as SEQ ID NO: 7 and that of mouse as SEQ ID NO: 3.

TL1A has been suggested to play a role in inflammatory bowel disease (IBD) by functioning as a Th1-polarizing cytokine. It has been shown that the amount of TL1A protein and the number of TL1A-positive cells correlate with the severity of inflammation, most significantly in Crohn's Disease (CD). It has also been shown that the addition of recombinant human TL1A to cultures of PHA-stimulated lamina propria mononuclear from CD patients significantly augmented IFN-gamma production by 4-fold, whereas a minimal effect was observed in control patients. Additionally, a blocking anti TL1A antibody was able to ameliorate asthma in wild type mice indicating that TNFR25 and TL1A are involved in the pathogenesis of asthma.

The receptors of the human body work by being stimulated or inhibited by natural (such as hormones, cytokines and neurotransmitters) or synthetic (such as drugs, e.g., antibodies or small molecules) agonists.

"TNFR25 agonist" is referred to herein as a substance that binds to the TNFR25 receptor and triggers a response in the cell on which the TNFR25 receptor is expressed similar to a response that would be observed by exposing the cell to a natural TNFR25 ligand, e.g., TL1A. An agonist is the opposite of an antagonist in the sense that while an antagonist may also bind to the receptor, it fails to activate the receptor and actually completely or partially blocks it from activation by endogenous or exogenous agonists. A partial agonist activates a receptor but does not cause as much of a physiological change as does a full agonist.

Soluble TL1A might be given in therapeutic form to a patient to increase the activation of the TNFR25 receptor in a given cell population as a TNFR25 agonist.

Alternatively, another example of a TNFR25 agonist is an antibody that is capable of binding and activating TNFR25. For example, the monoclonal antibody 4C12 binds and activates TNFR25 signaling. In another embodiment and in the context of this invention, a TNFR25 agonist may be derived from an expression vector with an expression cassette capable of ectopically driving the transgenic expression of a TNFR25 agonist antibody and/or TL1A protein at a chosen location or at a chosen time. In yet another embodiment, a TNFR25 agonist leading to an increase in TNFR25 signaling in a tissue is provided by an expression vector with an expression cassette capable of driving the transgenic expression of TNFR25 itself. This would be useful in a situation where increased TNFR25 signaling is desired in a tissue in which there is an excess of exogenous or endogenous TNFR25 agonist(s) relative to receptor.

"TNFR25 antagonist" is referred to herein as a substance that inhibits the normal physiological function of a TNFR25 receptor. Such agents work by interfering in the binding of endogenous receptor agonists/ligands such as TL1A, with TNFR25 receptor. An example of a TNFR25 antagonist is a dominant negative TNFR25 receptor. Preferably, the TNFR25 antagonist used herein is an antibody specific to TL1A which interferes with TL1A's ability to activate the TNRF25 receptor. Most preferably, that antibody is the monoclonal antibody L4G6. In another embodiment, the TNFR25 antagonist is a fusion protein of the extracellular portion of TNFR25 or an alternative splice form of TNFR25 with The Fc portion of immunoglobulin or any other suitable fusionpartner. In another embodiment, the TNFR25 antagonist is a soluble form of TNFR25 made by truncation above the transmembrane binding domain, either as alternative splice form or as an artificial construct. In another embodiment, the TNFR25 antagonist is an antibody that specifically binds TNFR25 and interferes with its binding to its natural ligand(s). In another embodiment, TNFR25 antagonist may be an expression vector with an expression cassette capable of driving the transgenic expression of an antisense mRNA, RNAi or ribozyme that is capable of knocking down endogenous TNFR25 and/or TL1A mRNA transcription and/or translation at a chosen location or at a chosen time. In yet another embodiment, one may decrease TNFR25 signaling in a tissue by providing an expression vector with an expression cassette capable of driving the transgenic expression of a dominant negative TNFR25.

TNFR25 antagonists or agonists may be in the form of aptamers. "Aptamers" are DNA or RNA molecules that have been selected from random pools based on their ability to bind other molecules. In one embodiment, aptamers specifically bind TNFR25 to block binding of its natural ligand, e.g., TL1A, or which bind TL1A itself, and prevent it from binding TNFR25. In another embodiment, aptamers specifically bind the TNFR25 receptor and activate it.

"Dominant negative" or "DN" as used herein refers to an exogenously provided structural variant of TNFR25 that acts to block endogenous TNFR25. For example, a molar excess of a DN will out compete endogenous TNFR25 for binding of the TNFR25 ligand, e.g., TL1A. Preferably the DN is the same as the wild type TNFR25 except that it is missing the intracellular domain. Alternatively, the DN is the same as the wild type TNFR25 except that it is missing the transmembrane and the intracellular domain. The coding sequence for the mouse DN TNFR25 is provided in SEQ ID NO: 4. The coding sequence for the human DN TNFR25 is provided in SEQ ID NO: 5. The coding sequence for the human DN TNFR25 containing only the extracellular domain is provided in SEQ ID NO: 6.

The invention also involves the coding sequences that are substantially identical to SEQ ID NOs: 3-7. The skilled artisan will also appreciate that oligonucleotide sequences substantially identical to SEQ ID NOs: 3-7 may differ from SEQ ID NOs: 3-7, respectively, with respect to the identity of at least one nucleotide base. However, all oligonucleotides sequences substantially identical to SEQ ID NOs: 3-7 will hybridize under stringent conditions (as defined herein) to all or a portion of the complements of SEQ ID NOs: 3-6 (i.e., target sequences), respectively. The terms "hybridize(s) specifically" or "specifically hybridize(s)" refer to complementary hybridization between an oligonucleotide (e.g., a primer or labeled probe) and a target sequence. The term specifically embraces minor mismatches that can be accommodated by reducing the stringency of the hybridization media to achieve the desired priming for the PCR polymerases or detection of hybridization signal.

Under stringent hybridization conditions, only highly complementary, i.e., substantially identical nucleic acid sequences, hybridize. Preferably, such conditions prevent hybridization of nucleic acids having 3 or more mismatches out of 20 contiguous nucleotides, more preferably 2 or more mismatches out of 20 contiguous nucleotides, most preferably one or more mismatch out of 20 contiguous nucleotides. The hybridizing portion of the hybridizing nucleic acid is at least about 90%, preferably at least about 95%, or most preferably about at least about 98%, identical to the sequence of a target sequence, or its complement.

Hybridization of a nucleic acid to a nucleic acid sample under stringent conditions is defined below. Nucleic acid duplex or hybrid stability is expressed as a melting temperature ($T_m$), which is the temperature at which the probe dissociates from the target DNA. This melting temperature is used to define the required stringency conditions. If sequences are to be identified that are substantially identical to the probe, rather than identical, then it is useful to first establish the lowest temperature at which only homologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5×Denhart's solution/1.0% SDS, and washing in 0.2×SSC/0.1% SDS at room temperature. Moderately stringent conditions include washing in 3×SSC at 42° C. The parameters of salt concentration and temperature may be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

"Immunosuppressants" as the term is used herein are important drugs necessary for the treatment of inflammatory diseases and facilitation of organ transplants. For example, Cyclosporin A (CsA) has considerable immunosuppressive activity. It has revolutionized organ transplantation and is commonly used in the treatment of autoimmune diseases. For a recent review of the use of CsA and its mechanisms of action, see Wenger et al; Cyclosporine Chemistry, Structure-activity relationships and Mode of Action, Progress in Clinical Biochemistry and Medicine, Vol. 2, 176 (1986). However, CsA is a powerful medication that can have severe side effects such as renal failure, bone marrow suppression and infertility.

Corticosteroids are also used in inflammatory conditions for their anti-inflammatory effects. They have a rapid onset of action, and profoundly affect many parts of the immune system as well as most other body systems. Corticosteroids are a cornerstone of treating most types of vasculitis, and are often used in combination with other immunosuppressive medications. However, long term use of corticosteroid can also have severe side effects including hypertension, weight gain, acne, and a swollen face. Other immunosuppressives include azathioprine, methotrexate, cyclophosphamide, mercaptopurine, tacrolimus and mycophenolate mofetil.

As a general matter, the agonists and antagonists may be provided to a patient in either compositions that are to be swallowed, injected, inhaled or provide by way of suppositories. Alternatively, the compostions may be formulating into ear or eye drops.

The term "asthma" as used herein includes any asthmatic condition marked by recurrent attacks of paroxysmal dyspnea (i.e., "reversible obstructive airway passage disease") with wheezing due to spasmodic contraction of the bronchi (so called "bronchospasm"). Asthmatic conditions which may be treated or even prevented in accordance with this invention include allergic asthma and bronchial allergy characterized by manifestations in sensitized persons provoked by a variety of factors including exercise, especially vigorous exercise ("exercise-induced bronchospasm"), irritant particles (pollen, dust, cotton, cat dander) as well as mild to moderate asthma, chronic asthma, severe chronic asthma, severe and unstable asthma, nocturnal asthma, and psychologic stresses. The methods of this invention may be particularly useful in preventing the onset of asthma in mammals e.g., humans afflicted with reversible obstructive disease of the lower airway passages and lungs as well as exercise-induced bronchospasm. In methods for treating asthma disclosed herein, the preferred method of delivering the inventive antagonists is through inhalation There are several different types of devices which use generally different mechanisms and methodologies to produce aerosols for inhalation. The most commonly used device is a metered dose inhaler (MDI) which comprises a drug formulation container with the formulation including a low boiling point propellant. The formulation is held in the container under pressure and a metered dose of formulation is released as an aerosol when the valve on the container is opened. The low boiling point propellant quickly evaporates or "flashes" when the formulation is exposed to atmospheric pressure outside the container. The particles of formulation containing the drug without the propellant are inhaled into the patient's lungs and thereafter migrate into the patient's circulatory system. There are a number of different types of MDI devices. Devices of this type are disclosed in U.S. Pat. No. 5,404,871 issued Apr. 11, 1995 and U.S. Pat. No. 5,364,838 issued Nov. 15, 1994.

Another type of device is the dry powder inhaler (DPI) device. As indicated by the name such devices use formulations of dry powder which powder is blown into an aerosolized cloud via a burst of gas. Typical DPI devices are shown in U.S. Pat. No. 5,775,320 issued Jul. 7, 1998 and U.S. Pat. No. 5,740,794 issued Apr. 21, 1998.

Yet another type of aerosol delivery device forces a formulation through a porous membrane. Formulation moving through the pores breaks up to form small particles which are inhaled by the patient. Devices of this type are shown in U.S. Pat. No. 5,554,646 issued Aug. 13, 1996 and U.S. Pat. No. 5,522,385 issued Jun. 4, 1996.

With respect to inhalable compositions, suitable carrier materials may be in the form of an amorphous powder, a crystalline powder, or a combination of amorphous and crystalline powders. Suitable materials include carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamine hydrochloride, and the like; (d) peptides and proteins, such as aspartame, human serum albumin, gelatin, and the like; (e) alditols, such as mannitol, xylitol, and the like. A preferred group of carriers includes lactose, trehalose, raffinose, maltodextrins, glycine, sodium citrate, tromethamine hydrochloride, human serum albumin, and mannitol.

Such carrier materials may be combined with the inventive agonists or antagonists prior to spray drying, i.e., by adding the carrier material to the buffer solution which is prepared for spray drying. In that way, the carrier material will be formed simultaneously with and as part of the inventive agonist or antagonist particles. Typically, when the carrier is formed by spray drying together with the inventive agonists or antagonists, the inventive agonists or antagonists will be present in each individual particle at a weight percent in the range from 5% to 95%, preferably from 20% to 80%. The remainder of the particle will primarily be carrier material (typically being from 5% to 95%, usually being from 20% to 80% by weight), but will also include buffer(s) and may include other components as described above. The presence of carrier material in the particles which are delivered to the alveolar region of the lung (i.e., those in the requisite size range below 10 μm) has been found not to significantly interfere with systemic absorption of inventive agonists or antagonists.

Alternatively, the carriers may be separately prepared in a dry powder form and combined with the dry powder inventive agonists or antagonists by blending. The separately prepared powder carriers will usually be crystalline (to avoid water absorption), but might in some cases be amorphous or mixtures of crystalline and amorphous. The size of the carrier particles may be selected to improve the flowability of the inventive agonists or antagonists powder, typically being in the range from 25 μm to 100 μm. Carrier particles in this size range will generally not penetrate into the alveolar region of the lung and will often separate from the inventive agonists or antagonists in the delivery device prior to inhalation. Thus, the particles which penetrate into the alveolar region of the lung will consist essentially of inventive agonists or antagonists and buffer. A preferred carrier material is crystalline mannitol having a size in the above-stated range.

The dry powder compositions of the present invention are preferably aerosolized by dispersion in a flowing air or other physiologically acceptable gas stream in a conventional manner. One system suitable for such dispersion is described in copending application Ser. No. 07/910,048, which has been published as WO 93/00951, the full disclosures of which are incorporated herein by reference.

Sterile injectable solutions are prepared by incorporating the compositions and formulations of the invention in the required amount in the appropriate solvent, such as sodium phosphate-buffered saline, followed by filter sterilization. As used herein, "a physiologically acceptable carrier" includes any and all solvents, dispersion media, antibacterial and antifungal agents that are non-toxic to humans, and the like. The use of such media and agents for pharmaceutically active substances is well known in the art. The media or agent must be compatible with maintenance of proper conformation of the inventive protein chains, and its use in the therapeutic compositions. Supplementary active ingredients can also be incorporated into the compositions. A description of exemplary pharmaceutically acceptable carriers and diluents, as well as pharmaceutical formulations, can be found in Remington's Pharmaceutical Sciences, a standard text in this field, and in USP/NF.

The dosage and mode of administration of claimed compositions should be adjusted according to the identity, formulation, route of administration and other relevant characteristics pertaining, as is known, or readily discernable in the art.

2. TNFR25 Agonists as Direct Potentiators of T Cell Polarization and Lung Inflammation TNFR25 and its ligand TL1A were discovered to be direct potentiators of T cell polarization and lung inflammation. The important role of TL1A and TNFR25 in lung disease is supported by the exaggerated lung inflammation observed in agonistic TNFR25-transgenic mice. Over-expression of TNFR25 results in a strong Th2 bias of CD4 cells upon activation. This bias in turn is likely to be responsible for increased lung inflammation in the ovalbumin model.

The inventors observed that in a murine model of asthma, blockade of TNFR25 signaling results in reduced Th2 cytokine production which inhibits lung inflammation. TNFR25 on CD4 cells triggers IL-13 secretion on both Th1 and Th2 polarized cells and TNFR25 signals are needed in NKT-cells that initiate and promote lung inflammation. Chronic IL-13 production, triggered by TNFR25, also is responsible for the sequaelae of chronic lung inflammation including but not restricted to chronic asthma, for airway remodeling and fibrosis. Blockade of TNFR25 signaling on NKT cells by a dominant negative TNFR25 mutant in adoptive transfer experiments abrogates lung inflammation. Blockade of TNFR25 signals such as this would be useful in the treatment of acute and chronic asthma and other lung disorders.

In the chain of events leading to lung inflammation, IL-13 production by NKT cells is an early step (Akbari, O. et al. Nat Med 9, 582-8 (2003)). The critical role for NKT cells in asthma is supported by this study since the adoptive transfer experiments indicated that one of the principal molecular switches used by NKT cells to induce lung inflammation is TNFR25. TNFR25 has the additional ability to modulate incipient effector responses by antigen specific CD4 memory cells through PKC mediated TNFR25 splicing in TCR activated cells. TNFR25 thus acts in the very early phase of the initiation of the memory response in the lung. Therefore, blockade of TNFR25 signaling by anti-TL1A or by other procedures interrupts the cascade of events leading to acute lung inflammation which is thought to be responsible for asthma attacks.

Blockade of TNFR25 was achieved in wild type mice genetically as well as by antibody blockade with the two independent methods giving similar results. Interfering with TNFR25 signals in vivo resulted in diminished IL-13, IL-5 and IL-4 production by antigen restimulated draining bronchial lymph nodes and in suppression of lung inflammation. Importantly, anti TL1A antibody blockade during the phase of airway antigen challenge of primed and Th2 polarized mice was effective in inhibiting lung inflammation indicating a direct role of TNFR25 in the effector phase in the lung.

3. Constitutive TNFR25 Expression on NKT Cells and Inducible Expression on Activated T Cells To study the biological functions of TNFR25 and its cognate ligand TL1A, hamster anti-mouse monoclonal antibodies were generated by standard protocols. To reliably detect the low level of TNFR25 expression by flow cytometry on primary cells it was necessary to develop a triple layer sandwich assay. Without activation TNFR25, was detected at low levels on naïve CD4 T cells and at even lower levels also on CD8 T cells, but not on B cells (FIG. 1a). In addition a subpopulation of CD 11c+ cells expressed TNFR25. NKT cells constitutively expressed relatively high levels of TNFR25, while only a small fraction of CD3 negative NK11+ cells showed TNFR25 expression (FIG. 1a). In the thymus single positive CD4 and CD8 cells expressed TNFR25 similar to peripheral T cells. CD4, CD8 double positive and double negative thymocytes did not express TNFR25 (FIG. 1c).

Figure 2B:
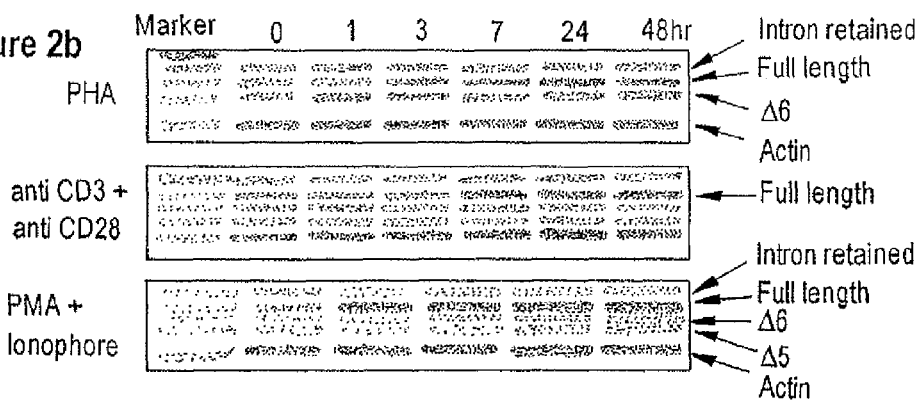
Figure 2C:
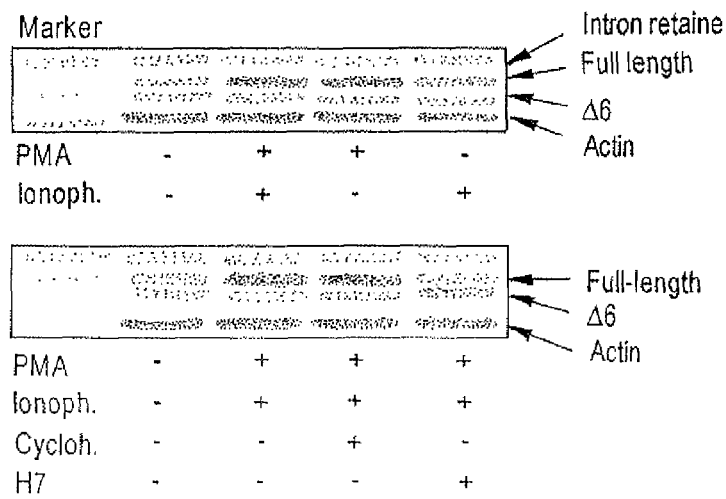

Upon activation of peripheral T cells with anti-CD3 and anti-CD28, TNFR25 expression was upregulated on both CD4+ and CD8+ cells (FIG. 1b). LPS activation of B cells on the other hand did not result in TNFR25 expression. Murine TNFR25 mRNA is constitutively expressed in T cells but randomly spliced similar to human TNFR25 (Screaton, G. R. et al. Proc Natl Acad Sci USA 94, 4615-9. (1997)) (FIG. 2). Increased TNFR25 protein expression on activated T cells was associated with activation induced splicing of full length TNFR25 from randomly spliced TNFR25 mRNA. Activation induced splicing of TNFR25 in T cells was blocked by the chemical inhibitor H7 indicating a role for PKC in splicing (FIG. 2).

The preferential expression of TNFR25 on NKT and activated T cells and its activation induced splicing to full length TNFR25 and rapid increase in surface expression raised the question of the biological function of TNFR25 in the immune system. The ablation of the TNFR25 gene in mice did not reveal a definitive phenotype for TNFR25 deficiency, except for a mild defect in negative selection in the thymus. Hence, the biological effects of T cell-expressed TNFR25-transgenes driven by the CD2 promoter and enhancer were analyzed.

Full length TNFR25 (FL TNFR25, in FIG. 2) and an alternative splice product of TNFR25 lacking exon 5 and 6 ($\Delta 5,6$ TNFR25, FIG. 2) were used for transgenic expression. $\Delta 5,6$ TNFR25 lacks exon 5 and 6 encoding part of the fourth cysteine rich, extracellular domain. It is anchored in the membrane, however, and has a complete intracellular signaling domain like FL TNFR25, and binds TL1A and an agonistic anti TNFR25 antibody (4C12). In addition a dominant negative mutant, DN TNFR25, truncated immediately after the transmembrane domain was expressed as transgene and will be described below.

Figure 3A:
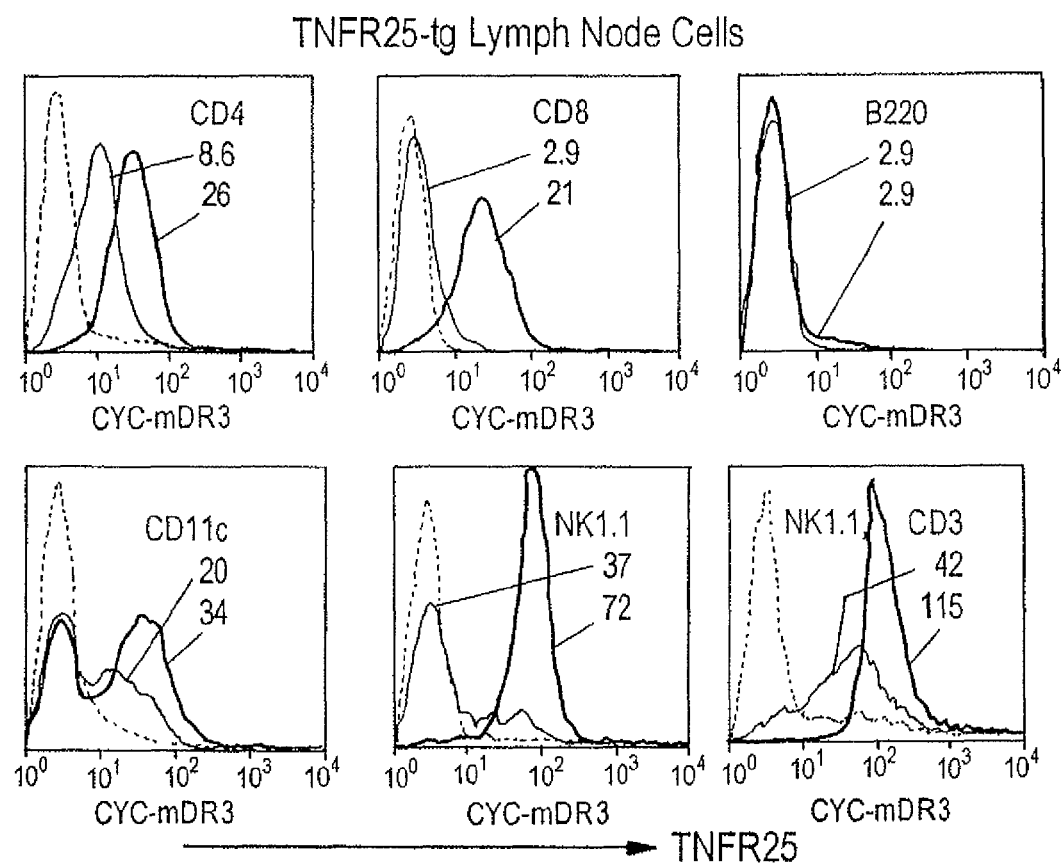
FIG. 3 illustrates expression and function of TNFR25-transgenes under the CD2 promoter and enhancer. 3A depicts expression of TNFR25 in transgenic mice compared to B6 wild-type mice and isotype control. Inguinal lymph node cells were gated on CD4, CD8, B220, CD11c positive cells, or NK1.1 positive and CD3 negative cells or NK1.1/CD3 double positive cells. The corresponding MFI is indicated. The expression profile for FL TNFR25, Δ5,6 TNFR25 and DN TNFR25 were identical. 3B depicts a Western blot of alternatively spliced TNFR25 transfected tumor cells. 50 µg protein from P815 lysates transfected with three splice forms of TNFR25 were loaded and blotted with the anti TNFR25 antibody IOD1. Lane 1: DN TNFR25; lane 2: Δ5,6 TNFR25; lane 3: FL TNFR25. The antibody does not detect Δ5,6 TNFR25 in western blots. 3C illustrates reduced cellularity of the CD4 and CD8 positive cells in FL TNFR25-tg lymph node cells and thymocytes compared to w.t. littermates (n=5) *p<0.05; p<0.01; *p<0.001. 3D depicts impaired activation-induced proliferation of FL and Δ5,6 TNFR25-transgenic cells. Proliferation of purified CD4 or CD8 cells was measured after 3 days of stimulation by thymidine uptake during the last 6 hours. Cells were activated in microtiter plates with immobilized anti CD3 (2 μg/ml) with or without soluble anti CD28 (1 μg/ml) or PMA (10 ng/ml) and ionomycin (400 ng/ml). Recombinant mouse IL-2 was used at 1000 U/ml. 3E illustrates FL TNFR25 and Δ5,6 TNFR25 activate NF-κB NF-κB activation was measured in EL4 cells transfected with FL TNFR25 (upper panel) or with Δ5,6 TNFR25 (lower panel) in response to TNFR25 triggering. Cells were treated with the agonistic TNFR25 antibody 4C12 (5 μg/ml) for 50 min; soluble TL1A was given for 25, 50, or 75 min as indicated in the form of 25% supernatants from TL1A transfected EL4 cells; membrane bound TL1A (MTL1A) was given for 50 min by adding TL1A transfected EL4-cells directly to TNFR25 expressing EL4. Controls received EL4 (untransfected) supernatants for 50 min. Nuclear extracts were prepared and analyzed by EMSA; the arrow indicates activated NF-κB. 3F depicts primary Th2 biased cytokine production by w.t., FL TNFR25 and Δ5,6 TNFR25-transgenic CD4 T cells. CD4 T cells from spleens were purified by negative selection and activated with immobilized anti-CD3 (2 μg/ml) and soluble anti-CD28 (1 μg/ml) for 3 days. Supernatants were collected for cytokine ELISA assays. The figure is representative of three independent experiments. n.s.: not significant; *p<0.05; p<0.01; *p<0.001. 3G illustrates that TNFR25 can costimulate Th1 or Th2 cytokine production. Cytokine production of restimulated FL TNFR25-tg CD4 T cells was determined under non-polarizing (Th neutral), Th1, or Th2 polarizing conditions. CD4 cells were activated with immobilized anti CD3 (2 μg/ml) and soluble anti CD28 (1μ/ml) alone (Th neutral), or combined with IL-12 (5 ng/ml) and anti-IL-4 (20 μg/ml) for Th1 polarization, or combined with IL-4 (10 ng/ml), anti-IFN-γ (10 μg/ml), and anti-IL-12 (10 μg/ml) for Th2 polarization for 4 days. The cells were harvested, washed and replated on anti CD3 for 24 hours and the supernatants collected for cytokine ELISA analysis.
Figure 3B:
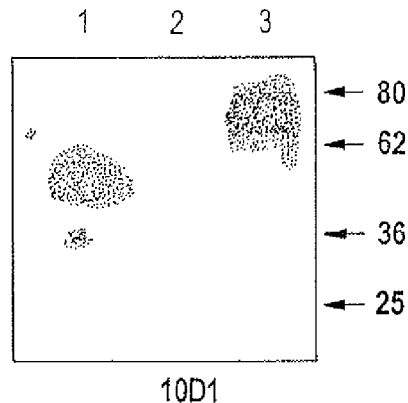
Figure 3C:
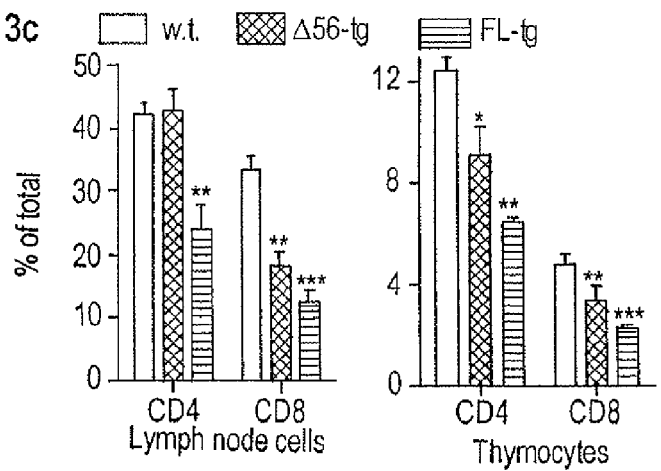
Figure 3D:
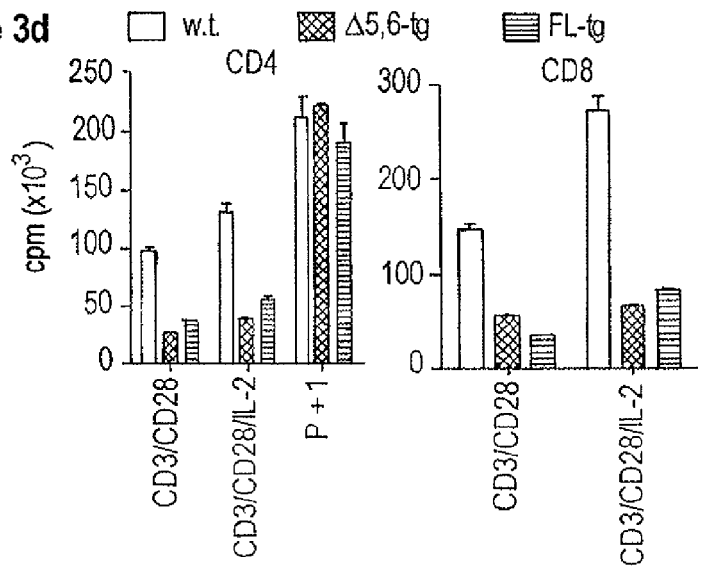

4. Transgenic Over-Expression of TNFR25 Promotes th2 Polarization of CD4 Cells and Mediates Increased Lung Inflammation in the Ovalbumin Model of AHR Four independent founders for each TNFR25 transgene were obtained and analyzed. The CD2 promoter and enhancer supported position independent transgene expression in all founders $\Delta 5,6$ TNFR25, FL TNFR25 and DN TNFR25 revealed high level expression in resting T cells, NKT cells, NK cells and in a subpopulation of CD11c+ cells. B cells did not express the transgene (FIG. 3a). The authenticity of antibody detection by flow cytometry was verified by Western blots of transfected tumor cells (FIG. 3b) and identical Western blot bands were detected on transgenic splenocytes while the endogenous molecule was below the level of detection by Western blot. The $\Delta 5,6$-splice form was not detected by the antibody 10D1 in Western blots (FIG. 3b) indicating that it binds to exon 5 or 6. Transgenic over-expression of FL TNFR25 was associated with diminished numbers of T cells in primary and secondary lymphoid organs compared to non-transgenic litter mates (FIG. 3c); the effect of the $\Delta 5,6$ transgene on cellularity was modest in the thymus and not significant secondary lymphoid organs. The reduced number of T cells in transgenic mice was accompanied by diminished proliferation in response to anti CD3 and CD28 stimulation when comparing equal numbers of purified transgenic with non-transgenic littermate CD4 and CD8 cells (FIG. 3d). Diminished proliferation was seen at all time points from 24 to 72 hours. However, stimulation of TNFR25-tg CD4 or CD8 cells with the phorbolester PMA and the Ca-ionophore ionomycin restored normal proliferation indicating that transgenic cells did not have an intrinsic defect in their ability to proliferate. CD3/CD28 activated TNFR25-tg T cells upregulated CD25 normally but produced only about one half the amount of IL-2 (FIG. 4) compared to littermate controls. Exogenous addition of excess IL-2 did not restore proliferation (FIG. 3d). TNFR25-tg T cells did not undergo increased apoptosis as measured by annexin V staining (FIG. 4) indicating that the proliferative deficit is not due to TNFR25 signals for cell death.

Figure 3E:
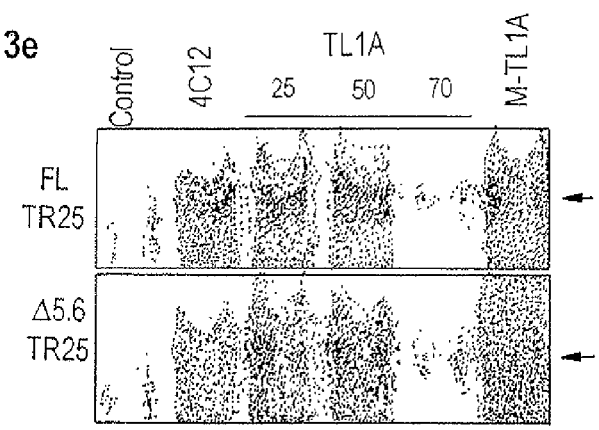

FL and $\Delta 5,6$ TNFR25 transfected EL4 cells were used to compare the signaling properties of the splice variants triggered with soluble TL1A, membrane bound TL (EL4-TL1A) or an agonistic anti TNFR25 antibody (4C12). All three ligands rapidly induced NF-κB activation within 25 min as detected by EMSA (FIG. 3e).

Figure 3F:
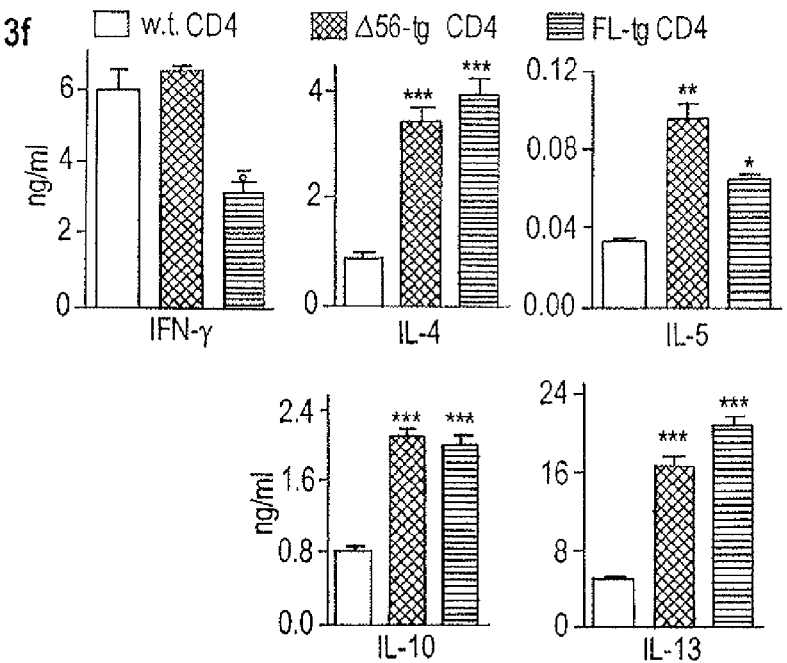

After primary activation with plate bound anti-CD3 and soluble anti-CD28 FL and $\Delta 5,6$ TNFR25 transgenic cells produced significantly increased quantities of Th2 cytokines including IL-4, IL-5, IL-13 and IL-10 when compared to non-transgenic littermates (FIG. 3f). IFN-γ was diminished when FL TNFR25-tg CD4 cells were activated but not with $\Delta 5,6$ TNFR25 transgenes, indicating a subtle difference in the function of the splice variants. Although proliferation of TNFR25-trangenic CD4 cells was diminished, increased Th2 cytokine production was detectable already within 24 hours of activation and continued to increase in the following days, indicating Th2 bias existed prior to activation.

Figure 3G:
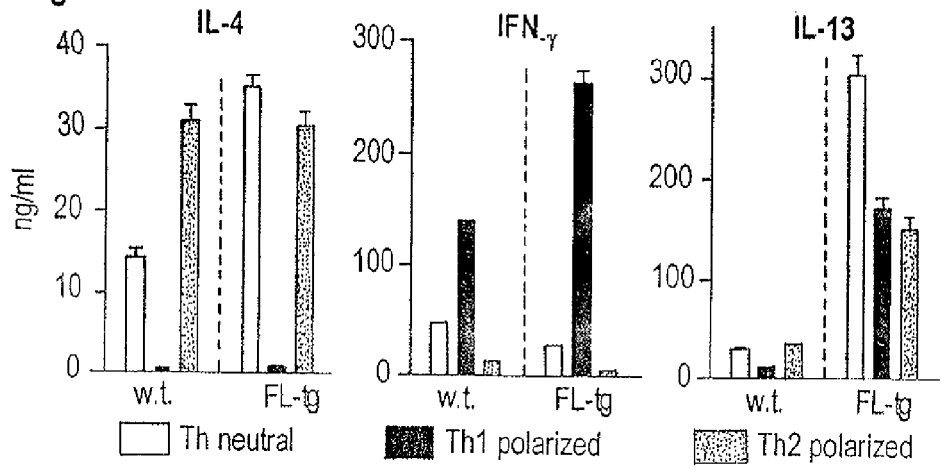

Next it was determined whether the Th2 bias of FL TNFR25-transgenic CD4 cells could be overruled under Th1 polarizing conditions. Under Th neutral conditions TNFR25-tg CD4 cells produced as much IL-4 as w.t. CD4 cells under Th2 polarizing conditions (FIG. 3g). Incubation of FL TNFR25-tg cells under Th2-polarizing conditions had no additional effect on IL-4 or IL-13 production indicating that the cells were already maximally Th2 polarized during primary activation under Th-neutral conditions. However, FL TNFR25-tg CD4 cells could be polarized to Th1 by including in the culture antibodies to IL-4 and adding exogenous IL-12. Under these conditions FL TNFR25-tg cells produced IFN-$\gamma$ at higher levels than Th11-polarized wild type cells (FIG. 3g) indicating that the TNFR25 transgene can also costimulate Th1 cytokines Th1 polarized FL TNFR25-tg CD4 cells, unlike w.t. Th1 cells, also produced IL-13 but only minimal amounts of IL-4. Transgenic over expression of TNFR25 while spontaneously biased towards Th2, nonetheless can costimulate either Th1 or Th2 type cytokine production under appropriate polarizing conditions. In addition TNFR25 signals costimulate IL-13 production under either Th1 or Th2 polarizing conditions.

The spontaneous Th2 bias of TNFR25-tg mice in vivo by immunization and analysis of antibody isotype production was evaluated. In vivo studies were carried out with $\Delta 5,6$ TNFR25-transgenic mice. $\Delta 5,6$-TNFR25 shows the same signaling properties as FL TNFR25 with regard to NF-$\kappa$B induction (FIG. 3e) and induction of apoptosis and generates a similar Th2 biased cytokine profile. However, unlike the FL-transgenic mice, $\Delta 5,6$ transgenic mice have normal CD4 T cell cellularity in lymph nodes (FIG. 3c) and spleens and therefore may more accurately represent TNFR25 function for in vivo experiments.

Figure 5A:
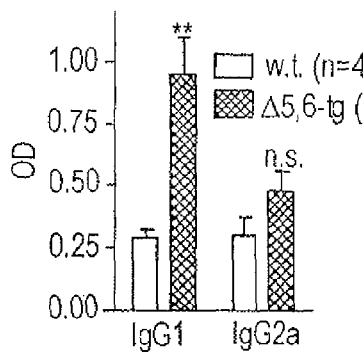
FIG. 5 illustrates that TNFR25 transgenic mice develop a Th2-biased response after in vivo challenge. 5A demonstrates that an antibody-isotype is Th2 biased in immunized TNFR25-tg mice. Mice were immunized intraperitoneally with 100 μg DNP-KLH in sterile PBS without adjuvant. DNP-specific IgG1 and IgG2a antibodies in serum were evaluated by ELISA one week after immunization. High-binding 96-well plates were coated with DNP-BSA at 0.8 μg/ml to detect anti-DNP specific antibodies. Data represent one of three independent experiments. **p<0.01; n.s.: not significant 5B illustrates TNFR25 signals regulate eosinophilia in broncho-alveolar fluid (BALF). Immunization and airway challenge of w.t and Δ5,6 TNFR25-tg mice was done as described in Examples 10-15. Airways were lavaged and the differential cell count obtained from Wright-Giemsa stained cytospins preparations. *: p<0.05; n.s.: not significant 5C depicts increased lung inflammation in TNFR25-tg mice. Lung histology of mice i.p. sensitized and airway challenged with ovalbumin. After bronchial lavage, lungs were removed and fixed in 10% neutral buffered formalin. The lungs were then embedded in paraffin, cut 5 μm thick, and stained with H&E (left panels) or periodic acid-Schiff (PAS, right panels) to detect mucus production. Upper two panels wild type B6 mice; lower panels Δ5,6 TNFR25-tg mice. 5D illustrates that TNFR25 signals control serum IgE levels. Mice were bled on day 0 and three days after the aerosol challenge (day 15). Serum was separated and analyzed by ELISA for ovalbumin specific IgE by sandwich ELISA. Since there is no standard protein available for OVA-specific IgE, results are presented in O.D. units. The figure represents one of three independent experiments. **: p<0.01. 5E depicts increased Th2 cytokine production by bronchial lymph node cells in TNFR25-tg mice. Bronchial lymph nodes were harvested one day after aerosol challenge (day 13) and cells were restimulated in vitro with 100 μg/ml ovalbumin for 4 days. Supernatants were then analyzed for cytokine production by ELISA. This figure is the representative of two independent experiments. *p<0.05; p<0.01; *p<0.001

DNP-KLH immunized TNFR25-tg mice generated increased ratios of antigen specific IgG1/IgG2a antibody compared to non-transgenic litter mates, indicative of an increased Th2 type antibody ratio in vivo (FIG. 5a). Without immunization, IgG1 and IgG2a levels of w.t. and transgenic mice were identical, evidencing that activation is necessary to reveal the Th2 bias.

Figure 5B:
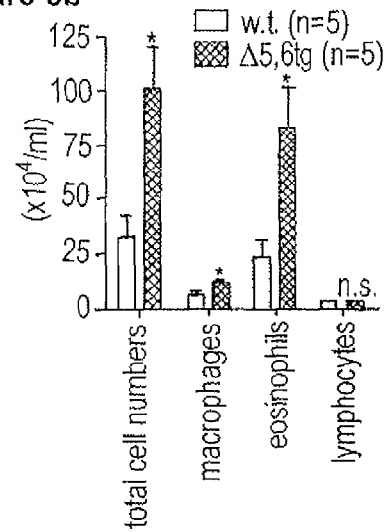
Figure 5C:
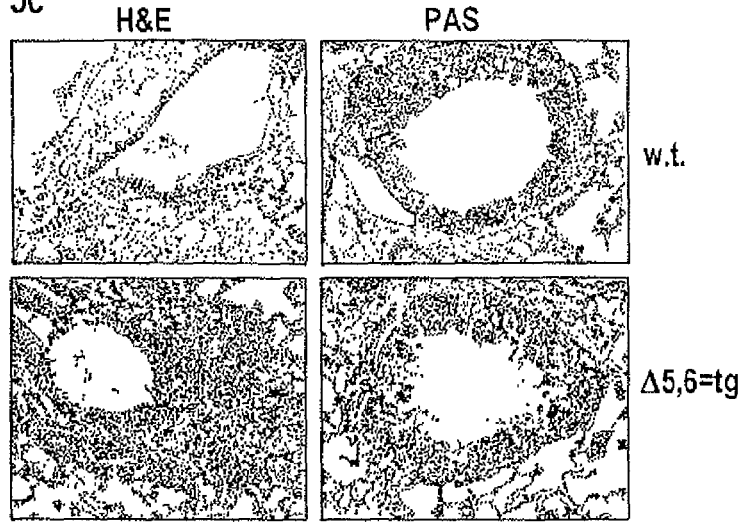
Figure 5D:
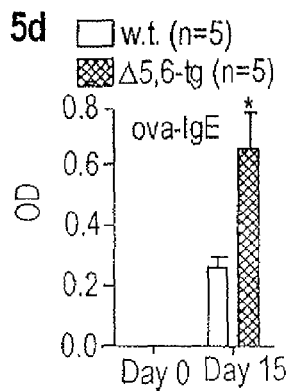
Figure 5E:
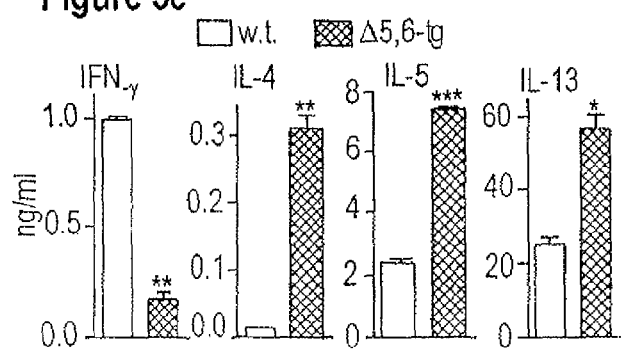

The Th2 bias of TNFR25-tg CD4 cells and their increased IL-13 production suggested that TNFR25 overexpression may predispose to increased allergic lung inflammation characteristic for asthma, as IL-13 is the signature cytokine of that condition (Elias, J. A. et al. Am J Respir Cell Mol Biol 28, 401-4 (2003). This hypothesis was tested using the classical ovalbumin model for experimental lung inflammation in mice. TNFR25-tg B6 mice and w.t. controls were primed i.p. with ovalbumin and alum on day 0 and 5. On day 12 they were airway challenged with aerosolized ovalbumin and analyzed one to three days later. TNFR25-tg mice contained dramatically increased numbers of eosinophils in the broncho-alveolar fluid (BALF, FIG. 5b), associated with increased ovalbumin specific IgE levels in serum (FIG. 5d) and elevated Th2 cytokine production by ovalbumin restimulation of bronchial lymph node cells (FIG. 5e). IFN-$\gamma$ production was diminished in transgenic bronchial lymph node cells compared to w.t. cells. Histopathological analysis of the lungs of TNFR25-tg mice showed massively increased perivascular lung infiltration by eosinophils, increased bronchial mucus production and goblet cell hyperplasia stained with PAS (FIG. 5c) consistent with exacerbation of lung inflammation by TNFR25 over-expression on T cells.

5. Genetic or Antibody Blockade of TNFR25 During Airway Challenge of Primed Mice Blocks Lung Inflammation A dominant negative mutant of TNFR25, DN TNFR25 was made to block TNFR25 signaling during airway challenge, and expressed the construct as transgene under the CD2 promoter and enhancer. The DN TNFR25-transgene lacks the entire intracellular signaling domain but is identical to full length TNFR25 in its transmembrane and extracellular domain.

Figure 4A:
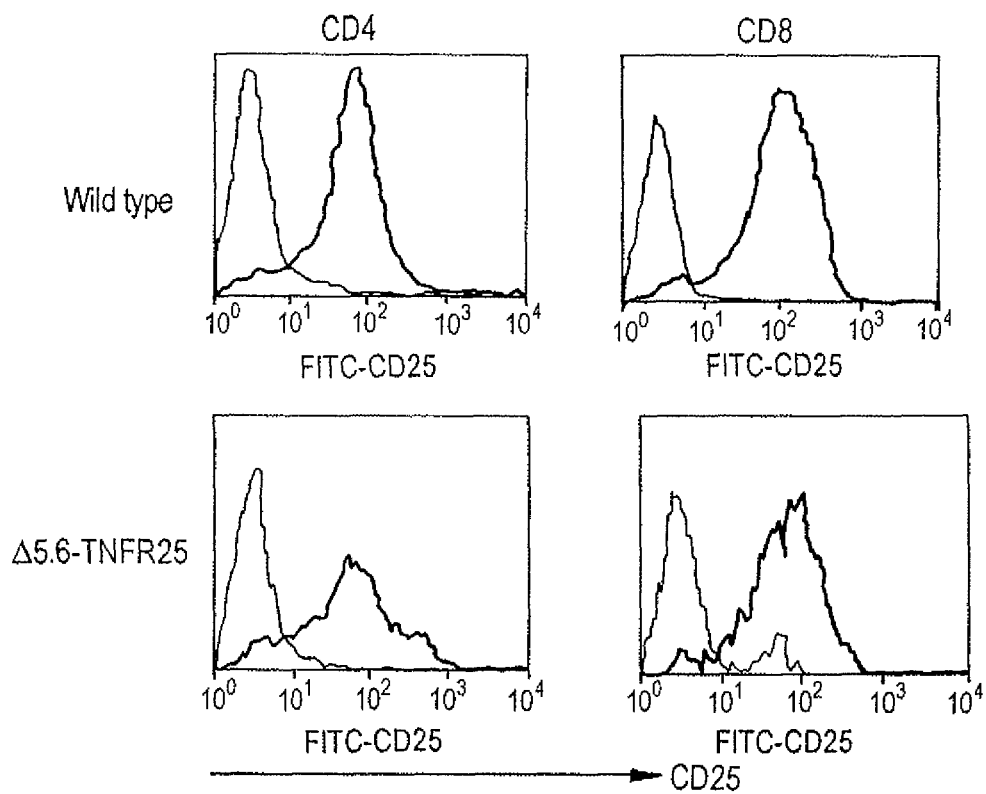
FIG. 4 depicts diminished proliferation of TNFR25-transgenic cells is not due to apoptosis, lack of IL-2 or IL-2 receptor expression. 4A illustrates normal upregulation of IL-2-Ra (CD25) in transgenic CD4 and CD8 cells upon activation. After 72-hour activation with immobilized anti-CD3 and soluble anti-CD28, splenocytes were harvested, washed and stained with anti-CD25-FITC, anti-CD8-PE, and anti-CD4-CY. Upper panels wild type, lower panels Δ5,6 TNFR25-tg cells. 4B demonstrates that transgenic cells do not undergo increased apoptosis upon activation. CD4 cells were activated with immobilized anti-mouse CD3 (2 μg/ml) with soluble anti-mCD28 (1 μg/ml) for three days and stained with Annexin-V-PE and 7-AAD. Annexin-V positive and 7-AAD negative cells represented the apoptotic cells. 4C illustrates Reduced IL-2 production by Δ5,6 TNFR25 transgenic T cells. T cells were purified by negative selection and activated with immobilized anti-CD3 and soluble anti-CD28 for 3 days. Supernatants were analyzed for IL-2 production by ELISA assay; **p=0.0078. 4D illustrates that dominant negative TNFR25-transgenic cells are not Th2 polarized in primary response. CD4 T cells from the spleen were purified by negative selection and activated with immobilized anti-CD3 (2 μg/ml) and soluble anti-CD28 (1 μg/ml) for 3 days. The supernatants were collected for cytokine ELISA assays. The figure is representative of three independent experiments. 4E depicts the same antibody-isotype response of DN TNFR25-transgenic and w.t. mice. Mice were immunized intraperitoneally with 100 μg DNP-KLH in sterile PBS and DNP-specific IgG1 and IgG2a antibodies in serum were evaluated by ELISA three weeks after immunization. High-binding 96-well plates were coated with DNP-BSA at 0.8 μg/ml to detect anti-DNP specific antibodies. Figure represents one of three independent experiments.

Transgenic DN TNFR25 was expressed at identical levels as the agonistic TNFR25 transgenes (FIG. 3a) as determined by flow cytometry. Using surface fluorescence intensity as measure for the number of expressed molecules, a three to four fold molar excess of transgenic TNFR25 expression over endogenous TNFR25 was determined. This level of overexpression of DN TNFR25 silenced the activity of endogenous TNFR25. Primary anti CD3 activation of both w.t. and DN-transgenic CD4 cells stimulates both Th1 and Th2 cytokine secretion (FIG. 4, panel d) Triggering of TNFR25 with an agonistic antibody (4C12) during primary anti CD3 activation of w.t cells costimulates both Th1 and Th2 cytokine production but this costimulatory effect of TNFR25 is blocked by the DN TNFR25 transgene (FIG. 6a), indicating the transgene blocks the function of the endogenous gene. Similarly, the agonistic effect of 4C12 costimulates proliferation of w.t. CD4 cells which was blocked in DN TNFR25-tg CD4 cells (FIG. 6b) indicating that endogenous TNFR25 is silenced. Importantly, the expression of DN TNFR25 on CD4 cells greatly diminished the normally observed, upregulated Th2 cytokine production upon secondary activation of cells that had been primed under Th-neutral conditions (FIG. 6c), indicating that TNFR25 signals strongly promote or are required for Th2 polarization and that these signals are blocked by the DN-transgene. More importantly, DN TNFR25-tg cells could not be Th2 polarized even under Th2 polarizing conditions which were provided by the addition of IL-4 and blocking antibodies to IFN-$\gamma$ and IL-12 (FIG. 6d). Th1 polarization of DNTNFR25-tg CD4 cells on the other hand was not affected even under non-polarizing (Th neutral, ThN) conditions. Thus although TNFR25 costimulates the production of both Th1 and Th2 cytokines in primary activation of CD4 cells, TNFR25 signals appear to be necessary to promote Th2 polarization in vitro. Th1 polarization is independent of TNFR25, but TNFR25 signals in Th1 cells promote IL-13 production (FIG. 3g). The absence of TNFR25 signals in DN TNFR25-tg mice in vivo does not affect the normal IgG1 to IgG2a antibody ratio found in w.t. mice following immunization of DN TNFR25-tg mice with DNP-KLH (FIG. 4).

Figure 6E:
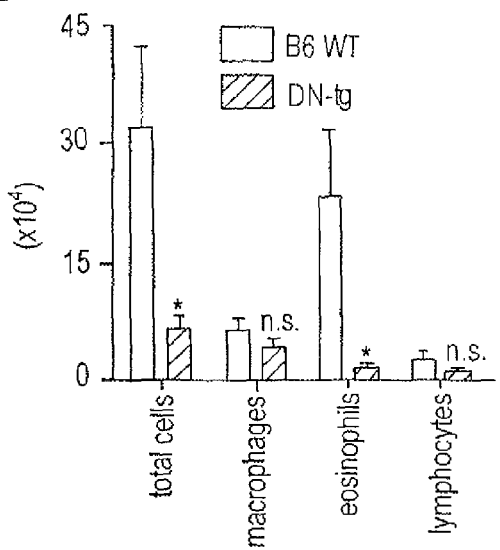
FIG. 6 illustrates that dominant negative TNFR25 interferes with Th2 polarization and lung inflammation 6A illustrates that DN TNFR25 transgene blocks cytokine costimulation by endogenous TNFR25. W.t. and DN TNFR25-tg CD4 cells were stimulated for three days with anti CD3, or with the agonistic anti TNFR25 antibody 4C12 and anti CD3 combined and the supernatants analyzed for cytokines by ELISA. 6B illustrates that DN TNFR25 blocks costimulation of proliferation by endogenous TNFR25. In proliferation assays w.t. and DN TNFR25-tg CD4 cells were activated with anti CD3, with 4C 12, or with the combination of anti CD3 and 4C 12 for 3 days and thymidine incorporation measured during the final 8 hours. 6C illustrates that DN TNFR25-tg CD4 T cells produce diminished Th2 cytokines in secondary activation. W.t. and transgenic CD4 T cells were purified by negative selection and activated with immobilized anti-CD3 (2 μg/ml) and soluble anti-CD28 (1 μg/ml) for 3 days. Cells were then harvested, washed, replated and restimulated with immobilized anti-CD3 (1 μg/ml) for 2 days. The supernatants were collected for cytokine ELISA assay. n.s—not significant; ***p<0.001. 6D depicts that DN TNFR25-tg CD4 T cells resist Th2 polarization in vitro. W.t. and DN TNFR25-tg CD4 cells were purified and activated for four days with anti CD3 and anti CD28 under neutral (ThN) or Th2 polarizing conditions (by adding IL-4 and blocking IFN-γ with antibody). Cells were harvested, washed and replated on anti CD3 for 24 h, supernatants harvested and cytokines analyzed by ELISA. 6E illustrates diminished cellular exudation in BALF in DN TNFR25-tg mice compared to w.t. mice. Mice were primed and then aerosol challenged with ovalbumin according to the standard protocol; n=5; *: p<0.05 6F depicts suppression of lung inflammation in DN TNFR25-tg mice after immunization and airway challenge. Upper panel: Absence of perivascular infiltrates in DN TNFR25-tg mice after antigen aerosol exposure. Lower panel: Absence of mucus over production and goblet cell hyperplasia in DN TNFR25-tg mice. Lung inflammation was induced as in FIG. 5 by ovalbumin immunization and subsequent aerosol exposure. W.t. control mice had typical inflammation as shown in FIG. 5. 6G illustrates suppression of ovalbumin specific IgE production in DN TNFR25-tg mice. Ovalbumin specific IgE in serum was determined by ELISA. **p<0.01 6H depicts suppression of Th2 but not Th1 cytokine production by DN TNFR25 in bronchial lymph nodes. Bronchial lymph nodes were harvested one day after aerosol challenge and cells were restimulated with 1001.tg/ml ovalbumin for 4 days. Supernatants were then analyzed for cytokine production by ELISA. This figure is the representative of two independent experiments. n.d.: not detected; n.s.: not significant; *: p<0.05
Figure 6F:
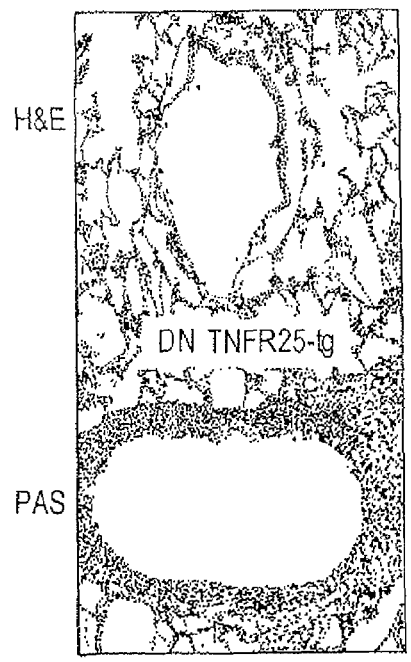
Figure 6G:
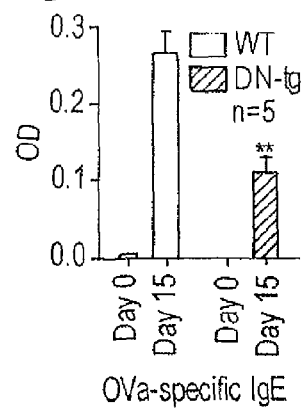
Figure 6H:
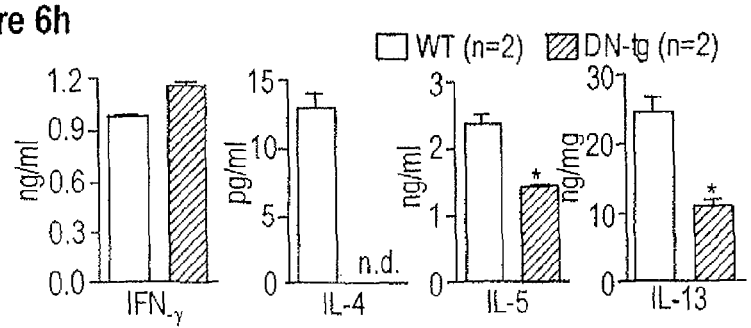

Next, it was determined whether DN TNFR25-tg mice had an altered response in the lung inflammation model. Compared to w.t. mice, DN TNFR25-tg mice upon airway challenge exhibited significantly diminished eosinophilic infiltration in the BALF, absent lung inflammation and diminished IgE production in serum when examined by histopathology and PAS staining (FIG. 6e-g). Restimulating bronchial draining lymph nodes from airway challenged DN TNFR25 tg mice with ovalbumin showed diminished Th2 cytokine production but normal IFN-$\gamma$ production (FIG. 6h). The data suggest that TNFR25 plays a critical role in pulmonary immune responses.

To validate the genetic data of TNFR25 blockade in w.t. mice, monoclonal antibodies to murine TL1A were developed. Using TNFR25 and TL1A transfected cells (FIGS.

Figure 7A:
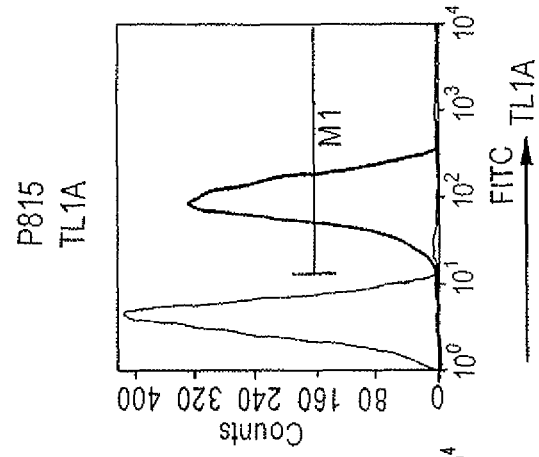
FIG. 7 illustrates that TL1A blocking antibodies abrogate lung inflammation and diminish Th2 cytokine production in the lung. 7A-D depict that anti TL1A antibody L4G6 is a functional antagonist of TL1A. a. P815 transfectants with FL TNFR25, b. with Δ5,6 TNFR25 and c. with TL1A stained by flow cytometry with the appropriate antibodies. d. L4G6 blocks TL1A mediated cytotoxicity of TNFR25 transfected cells. Serially diluted soluble TL1A harvested from supernatants of P815-TL1A transfected cells were mixed with 51Cr-labeled P815-TNFR25 target cells. Different anti-murine TL1A monoclonal antibodies were added into the assay and 51Cr release was analyzed five hours later. 7E illustrates TL1A blocking antibody L4G6 suppresses mucus production and lung inflammation in vivo in wild type C57Bl6 mice. Schema: Schedule of ovalbumin priming, aerosol challenge and administration of blocking antibody (L4G6) or control antibody. Lung histology after PAS staining with control IgG (left) and L4G6-IgG (right). Notice the lack of mucus production in L4G6 treated animals (arrows point to mucus in mice treated with control IgG). 7F demonstrates diminished cellular exudation in BALF in L4G6 treated mice compared to control IgG treated animals. *: p<0.05; : p<0.01; n.s. not significant. 7G illustrates diminished IL-5 and IL-13 production by ovalbumin restimulated bronchial lymph node cells after TL1A blockade with L4G6. p<0.01; ***p<0.001. Experimental details as in FIG. 5. 7H depicts TL1A expression after aerosol challenge on a subpopulation of CD11c positive cells (arrow) in the lung. Bronchial lymph nodes were harvested before and after ova-aerosol challenge, and CD11c cells analyzed for TL1A expression. All other bronchial lymph node cells were TL1A negative. 7I illustrates a lack of TL1A expression on lymphocytes from bronchial lymph node cells of ovalbumin immunized mice after airway challenge. Single cell suspensions were stained in a triple sandwich with anti-TL1A as primary monoclonal antibody. Cells were gated using the respective labeled antibody as population marker and the TL1A histogram displayed. Anti-TL1A; isotype control. 7J illustrates that TL1A is expressed on activated T lymphocytes in vitro. Splenocytes were activated for 24 h with plate bound anti-CD3 or with LPS and then stained with the anti-TL1A triple sandwich as in FIG. 1 and with the population marker as indicated. B cells are TL1A negative even after LPS activation. Gating on the population marker, TL1A expression on activated cells is shown.
Figure 7B:
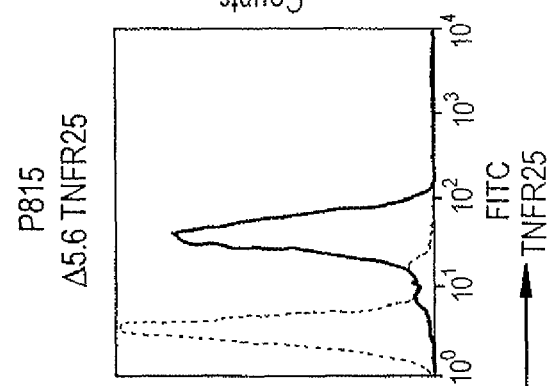
Figure 7C:
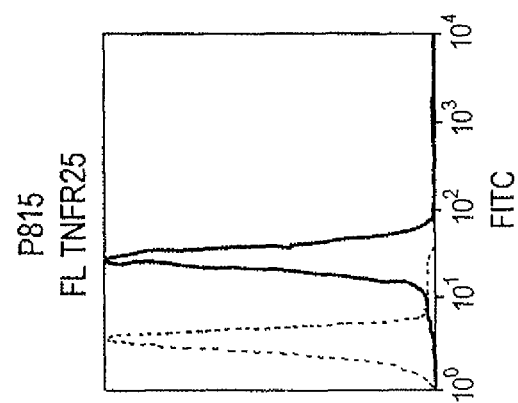

7a,b), TL1A blocking antibodies that abrogated TNFR25 signaling were identified. TL1A transfected cells express TL1A on their surface (FIG. 7c) and secrete TL1A into the supernatant similar to other TNF superfamily members. TL1A containing supernatants caused rapid 51Cr release from FL TNFR25 or Δ5,6 TNFR25 transfected tumor cells through apoptosis as reported previously (Chinnaiyan, A. M. et al. Science 274, 990-2. (1996); Kitson, J. et al. Nature 384, 372-5. (1996); Screaton, G. R. et al. Proc Natl Acad Sci USA 94, 4615-9. (1997); Bodmer, J. L. et al. Immunity 6, 79-88. (1997); Marsters, S. A. et al. Curr Biol 6, 1669-76. (1996); Tan, K. B. et al. Gene 204, 35-46 (1997)). (FIG. 7d). One of the anti-TL1A antibodies, L4G6, completely blocked TL1A mediated lysis of TNFR25-transfected cells, while several other anti-TL1A antibodies either had no effect or mediated only incomplete inhibition of lysis (FIG. 7d). L4G6 antibody therefore was selected for use of in vivo blockade of TL1A to block TNFR25 signaling in genetically unmodified wild type mice. Mice were immunized twice with ovalbumin in alum as usual. One day prior to airway challenge and for the next three days thereafter 50 μg L4G6 was injected i.p. and then the mice were analyzed (FIG. 7e). Controls received the same amount and schedule of hamster IgG. L4G6 administered in this way during and after the period of aerosol challenge phase inhibited eosinophil exudation into BALF, blocked excessive mucus production and diminished the Th2 cytokine production of bronchial lymph node cells upon rechallenge with ovalbumin in vitro (FIG. 7e-g).

Figures 7H, 7I, 7J:
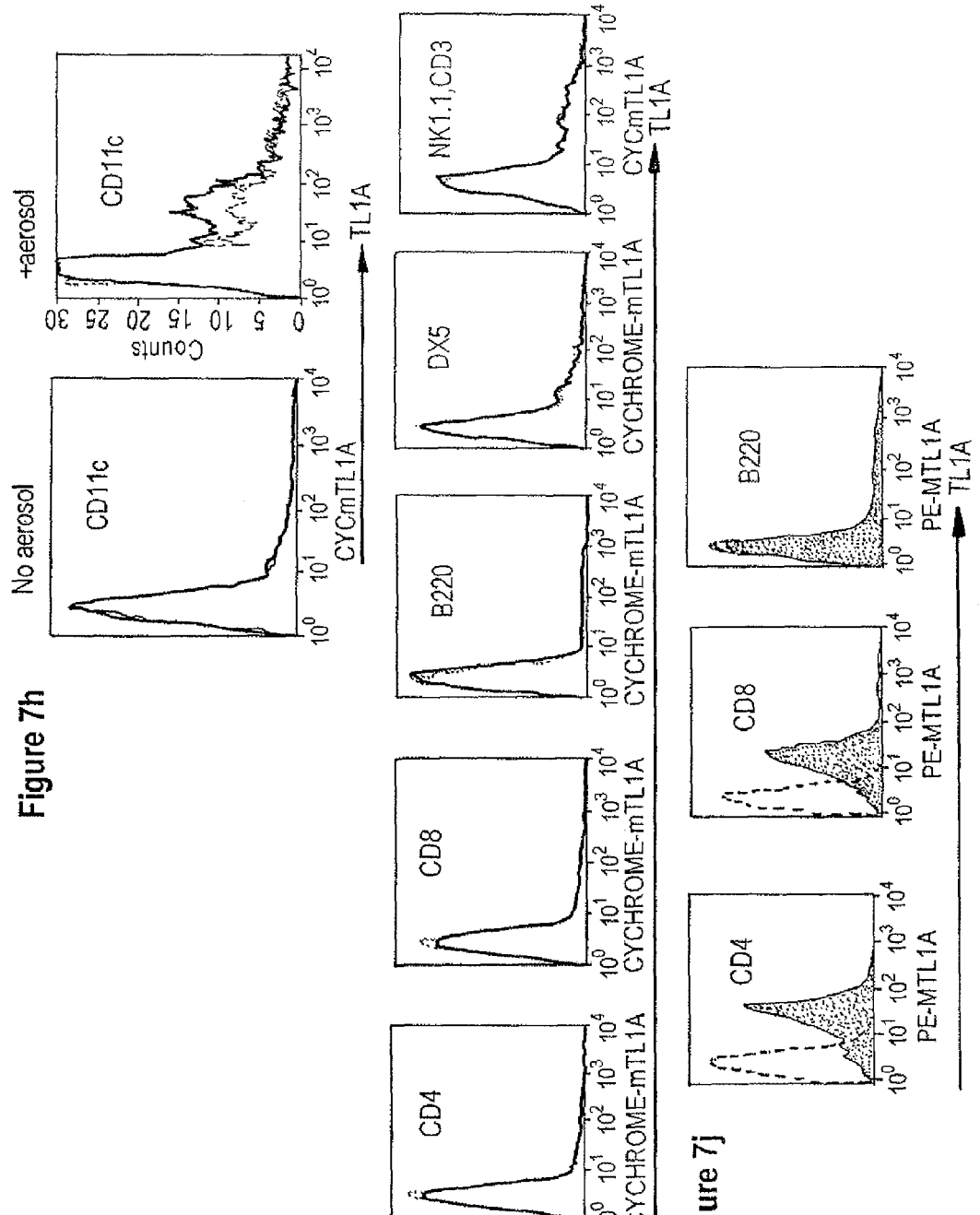

Blockade of lung inflammation by anti-TL1A during aerosol challenge is evidence of TL1A expression in the airways. It was found that modest levels of TL1A are expressed on a subpopulation of CD11c+ cells in bronchial draining lymph nodes after airway challenge but not prior to airway challenge (FIG. 7h). All other cell populations in bronchial lymph nodes were TL1A negative before and after aerosol challenge (FIG. 7i). Inguinal lymph nodes did not express TL1A on CD11c+ cells or any other cell type at any time before or after ovalbumin priming or airway challenge. TL1A expression, however, can be induced in vitro within 24 h on purified CD4+ and CD8+ spleen or lymph node cells by activation with anti-CD3 and anti-CD28 (FIG. 7j). LPS activated, proliferating B cells do not express TL1A (FIG. 7j).

Figure 8:
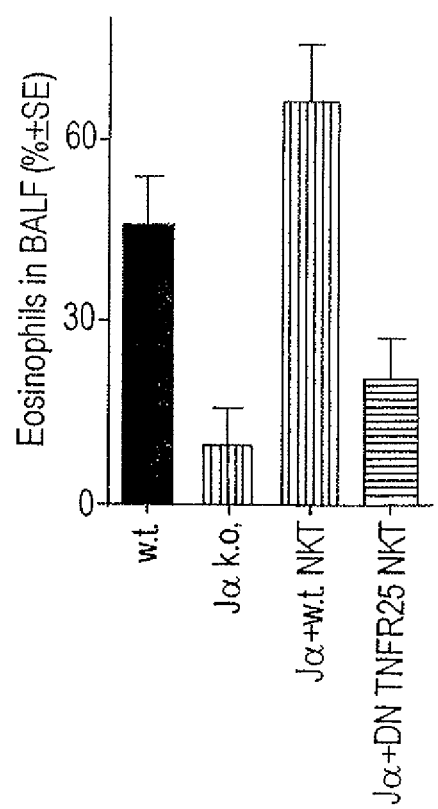
FIG. 8 depicts that TNFR25 signals are required in NKT cells for induction of lung inflammation. NKT deficient Ja18 knock out mice (Cui, J. et al. Science 278, 1623-6 (1997)) were primed with ovalbumin and alum as in the standard protocol in material and methods. On day 11 the mice received by i.v. adoptive transfer 3.1 million partially purified w.t. NKT cells or DN TNFR25-tg NKT cells or PBS as indicated. The mice were aerosolized on day 12 with ovalbumin and on day 14 analyzed. W.t. mice served as positive controls for induction of lung inflammation, Jα 8 k.o. mice were immunized and ovalbumin aerosolized without adoptive cell transfer as negative controls. The data are for four mice in each group in two independent experiments. Jα are NKT deficient mice (Cui, J. et al. Science 278, 1623-6 (1997)).
Figure 9:
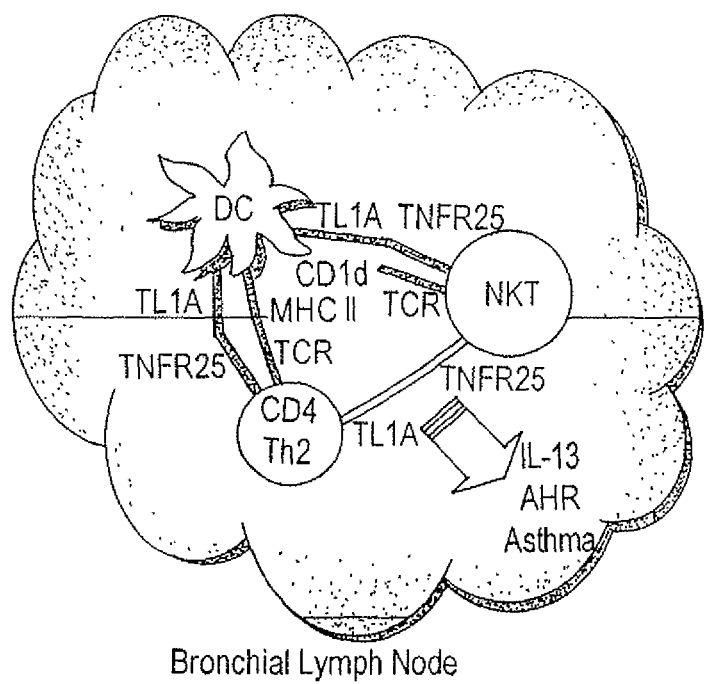
FIG. 9 illustrates a model for TL1A/TNFR25 mediated triggering of NKT cells and Th2 polarized CD4 cells in the lung. The model depicts the potential interaction between TL1A and TNFR25 that may contribute to IL-13 production and induction of AHR. Evidence for the need of IL-13 production by NKT cells has been provided previously (Akbari, O. et al. Nat Med 9, 582-8 (2003)). The present communication shows the need for TNFR25 signals on NKT cells for lung inflammation, the expression of TL1A by CD11c+ cells and the costimulation of CD4 Th2 effectors by TNFR25. Since CD4 effectors can express TL1A it is possible that TL1A/TNFR25 interaction between CD4 and NKT cells provides the molecular link for their synergy in asthma. In addition other lung associated cells may express TL1A and help triggering lung inflammation.

6. DN TNFR25-Transgenic NKT Cells Fail to Support Lung Inflammation in Antigen Primed and Aerosol Challenged NKT Deficient Mice It has been shown that adoptive transfer of w.t. NKT cells to NKT deficient mice restores lung inflammation and airway hyper reactivity in the ovalbumin model and that IL-13 production by NKT cells is required (Akbari, 0. et al. Nat Med 9, 582-8 (2003); Lisbonne, M. et al. J Immunol 171, 1637-41 (2003); Meyer, E. H. et al. Proc Natl Acad Sci USA 103, 2782-7 (2006)). NKT cells have also been implicated in the pathophysiology of asthma patients (Sen, Y. et al. J Immunol 175, 4914-26 (2005). Akbari, 0. et al. N Engl J Med 354, 1117-29 (2006)). To determine whether TNFR25, which is constitutively expressed on NKT cells (FIG. 1a), is involved in triggering lung inflammation, transferred wild type and DN TNFR25-tg NKT cells were adoptively transferred into ovalbumin primed NKT-deficient mice (Cui, J. et al. Science 278, 1623-6 (1997)) (Jα18 k.o.) (FIG. 8). While adoptively transferred w.t. NKT cells restored lung inflammation upon airway antigen challenge, the same number of DN TNFR25-tg NKT cells was unable to do so. The data demonstrate that TNFR25 signals in NKT cells are critical for triggering lung inflammation during airway antigen exposure of sensitized mice.

7. TNFR25 Agonists as Direct Potentiators of Anti-Tumor Immune Responses

Mature dendritic cells carry out an important process referred to as "cross-presentation" that enables them to effectively prime T-cytotoxic cells that are specific for tumor-specific peptides. Tumor antigens are degraded and are presented on MHC Class I proteins to circulating CD8 T cells.

To demonstrate that TNFR25 agonists are effective tumor vaccine BRMs, mice were injected with EG7 tumor cells and OT-I cells. OT-I cells were then observed for clonal expansion. EG7 are EL4 mouse ascites lymphoma lymphoblast cells that have been genetically altered to express ovalbumin, the major protein constituent of chick egg white. Mice were inoculated with EG7 cells and received an adoptive transfer of ovalbumin-specific T-cell receptor transgenic cells (OT-I). OT-I cells act as indicator cells in vivo by responding to the tumor specific ovalbumin antigen. Theoretically, the mouse's dendritic cells present the tumor-specific ovalbumin to and activate the ovalbumin-specific (OT-I) T cells. However, under these circumstances and as is often seen in human tumor vaccine trials, OT-I cells react with anergy to the EG7 tumor cells.

Figure 10:
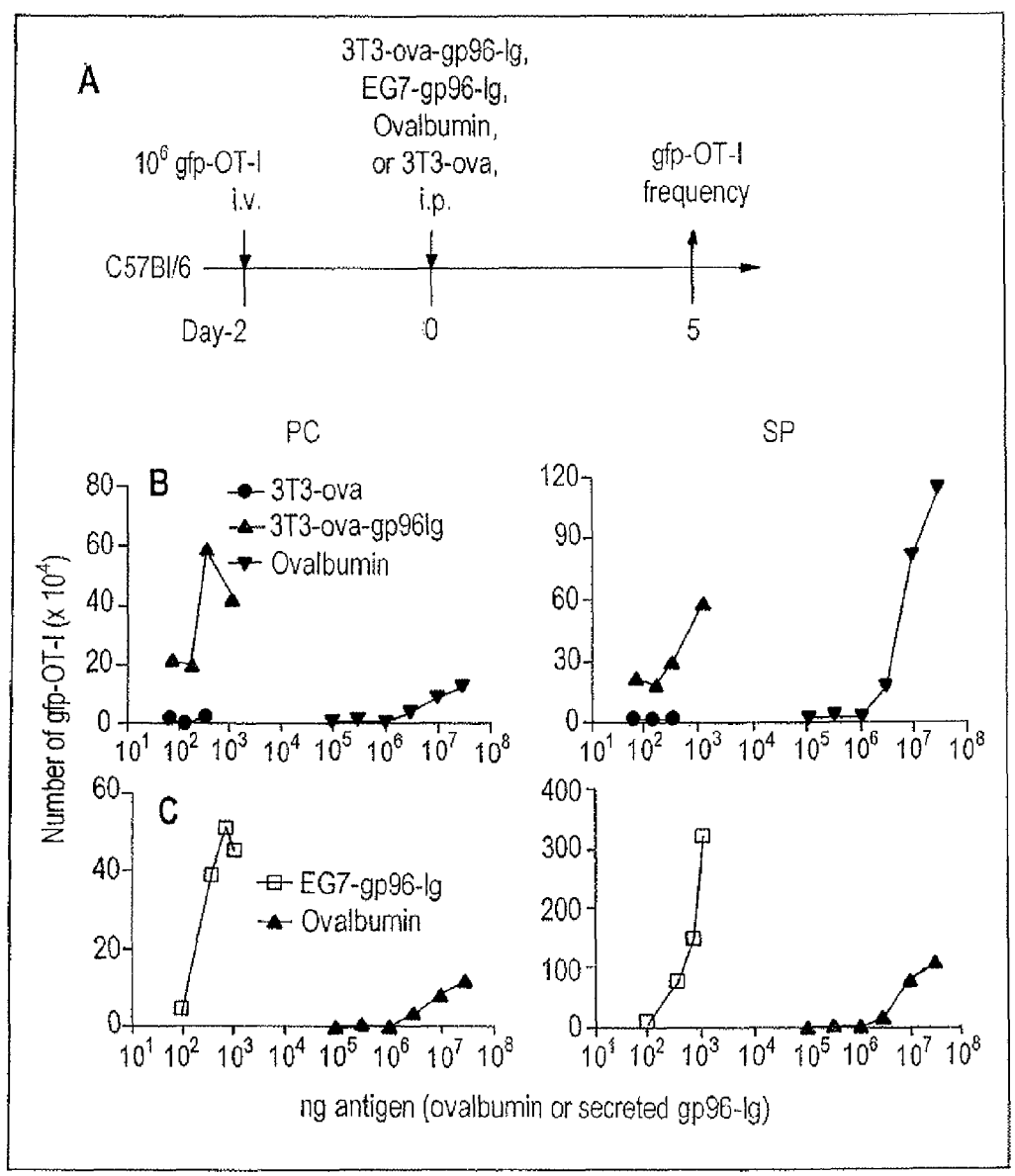
FIG. 10 depicts the results of an experiment in which mice received 1 million-OT-I-gfp i.v. Two days later they were immunized i.p. with the indicated dose of ovalbumin in PBS (blue curve); with EG7-gp96-Ig or 3T3-ova-gp96-Ig—the amount of gp96-Ig (in ng) secreted within 24 h by the number of injected cells is indicated on the abscissa; with 3T3-ova—the amount of ovalbumin secreted within 24 h by the number of injected cells is indicated on the abscissa. After 5 days OT-I expansion was determined by flow cytometry in the peritoneal cavity (PEC) and in the spleen. Frequency of OT-I among CD8 cells was up to 50% in the PEC and up to 8% in the spleen with 3T3-ova-gp96-Ig immunization.

In contrast, co-transfecting EG7 cells with a construct that encodes a secreted version of the heat shock protein gp96 (gp-96-Ig) provided for a tumor secreting gp96Ig and containing ovalbumin as surrogate antigen. Exposure of the CD8 OT-I cells to the secreted chaperone heat shock protein in combination with the tumor specific ovalbumin resulted in an expansion of OT-I from an initial frequency of 0.5% to over 50% of all CD8 cells following primary injection and one boost with gp96Ig secreting. Therefore, cross priming of CD8 cells by gp96-Ig-ovalbumin compared to cross-priming by intact ovalbumin protein is enhanced 10,000 to 1,000,000 fold. See Example 19 and FIGS. 10 and 12. See also Am J Reprod Immunol. 2002 October; 48(4):220-5.

Figure 11:
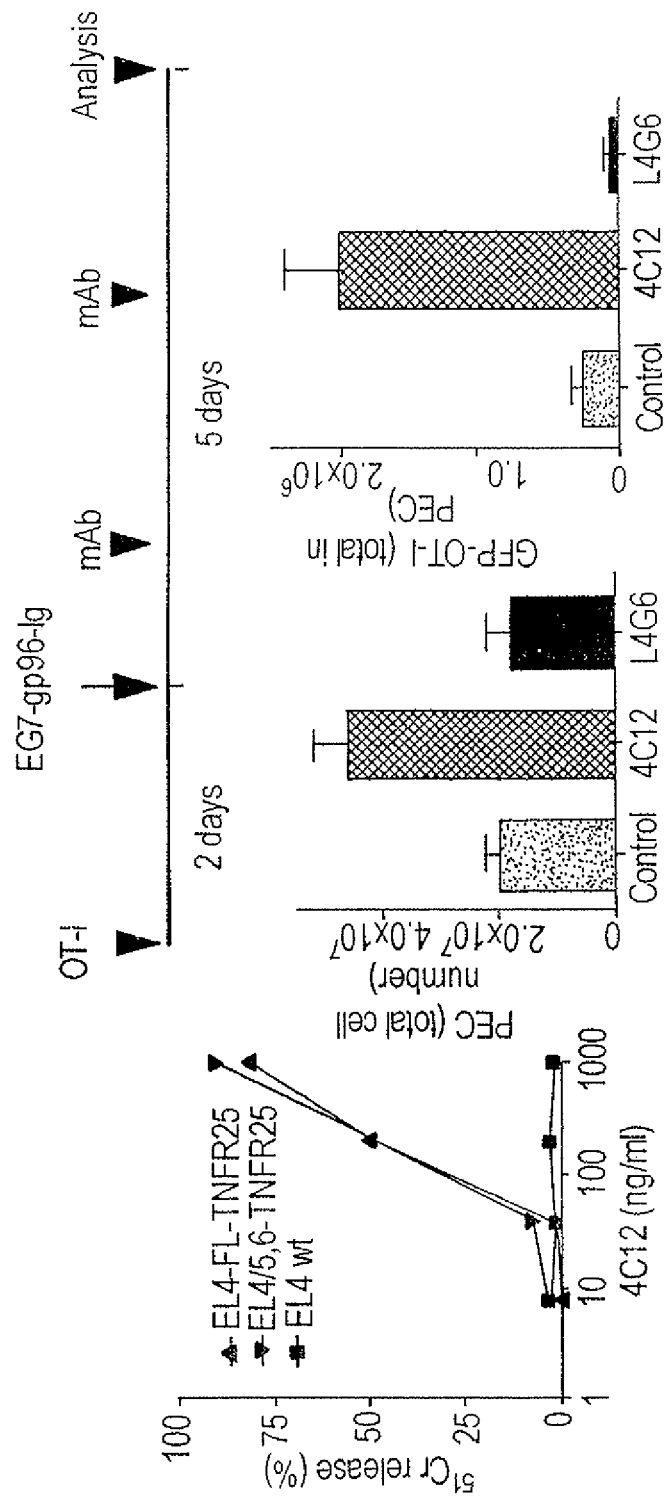
FIG. 11A depicts the results of an experiment in which anti-TNFR25 mAb 4C12 acted agonistically and killed TNFR25 transfected EL4 cells, but not w.t. EL4. In 11B, 50 μg of agonistic 4C12 or antagonistic anti-TL1A L4G6 or control IgG was given i.p. 24 h and 72 h after EG7-gp96-Ig immunization. 4C12 caused 8-10 fold increase of OT-I expansion and doubling of peritoneal exudate cells (n=4 mice per group). Anti TL1A inhibits CD8 expansion.

When OT-I CD8 cells were cross-primed by gp96-Ig-ovalbumin, in the presence of the TNRF25 agonist antibody 4C12, OT-I CD8 expansion increased by an additional 10-fold over a control antibody. However, when OT-I CD8 cells were cross-primed by gp96-Ig-ovalbumin, in the presence of the TL1A blocking antibody L4G6, OT-I CD8 expansion was decreased by an 10-fold over a control antibody. See FIG. 11.

As such, TNFR25 agonists are effective biological response modifiers for tumor vaccines because they boost T cell activation and the cellular immune response to a tumor specific antigen, whereas TNFR25 antagonists blocked or inhibited T cell activation. Therefore, another aspect of the invention relates to methods and therapeutic agents that increase the effectiveness of a tumor vaccine.

Tumor vaccines attempt to the use of elements of the body's natural immune system to fight cancer. Tumor vaccines contain one or more tumor specific antigens and may contain an adjuvant and biological response modifiers. A tumor specific antigen is a polypeptide that is substantially limited to expression in or on tumor cells and which can be used to stimulate an immune response intended to target those tumor cells. Different types of vaccines are used to treat different types of cancer. For an antigenic composition to be useful as a vaccine, an antigenic composition must induce an immune response to the antigen in a cell or tissue. As used herein, an "antigenic composition" may comprise an antigen (e.g, a peptide or polypeptide), a nucleic acid encoding an antigen (e.g, an antigen expression vector), or a cell expressing or presenting an antigen. See U.S. Pub. No. 2003/0185840, which is hereby incorporated by reference in its entirety.

Biologic response modifiers (BRM), which have been shown to upregulate T cell immunity or downregulate suppressor cell activity. Such BRMs include, but are not limited to, Cimetidine (CIM; 1200 mg/d) (Smith/Kline, Pa.); low-dose Cyclophosphamide (CYP; 300 mg/m2) (Johnson/Mead, N.J.), cytokines such as g-interferon, IL-2, or IL-12 or genes encoding proteins involved in immune helper functions, such as B-7.

In one embodiment of this aspect of the invention, the tumor vaccine composition includes a tumor antigenic composition and a TNFR25 agonist. In another embodiment, the TNFR25 agonist is the antibody 4C12. In the preferred embodiment, a TNFR25 agonist is added to a tumor vaccine as a biological response modifier. Even more preferably, the TNFR25 agonist is the antibody 4C12. In another embodiment the tumor vaccine includes an adjuvant.

Tumor vaccine adjuvants may include IL-1, IL-2, IL-4, IL-7, IL-12, gamma-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed Mycobacterium tuberculosis), incomplete Freund's adjuvants and aluminum hydroxide adjuvant.

The preparation of vaccines which contain peptide sequences as active ingredients is generally well understood in the art, as exemplified by U.S. Pat. Nos. 4,608,251; 4,601, 903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

8. TNFR25 Immunotoxins as Indirect Potentiators of Innate Anti-Tumor Immune Responses Many scientists and corporations work on CD4+/CD25+ T regulatory cells (Tregs) because of their immense potential impact on the treatment of many diseases. Although many people are exposed to the same environmental allergens and sensitization to allergens is common, only a fraction of people develop allergic diseases such as asthma. The reason for this is unclear at present but could be related to the presence of efficient regulatory Tregs that suppress airway inflammation in healthy allergen exposed individuals. As such, Tregs are known contribute to the maintenance of peripheral tolerance against self and non-self. However, Tregs have also been documented to impede the body's ability to fight cancer. In those cases, Tregs interfere with the body's tumor-killing immune cells. As such, Tregs function as dedicated suppressor cells and may play a role in preventing tumors, e.g., in squamous cell carcinoma of the head and neck, from being recognized by the immune system. See Br J Cancer, 2005 March 14; 92(5):913-20.

Figure 15:
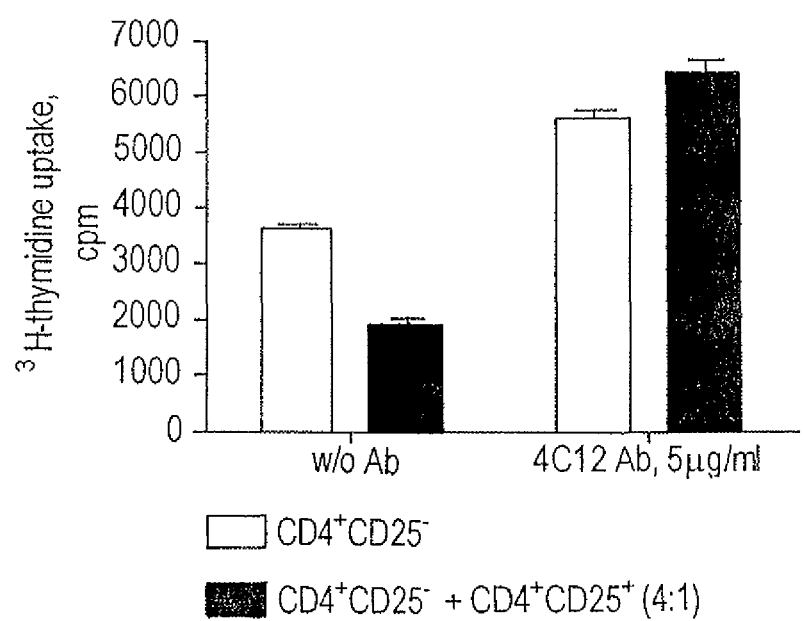
FIG. 15 shows that TNFR25 signals abolish Treg inhibition.

The Inventors have observed that Tregs have properties that suggest that they are activated. Other TNF Receptors have been reported to be expressed on Tregs. GITR is expressed by activated Tregs. Its ligation has been found to abolish the inhibitory activity of Tregs (Nocentini et al., Eur J Immunol. 2005 April; 35(4):1016-22). TNFR25 has many properties that could make it a versatile regulator of Tregs cells. a) TNFR25 protein expression is rapidly up-regulated by PKC induced mRNA splicing; b) Several functional splice versions including a decoy receptor and a dominant negative form allow fine tuning of regulation; c) TL1A expression appears to be highly regulated on Crohn's Disease; in addition TL1A expression on activated lymphocytes allows sensing of lymphocyte density. Finally, they exert their regulatory function at least in part by secreting IL-10 and IL-13, a cytokine triggered by TNFR25 signals. The inventors are the first to note that FoxP3 expressing, CD4+/CD25+ cultured Tregs express inordinately high TNFR25 levels. As such, the Inventors conclude that TNFR25 modulates Treg function and that TNFR25 can be used as a molecular tag to deplete Tregs in vivo. See Example 20. Moreover, TNFR25 angonists abolish Treg Inhibition. See FIG. 15.

Therefore, another aspect of the invention relates to methods and therapeutic agents that are useful in increasing the potency of anti-cancer therapies by depleting a patient of CD4+/CD25+ T regulatory cells (Tregs). In one embodiment of this aspect of the invention, an immunotoxin used to deplete Tregs. In this embodiment, the immunotoxin has an antigen binding portion that is specific for TNFR25; and is conjugated to a toxic agent. In an alternate embodiment, the patient is provided with soluble TL1A conjugated to a toxic agent. Yet another embodiment relates to a chemotherapeutic composition having a chemotherapeutic agent and a TNFR25-specific immunotoxin. Still another embodiment relates to a chemotherapeutic composition having a chemotherapeutic agent and a TL1A conjugated to a toxic agent.

Another aspect of the invention relates to methods and therapeutic agents that are useful in increasing the potency of anti-cancer therapies by providing a patient with TNFR25 agonists reduce inhibition mediated by CD4+/CD25+ T regulatory cells (Tregs).

9. TNFR25 Agonists as Anti-Inflammatory Agents

Using a dominant negative form of TNFR25 (DN-TNFR25) lacking the intracellular death domain and an alternatively spliced form of TNFR25 (delta 5,6-TNFR25) lacking exon 5 and 6 encoding the fourth extra-cellular cysteine rich domain, the Inventors found that TNFR25 function is required to restore homeostatic balance after a mucosal insult. Specifically, the inventors transgenically expressed a dominant negative form of TNFR25 (DN-TNFR25) under the CD2 promoter in mice. The mice were given dextran sodium sulfate (DSS) to induce colitis as a model for human Crohn's disease. Wild type C57Bl/6 mice developed colitis and diarrhea and lost weight after 5 days of drinking water with 2% DSS. However, if restored to normal water, wild type mice recovered within a week and regained weight, whereas DN-TNFR25-tg expressing mice acquired disease in a similar manner to wild type mice but diarrhea appeared more severe. Additionally, restoration to normal water did not result in their recovery. Instead all DN-TNFR-tg expressing mice continued to loose weight and died within the second week. Mice expressing functional transgenes of TNFR25 (full length TNFR25 or a splice version Δ5,6-TNFR25) recovered in a manner similar to wild type mice. See Examples 21 and 22 and FIG. 14.

Current treatment of Crohn's disease uses anti inflammatory agents, immunosuppressives, and TNF inhibitors. All these are symptomatic. Stimulating TNFR25 signaling moves one step up in the pathogenetic chain of events. Activated TNFR25 stimulates IL-10 and IL-13 production, which, in turn, stimulates TGF-beta production resulting in restoration of homeostasis. Such a treatment is curative or approaching cure.

Therefore, another aspect of the invention relates to a method of treating inflammatory bowel disease in a patient by administering to a patient a therapeutic amount of a TNFR25 agonist. Another embodiment relates to a method of treating inflammatory bowel disease in a patient by raising IL-10 levels in the mucosal areas in the intestine. In another embodiment, the TNFR25 agonist is the antibody 4C12. In a further embodiment, the TNFR25 agonist is the a soluble form of TL1A. In the preferred embodiment, the inflammatory bowel disease is Crohn's disease.

Given this anti-inflammatory activity of TNFR25 agonists, it is another aspect of the invention to provide methods and therapeutic agents to a patient requiring reduction of inflammation. In one embodiment, a patient is provided a composition containing a TNFR25 agonist to decrease inflammation and promote healing. In one embodiment, a patient is provided with a composition containing the TNFR25 agonist 4C12. Such embodiments are useful for alleviating the symptoms of disorders mediated by chronic inflammatory responses at the cellular level, including cardiovascular diseases (e.g., atherosclerosis), autoimmune diseases including systemic lupus erythematosis (SLE), multiple sclerosis (MS), diabetes (especially type I diabetes), ankylosing spondulitis, arthritis (particularly rheumatoid arthritis), asthma and allergy, bone resorptive disorders, opthalmological disorders including retinopathies, and fibrotic diseases.

10. TNFR25 Antagonists as Immunosuppressives

Many organs and tissues are now routinely transplanted from one human to another. Except for the rare cases where the donor and recipient are monozygotic "identical" twins, such grafts are called allografts. Tissue matching for the transplantation of tissues from one individual to another is critical because a tissue recipient will mount a strong humoral and cellular immune reaction against all non-self proteins. Tissue typing involves identifying MHC antigens on both donor and recipient cells and using donor cells with as many MHC alleles identical to those of the recipient as possible. Matching MHC Class I (especially HLA-B) and Class II HLA-DR alleles is more important for successful transplantation than matching other MHC antigens; and matching MHC is more important than matching minor histocompatibility antigens.

HLA matching improves graft survival but does not prevent rejection, even in MHC-identical siblings (except for identical twins). Allogeneic MHC is recognized by either CD8 T cells (Class I) or CD4 T cells (Class II); up to 10% of T cells can recognize a given allogeneic MHC because it resembles self MHC+foreign peptide.

Improved success in transplantation is due to growing technical expertise, increasing availability of transplant centers to do HLA matching and minimize organ delivery time, and the increased availability of immunosuppressive drugs (cyclosporin and tacrolimus) that block T cell activation to alloantigens. Still problematic are shortages of organs, the ability of existing disease to destroy the transplanted organ (diabetes and HBV infection are two examples), side effects of immunosuppressive drugs and high cost.

Given the major side effects associated with current immunosuppressives that block T cell activation and the observation that TNFR25 antagonists such as TL1A blocking antibody L4G6, make effective inhibitors of cognate CD8 T cell clonal expansion (see FIG. 11, Example 19), another aspect of the invention involves the use of TNFR25 antagonists for the facilitation of tissue transplantation to prevent tissue rejection. In one embodiment, TNFR25 antagonists are provided to a transplant recipient to suppress the clonal expansion of CD8 T cells that carry alloantigen-specific T cell receptors (TCRs) and to relieve suppression of T-regs by TNFR25. In another embodiment, TNFR25 antagonists are provided to a transplant recipient in combination with an immunosuppressive agent.

EXAMPLES

Example 1

Media and Reagents

Cells were cultured in Iscove's Modified Dulbecco's Minimal Essential Medium (Invitrogen) supplemented with 10% heat-inactivated FBS (Invitrogen), 10 µg/ml gentamycin (Invitrogen), and 50 µM β-mercapto-ethanol (Bio-Rad). Monoclonal anti-mouse CD3 and anti-human CD3 were purified from culture supernatants of the 2C11 and the OKT3 cell lines, respectively (ATCC, Manassas, Va.). Monoclonal anti-mouse CD28 and anti-human CD28 were purchased from eBioscience (San Diego, Calif.). ConA, PHA, and LPS were purchased from Sigma (St. Louis, Mo.). Recombinant murine IL-2 was from BioSource International (Camarillo, Calif.). PMA, ionomycin, H7, and cycloheximide were purchased from Calbiochem (San Diego, Calif.).

Directly conjugated monoclonal antibodies, including FITC-CD4, Cychrome-CD4, PE-CD8a, Cychrome-CD8a, FITC-B220, PE-B220, FITC-CD25, PE-CD11c, PEDX5, FITC-CD3, PE-NK1.1, PE-Annexin V and 7-AAD were purchased from BD/PharMingen (San Diego, Calif.). Hamster IgG control was purchased from eBioscience.

Example 2

Generation of Monoclonal Antibodies Against mTNFR25 and mTL1A

Armenian hamsters were immunized intraperitoneally three times biweekly with 50 µg of mTNFR25-Ig or mTL1A-MBP (maltose binding protein) in Freund's adjuvant. Three days prior to the fusion, hamsters were boosted with 50 µg of the respective proteins intravenously. Hamster splenocytes were fused with the murine myeloma SP20 with PEG and then plated in methylcellulose-based medium for two weeks using ClonaCell-HY kit (StemCell Technologies Inc., BC, Canada). One thousand colonies were picked and analyzed by ELISA in plates coated with the immunizing fusion protein or control protein-Ig fusion protein. Supernatants from positive clones were tested for the ability to detect mTNFR25 isoforms in transfected cells by flow cytometry and western blotting. Antibodies were purified from a Nutridoma-SP (Roche, Indianapolis, Ind.) supernatant on a protein G column, dialyzed into PBS and filter sterilized.

Example 3

Flow Cytometric Analysis for the Expression of mTNFR25 and mTL1A

Single cell suspensions were prepared from lymphoid organs indicated in the individual experiment. Prior to staining, cells were treated with purified anti-mouse CD16/CD32 (Fc-γIII/II receptor; BD) and purified human IgG (Jackson ImmunoResearch, West Grove, Pa.) to block non-specific binding to FcRs. Cells were stained with Armenian hamster anti-mouse TNFR25 or anti-mouse TL1A for 30 minutes at 4° C. Cells were washed in FACS buffer (PBS containing 0.5% BSA and 2 mM EDTA) and then stained with biotin-labeled goat anti-Armenian hamster IgG (Jackson ImmunoResearch) for 30 minutes at 4° C. Cells were washed and then stained with Streptavidin-PE or Streptavidin-Cychrome (BD) for 30 minutes at 4° C. Cells were washed and then stained with directly conjugated cell surface markers for distinct cell populations. Samples were analyzed using a Becton Dickinson FACS LSR instrument and CELLQuest™ software.

Example 4

RT-PCR

Identification of splice forms of mTNFR25: Messenger RNA was extracted from murine cell lines or tissues with the Micro Fast-Track kit (Invitrogen, Carlsbad, Calif.) and cDNA was reverse transcribed using the Superscript II kit (Invitrogen). RT-PCR products were subcloned into the PCR II vector using the TOPO cloning kit (Invitrogen) and were confirmed as splice forms of mTNFR25 by DNA sequencing. For splicing analysis of murine TNFR25 the following primers were used. Upstream primer, exon 2: CAG TGA GTC CCA GAA GAG GT (SEQ ID NO: 8); downstream primer, exon 7: GGA TAG CCC CAA AAA GGA AC (SEQ ID NO: 9); upstream primer, exon 7: TCC TTT TTG GGG CTA TCC TG (SEQ ID NO: 10); downstream primer, exon 10: GGT ATT TCT CCA TGA CGC TT (SEQ ID NO: 11).

Activation-induced alternative splicing of human TNFR25 was analyzed because in the mouse the PCR products of different splice forms were more difficult to distinguish on agarose gels but appeared similar to human splice forms. The following PCR primers were used. Upstream exon 4: TTC ACC CTT CTA CTG CCA AC (SEQ ID NO: 12); downstream, exon 7: TAA CCA GGG GCT TGT GAG GC (SEQ ID NO: 13). Human peripheral blood mononuclear cells were isolated from healthy donors by Ficoll Hypaque density gradient centrifugation. Five million cells per sample were activated with PHA (5 µg/ml), or immobilized anti-CD3 (OKT3, 5 µg/ml) and anti-CD28 (1 µg/ml), or PMA (10 ng/ml) and ionomycin (400 ng/ml). The cells were harvested at the indicated time points and mRNA was extracted and converted to cDNA using the Invitrogen kit. Human β-actin was used as internal control. Quantitation of PCR products was done with the aid of Molecular Analyst software (BioRad).

Example 5

Generation of Transgenic Mice

Murine TNFR25 constructs were cloned under the human CD2 promoter and local control region (gift from Dr. A. Singer, NIH) using the restriction endonuclease sites EcoR I and Sal I. Three mTNFR25 constructs were generated by PCR using a proofreading enzyme. The constructs were the full length molecule of murine TNFR25 (FL TNFR25), the TNFR25 splice variant lacking the 5th and 6th exon (Δ5,6 TNFR25), and the dominant negative version of TNFR25 (DN TNFR25, as 1-234) terminating at the end of the transmembrane domain and lacking the entire intracellular domain. The sequence of the PCR products was confirmed by sequencing. Microinjections of DNA into the fertilized eggs were performed by the transgenic facility at the University of Miami, School of Medicine. Potential founders were screened by PCR of DNA from tail biopsies. The primer pair was located upstream and downstream of the cloning sites, therefore the same primer pair was used for all the mTNFR25 transgenes. The upstream primer is 5' CGC TCT TGC TCT CTG TGT ATG 3' (SEQ ID NO: 14) and the downstream primer is 5' CTG CCA GCC CTC TTC CAT C 3' (SEQ ID NO: 15). Transgenic mice were bred into the C57BL/6J background by serially mating hemizygous transgenic animals with wild-type C57BL/6J (Jackson Laboratories, Bar Harbor, Me.). All mice were used at 6-12 weeks of age and were maintained in pathogen-free facilities. The University of Miami Animal Care and Use Committee approved all animal use procedures.

Example 6

Nuclear Extract Preparation and Electrophoretic Mobility Shift Assays for NFIκB Activation One hundred and seven of EL4-Δ5,6 TNFR25 or EL4-FL TNFR25 cells were treated with soluble or membrane bound TL1A or with the TNFR25 agonistic antibody 4C12 as indicated in the figure legends and then collected by centrifugation at 800 g for 5 min. Nuclear extracts were isolated using a minipreparation protocol and subjected to EMSA as described (Harhaj, E. W. et al. Virology 333, 145-58 (2005). Nuclear extracts (6 µg) were incubated at room temperature for 20 min with a 32P-labeled high-affinity κB probe, followed by resolving the DNA-protein complexes on native 5% polyacrylamide gels.

Example 7

T Cell Proliferation Assay

Splenocytes were plated in triplicate at $1 \times 10^5$ cells/well in 96-well flat-bottom plates. Cells were activated with immobilized anti-CD3 (2 µg/ml) with or without soluble anti-CD28 (1 µg/ml), or with ConA (5 µg/ml) or with PMA (1 µg/ml) and ionomycin (400 ng/ml). For T cell proliferation, purified CD4 T cells at $1 \times 10^5$ cells/well or CD8 T cells at $5 \times 10^4$ cells/well were stimulated with coated anti-CD3 (2 µg/ml) and soluble anti-CD28 (1 µg/ml). Recombinant mIL-2 was added to the culture at 1000 U/ml in indicated experiments. Cells were cultured for 72 hr and pulsed for the last 6 hours of incubation with 1 µCi/well of 3H-thymidine (Perkin Elmer, Boston, Mass.), and thymidine incorporation was quantitated using a scintillation counter.

Murine CD4 or CD8 or T cells were purified from splenocytes and/or lymph nodes by negative selection using Spin-Sep kit (StemCell Technology Inc.) according to the manufacturer's protocol. The purity was routinely around 90%-96% examined by FACS analysis.

Example 8

Immunization of Mice with DNP-KLH, Antibody Isotype Determination, and Cytokine ELISA Adult (6-10 wk old) transgenic and wt mice were immunized intraperitoneally with 100 µg DNP-conjugated keyhole limpet hemocyanin (DNP-KLH) (CalBiochem). One week and three weeks after immunization, mice were bled and serum was separated for analysis of anti-DNP specific IgG1, IgE, and IgG2a antibodies by ELISA according to manufacturer's protocol (BD). Sera from individual animals were absorbed to 96-well plates coated with 0.8 µg/ml DNP-albumin (DNP-BSA) (CalBiochem) and the isotype of bound antibody determine by ELISA.

To examine the cytokine production in the supernatants of cell cultures, sandwich ELISAs were performed per the manufacturer's instructions. Antibody pairs from BD were used for IL-2, IFN-γ, and IL-4 analysis. Reagents for IL-13 ELISA were purchased from R&D Systems (Minneapolis, Minn.) and reagents for IL-5 and IL-10 ELISA were purchased from eBioscience.

Example 9

In Vitro Polarization CD4 T Cells into Th1 or Th2 Cells

CD4 T cells were purified by negative selection as mentioned above. CD4 T cells were activated with immobilized anti-mCD3 (2 μg/ml) and soluble anti-mCD28 (1 μg/ml) alone, or in the presence of IL-12 (10 ng/ml) and anti-mIL-4 (20 μg/ml) for Th1 differentiation, or with IL-4 (10 ng/ml), anti-mIFN-γ (10 μg/ml), and anti-mIL-12 (10 μg/ml) for 7 days. The cells were harvested, washed and replated at 1×105 cells per well and restimulated with immobilized anti-CD3. After 24 hours the supernatants were harvested and evaluated for cytokine production by ELISA.

Example 10

Immunization Protocols for the Murine Model of Allergic Asthma

DN TNFR25-tg (encoded by SEQ ID NO: 16), Δ5,6 TNFR25-tg, and FL TNFR25-tg mice generated as described before and backcrossed at least seven generations into the C57BL/6J background were compared with wild-type C57BL/6J mice purchased from National Cancer Institution (Frederick, Md.). Mice were sensitized by intraperitoneal injection of 66 μg ovalbumin (crystallized chicken egg albumin, grade V; Sigma) absorbed to 6.6 mg aluminum potassium sulfate (alum; Sigma) in 200 μl PBS on day 0. On day 5, mice were boosted intraperitoneally with the same dose of ovalbumin in alum. On day 12, mice were aerosol challenged with 0.5% ovalbumin in PBS for one hour using an Ultrasonic Nebulizer (MABIS Healthcare Inc., Lake Forest, Ill.). Mice were assessed for allergic inflammation of the lungs three days after the single aerosol exposure. Mice were sacrificed by inhalation of CO2. After cannulation of the trachea the lung was lavaged 4 times with 1 ml of PBS. Cells recovered from the BAL fluid were counted and used for cytospin preparations (50,000 cells or fewer/slide). >200 cells were counted for each cytospin slide stained with Wright-Giemsa stain (Sigma) to determine differential cell counts for macrophages, eosinophils, lymphocytes, and neutrophils.

Example 11

Lung Histology

Lungs were removed from mice after the bronchial lavage procedure and fixed in 10% neutral buffered formalin. Samples were submitted to the Histopathology Core of the Sylvester Cancer Center at the University of Miami School of Medicine where specimens were embedded, sectioned, and stained with haematoxylin and eosin. Sections were also stained with periodic acid-Schiff (PAS) to determine mucus production.

Example 12

ELISA for Serum Total IgE and Ovalbumin-Specific Ig

Mice were bled before sensitization (day 0), 3 days after aerosol challenge (day 15) and in some experiments one day before aerosol challenge (day 11). The total IgE level was quantitated by ELISA according to the manufacturer's protocol (BD). Ovalbumin specific IgE was determined in Sandwich ELISA by first coating plate with 0.01% OVA in PBS, followed by loading diluted serum samples and then the secondary biotin-labeled anti-IgE antibody (BD).

Example 13

In Vitro Restimulation of Bronchial Lymph Node Cells and Cytokine Production

One day or three days after aerosol challenge, bronchial lymph nodes were harvested and single cell suspensions were prepared. Cells were seeded into round-bottom 96-well plates at $1 \times 10^6$ cells/well and cultured with 100 μg/ml ovalbumin for 4 days. Then supernatants were collected for cytokine ELISA assays as described.

Example 14

Cytotoxicity Assay

Serially diluted soluble mTL1A supernatants harvested from P815-TL1A transfected cells were added to $^{51}$Cr-labeled P815-TNFR25 transfected target cells. To test for TL1A blocking activity different anti-TL1A monoclonal antibodies were added into the culture and Cr release determined after 4 hours in triplicate samples. Spontaneous release was calculated from the wells that contained only $^{51}$Cr-labeled target cells. 100% release (positive control) was calculated from the wells that contained 51Cr-labeled target cells and 1% SDS. The percentage of cytotoxicity activity was calculated as the following: (mean readout of sample—mean readout of spontaneous release)/mean readout of positive control. Similar data were also obtained with EL4-transfectants.

Example 15

Blocking of Lung Inflammation by Antagonistic Anti-mTL1A Antibody

Mice were sensitized intraperitoneally with ovalbumin in alum on day 0 and day 5 followed by aerosol challenge with 0.5% ovalbumin in PBS for one hour on day 12. Mice were given L4G6 or an equivalent amount of the control hamster IgG (Jackson Immuno Research) by intraperitoneal injection of 50 μg/mouse each day from day 11 to 14. Allergic lung inflammation was evaluated on day 15.

Example 16

Adoptive Transfer of NKT Cells

Jα18 k.o. mice (Cui, J. et al. Science 278, 1623-6 (1997)) were a gift from Michael Lotze (U. Pittsburgh) with kind permission from M. Taniguchi (Ciba University, Japan). NKT cells from w.t. and DN TNFR25-tg mice were isolated from pooled spleen cells from 10 mice by positive selection using the EasySep mouse Pan NK Positive Selection Kit (StemCell Technologies, Vancouver, Canada) according to the manufacturer's instructions.

Example 17

Statistical Analyses

Statistical analyses using a two-tailed Student's t test were performed with the GraphPad Prism Software (San Diego, Calif.); p<0.05 is considered significant. Data in the text are presented as the mean±SEM.

Example 18

Generation of DR3 and TL1A Antibodies

A DR3-Ig fusion protein was generated, purified and used to immunize hamsters. Hybridoma supernatants were obtained and screened by ELISA using the DR3-Ig fusion protein as a screening agent. The nature of the hybridomas was verified by flow cytometry of DR3 transfected tumor cells, by Western blots, and by functional studies. All of the antibodies detected full-length and alternatively spliced DR3 on transfected cells by FACS, one of the antibodies detected DR3 in Western blots, and the antibody (4C12) displayed agonistic activity, mediating DR3 signaling in the absence of TL1A.

TL1A monoclonal antibodies were obtained by immunizing hamsters with a TL1A-maltose-binding-protein fusion. The TL antibodies detected transfected TL1A by flow cytometry. The antibody (L4G6) displayed antagonistic activity, blocking TL1A binding to DR3.

Example 19

Signaling Through TNFR25 Enhances CD8 Cross-Priming

Figure 12:
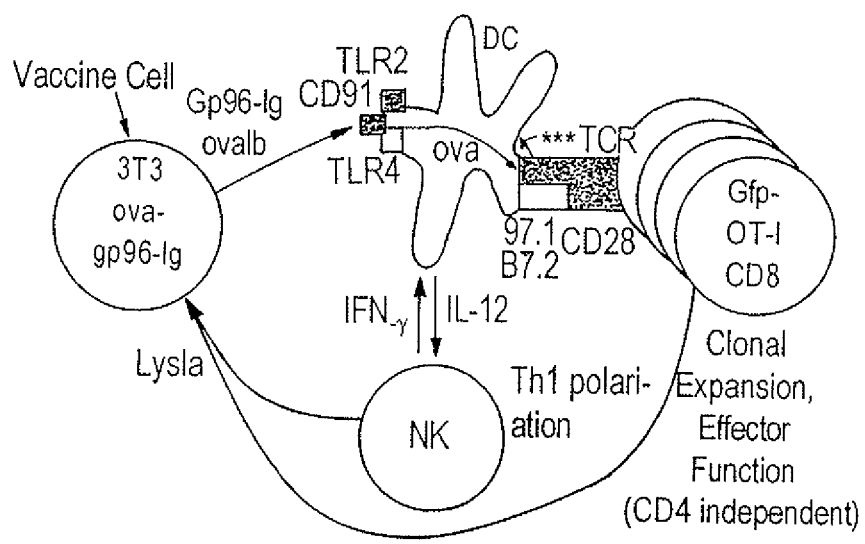
FIG. 12 depicts cross priming of CD8 cells by heat shock protein gp96. Vaccine cells (allogeneic or syngeneic) were transfected with gp96-Ig and ovalbumin whereupon they secreted gp96-Ig chaperoning ovalbumin peptides. Gp96 was detected by CD91 and TLR2/4 on DC resulting in their activation and engulfment of gp96_ig with its bound peptides. Activated DC up-regulate B7 (independent of CD4O-L) and cross-resent gp96-bound peptides via Kb (in B6 mice). OT-I are gfp expressing, TCR transgenic CD8 cells adoptively transferred to B6 mice specific for Kb-ova. Their expansion can be easily measured by green fluorescent protein.

A novel heat shock protein gp96 based system that mediates strong, antigen specific CD8-CTL expansion in vivo was recently described in Strbo et al., Am J Reprod Immunol. 2002 October; 48(4):220-5. In this model system released gp96-Ig (engineered to be secreted) activates dendritic cells and provides chaperoned peptides for cross presentation to and cross priming of CD8 cells (FIG. 12). The system is very useful because it is independent of CD4 help. Secreted gp96 provides the activation signal for DC through CD91 and TLR2/4 which is otherwise provided by CD40-L on CD4 cells. Accordingly, CD8 (OT-I) expansion in this system works well in CD40-L deficient mice. This has been employed to study mucosal immunity and to determine the role of TNFR25 in CD8 expansion.

EG7-gp96 is a cell line derived from the EL4 lymphoma by transfection with ovalbumin and gp96-Ig. The cells secrete gp96-Ig associated with ovalbumin peptides. Ovalbumin-peptides chaperoned by gp96-Ig enhance cross-priming of CD8 cells (FIG. 10) by about 10,000 fold when compared to ovalbumin alone. 10 Ong ova-gp96-Ig expand OT-I in B6 mice from a frequency of 0.5% among CD8 cells post transfer to 20% in the spleen after EG7-gp96-Ig immunization.

In order to determine the effect of TNFR25 signals on CD8 expansion TCR transgenic OT-I model as described above, were used together with EG7-gp96-Ig mediated stimulation. To determine the effect of TNFR25 signals the mice received an agonistic anti TNFR25 antibody (4C12), a TNFR25 binding but not agonistic antibody (L4G6) or a control IgG 24 h and 72 h after of EG7-gp96-Ig immunization. OT-I expansion was monitored in the peritoneal cavity on day 5 after immunization. 4C12 caused a increased recruitment of cells into the peritoneal cavity by EG7-gp96-Ig resulting in a doubling of the cell number. In addition 4C12 specifically caused an over 8-fold increase in the expansion of OT-I. The L4G6 anti TNFR25 antibody did not induce increased recruitment of cells to the peritoneal cavity and inhibited OT-I expansion.

These data show that agonistic anti TNFR25 antibodies costimulate CD8 cells and/or inhibit suppressive effects of Tregs via TNFR25. Costimulation of naïve T cells by TNFR25 results in increased proliferation and Th2 polarization upon secondary activation. In addition signaling of TNFR25 on T regulatory cells results in their temporary inhibition of suppression. The combined effect then is responsible for the increased CD8 expansion and cell recruitment seen in FIG. 11.

Example 20

CD4+CD25+ T Regulatory Cells Express High Levels on TNFR25

Figure 13:
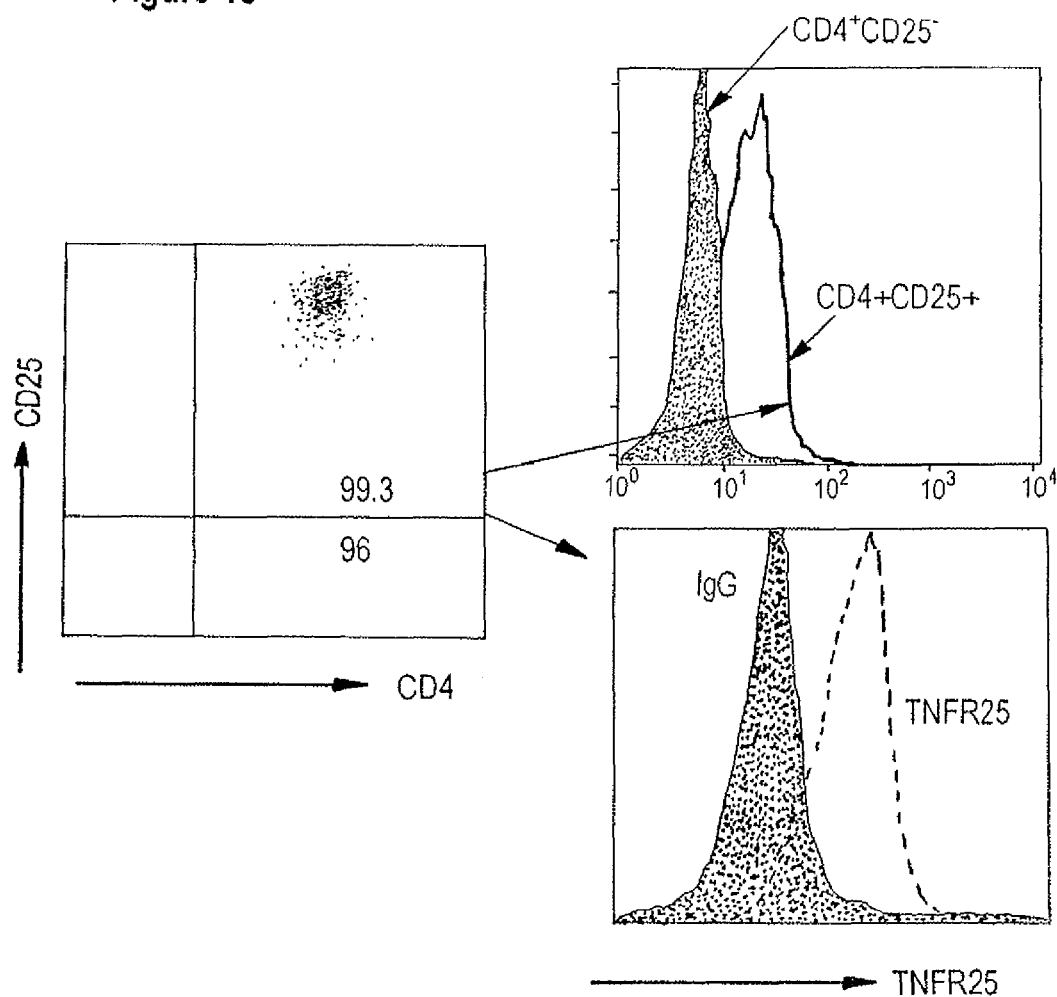
FIG. 13 depicts FoxP3 positive CD4+CD25+ Tregs expressing TNFR25. CD4 cells were purified by depleting B cells CD8 cells and monocytes and then positively selected by magnetic sorting for CD25 and then activated.

In order to determine the expression of TNFR25 CD4+ CD25 Tregs were purified from spleens by negative selection of CD4 cells followed magnetic sorting with anti CD25. The cells were cultured with anti CD3, anti CD28 beads at a bead to cell ratio of 3:1 and 2000 u/ml human IL-2 was added. Under these conditions the cells will begin to proliferate after 3-4 days and keep expanding for about 3 weeks. The cultured cells were analyzed by FACS analysis for CD4 and CD25, by intracellular cytofluorimetry for FoxP3 expression and for surface analysis of TNFR25. FIG. 13 shows that Tregs obtained in this way are essentially pure and express both FoxP3 and TNFR25.

Example 21

TNFR25-Blockade Causes Lethality of Dextran Sodium Sulfate Colitis

Figure 14:
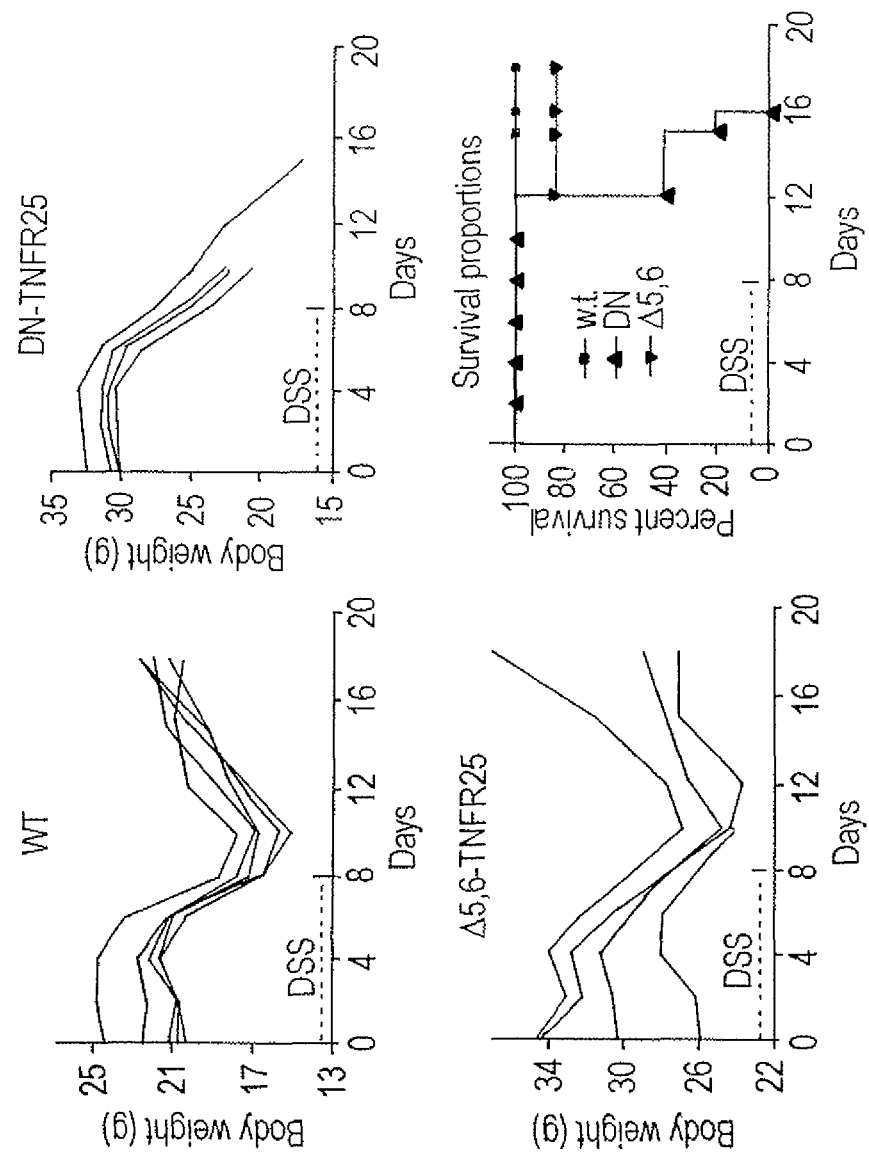
FIG. 14 depicts a lack of recovery of DN-TNFR25-tg mice from DSS induced colitis. 5 mice in each group received 2% DSS in drinking water for 8 days and were then restored to normal water.

The dextran sodium sulfate (DSS) model has widely been used as a colitis model resembling in some aspects Crohn's disease. The initial insult is the damaging effect of DSS on the permeability barrier normally provided by the gut epithelium. This effect of DSS allows access of the normal gut flora to sites in the mucosal immune system that set off an inflammatory immunological reaction resembling Crohn's colitis. Wild type (w.t.) 136 mice during an 8 day course of exposure to drinking water containing 2% DSS develop diarrhea and loose weight. Upon restoration of normal water, B6 mice recover and regain their normal weight. TNFR25 also influences the course of disease in Colitis. In the present experiment, w.t. and transgenic were exposed to mice to 2% DSS water for seven days. As shown in FIG. 14, DN-TNFR25-tg mice developed disease similar to wild type mice, however when normal water was restored, DN-TNFR25-tg mice did not recover as w.t. mice did. Instead DN-TNFR25-tg mice continued to loose weight and died between day 12 and 16. The Δ5,6-TNFR25-tg mice resembled w.t. mice although the death of one mouse could also suggest a disturbed immune response. Two conclusions were reached: In DNTNFR25-tg mice, the ensuing immune response is much stronger than in w.t. mice leading to lethality and the restoration of normal health and homeostasis in w.t. mice is dependent on normally functioning T regulatory (Treg) cells. Treg function is disturbed in DNTNFR25-tg mice. The latter is likely since it is known that Treg function is extraordinarily important to maintain homeostasis in the mucosal immune system by maintaining the correct balance between tolerance to nutrients and normal gut flora and immune response to gut pathogens.

Example 22

Immunization with EG7-gp96-Ig Induced the OT-I Cells to Migrate to Mucosal Sites Peyer's Patches, Lamina Propria Lymphocytes (LPL) and Intraepithelial Lymphocytes (IEL)

Figure 16:
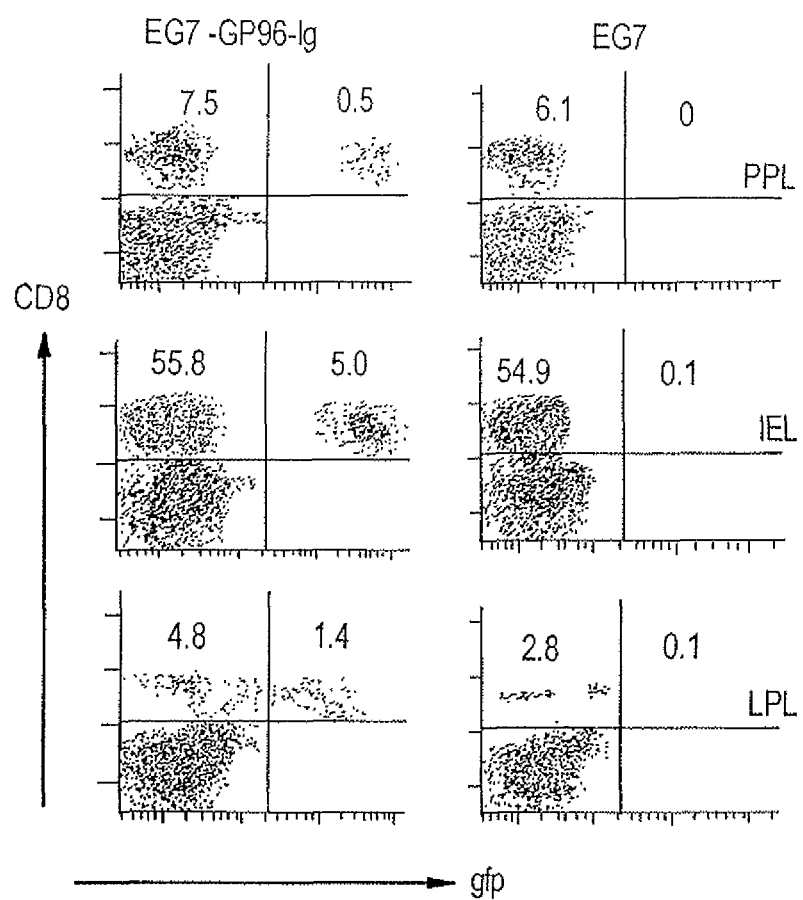
FIG. 16 shows Gfp-OT-I locating to the mucosa after gp96-Ig immunization i.p. Mice received 1 million gfp-OT-I i.v. by adoptive transfer. After 2 days the mice received 4 million EG7-gp96-Ig (left) or 4 million EG7 (right panels) i.p. as stimulus. Four days later the frequency of gfp-OT-I was analyzed in IEL, Peyer's patches and LPL in addition to the usual analysis of cells in the PEC, in the spleen and in lymph nodes.

As shown in FIG. 16 (right column), EG7-cells are unable to cause clonal expansion of OT-I or migration to mucosal sites. EG7-cells secreting gp96-Ig on the other hand cause clonal expansion of OT-I in spleen, lymph nodes and peritoneal cavity (not shown) and their migration to mucosal sites (FIG. 16). In Peyer's patches 8% of the cells are CD8+ and 6.7% of the CD8-cells are OT-I; in IEL 61% of the cells are CD8+ and 9% of the CD8 are OT-I. In LPL 29% of the CD8 cells are OT-I. The OT-I cells migrating to IEL after immunization are αEb7+ and α4β7+ but remain CD8αβ and TCRαβ, unlike resident CD8 IEL the majority of which are CD8αα and 50% TCRγδ.

In this disclosure there are described only the preferred embodiments of the invention and but a few examples of its versatility. It is to be understood that the invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this invention.

What is claimed is:

1. A method for enhancing expansion of antigen-specific CD8 T cells in a subject, the method comprising the steps of:
   (a) administering to the subject (i) an antigenic composition comprising a cell expressing a cognate antigen of the antigen specific CD8 T cells, wherein the cognate antigen is a non-self antigen; and (ii) an immunostimulatory agent, wherein the immunostimulatory agent enhances the subject's immune response to the antigenic composition; and
   wherein administration of (i) and (ii) is effective for inducing expansion of the antigen-specific CD8 T cells in the subject; and
   (b) administering to the subject an agonistic anti-TNFR25 antibody which specifically binds TNFR25 in an amount effective enhance the expansion of the antigen-specific CD8 T cells induced in step (a).

2. The method of claim 1, wherein the cell is allogeneic to the subject.

3. The method of claim 1, wherein the cell is a cancer cell.

4. The method of claim 1, wherein the non-self antigen is derived from a pathogen.

5. The method of claim 1, wherein the non-self antigen is an alloantigen.

6. The method of claim 1, wherein the non-self antigen is derived from a tumor cell.

7. The method of claim 3, wherein the non-self antigen is derived from a tumor cell.

8. The method of claim 1, wherein the immunostimulatory agent is an adjuvant.

9. The method of claim 1, wherein the antigenic composition in step (a)(i) comprises the immunostimulatory agent in step (a)(ii).

10. The method of claim 9, wherein the immunostimulatory agent is a heatshock protein engineered to be secreted.

11. The method of claim 1, wherein the antibody is 4C12.

12. The method of claim 1, wherein the antibody is a functional equivalent of 4C12.

13. The method of claim 1, wherein the method further comprises inhibiting the suppressive effects of T regulatory cells.

14. The method of claim 1, wherein the method further comprises depleting the subject of T regulatory cells.

15. The method of claim 1, wherein the immunostimulatory agent enhances the subject's immune response to the antigen by increasing T cell activity, or by downregulating suppressor cell activity, or both.

* * * * *

```
                         SEQUENCE LISTING

<160> NUMBER OF SEQ ID NOS: 16

<210> SEQ ID NO 1
<211> LENGTH: 1665
<212> TYPE: DNA
<213> ORGANISM: Mouse

<400> SEQUENCE: 1
gggagttgtt ctggatggcg cggggcggg cgggcagcag ctactctagt ctaggaacat      60
aggggctgag ctggttgggg aagccccggg ttacgcgacc gaccagagcc gcactcacaa    120
gggcccaggc ggtacacacc gcaatggagg cacggctgct gcggggctgc gtggtggagc    180
ctctgttcct accactgctg ctgctgctgc tgctgctgct gctgcttggt ggccagggcc    240
agggcggcat gtctggcagg tgtgactgtg ccagtgagtc ccagaagagg tatggcccgt    300
tttgttgcag gggctgccca aagggacact acatgaaggc cccctgcgca gaaccctgtg    360
gcaactccac ctgccttccc tgtccctcgg acacttctt gaccagagac aaccacttta    420
agactgactg tacccgctgc caagtctgtg atgaagaggc ccttcaagtg acccttgaga    480
actgctcggc aaagtcggac acccactgtg gctgccagtc aggctggtgt gttgactgct    540
ccaccgtgcc atgtgggaaa agctcacctt tctcttgtgt cccatgcggg gctacgacac    600
cagtccatga ggctccaacc ccccggccct gcctgcctgg cttctatata cgtggcaatg    660
actgcacgtc ctgccccacg ggcttcagca gcgtttgccc taaggcttgc actgctgtct    720
gtggctggaa gcagatgttt tgggtccagg tgcttctagg agtcgcgttc cttttttgggg    780 ctatcctgat ctgtgcatat tgtcgatggc agccttgtaa ggccgtggtc actgcagaca    840
cagctgggac ggagcccctg gcctcaccac agactgccca tctctcagcc tcagacagcg    900
cccacaccct cttggcacct ccaagcagta ctgggaaaat ctgtaccact gtccagttgg    960
taggcaacaa ctggacccct ggcttatccc agactcagga ggtggtctgc ggacaggcct   1020
cacaaccctg ggatcagctg ccaaacagaa ctcttggaac tcctctggca tctccgctct   1080
cgccagcgcc ccctgcgggc tctccggctg ctgtgctcca gcctggcccg cagctctacg   1140
atgtgatgga tgcggtccca gcacgaaggt ggaaggagtt cgtgcgcacg ctgggctgc    1200 gggaagcgga aattgaagcc gtggaggtgg aaatctgccg cttccgagac cagcagtatg   1260
agatgctcaa gcgctggcgt cagcagcagc ctgcaggcct cggtgccatc tatgcggctc   1320
tggagcgcaa gggtctggaa ggctgtgccg aggacctgcg cagccgcctg cagcgtggcc   1380
```

```
cgtgatggaa ggtccatcat ccactttgac accctagtga cccttgaagg agccttaagt      1440
attgttactt atgcgtgtag acattttatg tcaattacta accccctgcc gtggtcctgc      1500
gtagcagggc tggctgcctc acttttgctt atctgcagca cggagctcct gctaagggaa      1560
gcgtcatgga gaaataccag aaggggccaa gtgattggtt gctcagctgt taattagccc      1620
gagtttggac ttggtattaa atttcataag aaaagcagct gcttg                      1665

<210> SEQ ID NO 2
<211> LENGTH: 1665
<212> TYPE: DNA
<213> ORGANISM: Homo sapiens

<400> SEQUENCE: 2
cgggccctgc gggcgcgggg ctgaaggcgg aaccacgacg ggcagagagc acggagccgg        60
gaagcccctg ggcgcccgtc ggagggctat ggagcagcgg ccgcggggct gcgcggcggt       120
ggcggcggcg ctcctcctgg tgctgctggg ggcccgggcc cagggcggca ctcgtagccc       180
caggtgtgac tgtgccggtg acttccacaa gaagattggt ctgttttgtt gcagaggctg       240
cccagcgggg cactacctga aggccccttg cacggagccc tgcggcaact ccacctgcct       300
tgtgtgtccc caagacacct tcttggcctg ggagaaccac cataattctg aatgtgcccg       360
ctgccaggcc tgtgatgagc aggcctccca ggtggcgctg agaactgtt cagcagtggc       420 cgacacccgc tgtggctgta agccaggctg gtttgtggag tgccaggtca gccaatgtgt       480
cagcagttca cccttctact gccaaccatg cctagactgc ggggccctgc accgccacac       540
acggctactc tgttcccgca gagatactga ctgtgggacc tgcctgcctg gcttctatga       600
acatggcgat ggctgcgtgt cctgccccac gccacccccg tcccttgcag gagcaccctg       660
gggagctgtc cagagcgctg tgccgctgtc tgtggctgga ggcagagtag gtgtgttctg       720
ggtccaggtg ctcctggctg gccttgtggt ccccctcctg cttggggcca ccctgaccta       780
cacataccgc cactgctggc ctcacaagcc cctggttact gcagatgaag ctgggatgga       840
ggctctgacc ccaccaccgg ccacccatct gtcaccttg gacagcgccc acacccttct       900
agcacctcct gacagcagtg agaagatctg caccgtccag ttggtgggta acagctggac       960
ccctggctac cccgagaccc aggaggcgct ctgcccgcag gtgacatggt cctgggacca      1020 gttgccagc agagctcttg gccccgctgc tgcgcccaca ctctcgccag agtccccagc      1080
cggctcgcca gccatgatgc tgcagccggg cccgcagctc tacgacgtga tggacgcggt      1140
cccagcgcgg cgctggaagg agttcgtgcg cacgctgggg ctgcgcgagg cagagatcga      1200
agccgtggag gtggagatcg gccgcttccg agaccagcag tacgagatgc tcaagcgctg      1260
gcgccagcag cagcccgcgg gcctcggagc cgtttacgcg ccctggagc gcatgggggct      1320 ggacggctgc gtggaagact tgcgcagccg cctgcagcgc ggcccgtgac acggcgccca      1380
cttgccacct aggcgctctg gtggcccttg cagaagccct aagtacggtt acttatgcgt      1440
gtagacattt tatgtcactt attaagccgc tggcacggcc ctgcgtagca gcaccagccg      1500
gccccacccc tgctcgcccc tatcgctcca gccaaggcga agaagcacga acgaatgtcg      1560 agaggggtg aagacatttc tcaacttctc ggccggagtt tggctgagat cgcggtatta      1620
aatctgtgaa agaaaacaaa acaaaacaaa aaaaaaaaa aaaaa                       1665

<210> SEQ ID NO 3
<211> LENGTH: 759
<212> TYPE: DNA
<213> ORGANISM: Mouse
```

<400> SEQUENCE: 3

```
atggcagagg agctgggggtt gggcttcgga gaaggagtcc cagtggaagt gctgccggaa    60
ggctgtagac acaggccaga ggccagggcc gggctagctg ccaggagcaa agcctgcctg   120
gctctcacct gctgcctgtt gtcatttccc atcctcgcag gacttagcac cctcctaatg   180
gctggccagc tccgggtccc cggaaaagac tgtatgcttc gggccataac agaagagaga   240
tctgagcctt caccacagca agtttactca cctcccagag gcaagccgag agcacacctg   300
acaattaaga acaaacccc agcaccacat ctgaaaaatc agctctctgc tctacactgg   360
gaacatgacc tagggatggc cttcaccaag aacgggatga agtacatcaa caaatccctg   420
gtgatcccag agtcaggaga ctatttcatc tactcccaga tcacattccg agggaccaca   480
tctgtgtgtg gtgacatcag tcgggggaga cgaccaaaca agccagactc catcactgtg   540
gtcatcacca aggtagcaga cagctaccct gagcctgccc gcctactaac agggtccaag   600
tctgtgtgtg aaataagcaa caactggttc cagtccctct accttggggc catgttctcc   660
ttggaagaag gggacagact aatggtaaac gtcagtgaca tctccttggt ggattacaca   720
aaagaagata aaactttctt tggagctttc ttgctataa                          759
```

<210> SEQ ID NO 4
<211> LENGTH: 657
<212> TYPE: DNA
<213> ORGANISM: Mouse

<400> SEQUENCE: 4

```
atggaggcac ggctgctgcg gggctgcgtg gtggagcctc tgttcctacc actgctgctg    60
ctgctgctgc tgctgctgct gcttggtggc cagggccagg gcggcatgtc tggcaggtgt   120
gactgtgcca gtgagtccca gaagaggtat ggcccgtttt gttgcagggg ctgcccaaag   180
ggacactaca tgaaggcccc ctgcgcagaa ccctgtggca actccacctg ccttccctgt   240
ccctcggaca ccttcttgac cagagacaac cactttaaga ctgactgtac ccgctgccaa   300
gtctgtgatg aagaggccct tcaagtgacc cttgagaact gctcggcaaa gtcggacacc   360
cactgtggct gccagtcagg ctggtgtgtt gactgctcca ccgtgccatg tgggaaaagc   420
tcacctttct cttgtgtccc atgcggggct acgacaccag tccatgaggc tccaaccccc   480
cggccctgcc tgcctggctt ctatatacgt ggcaatgact gcacgtcctg ccccacgggc   540
ttcagcagcg tttgccctaa ggcttgcact gctgtctgtg gctggaagca gatgttttgg   600
gtccaggtgc ttctaggagt cgcgttcctt tttggggcta tcctgatctg tgcatat      657
```

<210> SEQ ID NO 5
<211> LENGTH: 696
<212> TYPE: DNA
<213> ORGANISM: Homo sapiens

<400> SEQUENCE: 5

```
atggagcagc ggccgcgggg ctgcgcggcg gtggcggcgg cgctcctcct ggtgctgctg    60
ggggcccggg cccagggcgg cactcgtagc cccaggtgtg actgtgccgg tgacttccac   120
aagaagattg gtcgttttg ttgcagaggc tgcccagcgg ggcactacct gaaggcccct   180
tgcacggagc cctgcggcaa ctccacctgc cttgtgtgtc cccaagacac cttcttggcc   240
tgggagaacc accataattc tgaatgtgcc cgctgccagg cctgtgatga gcaggcctcc   300
caggtggcgc tggagaactg ttcagcagtg gccgacaccc gctgtggctg taagccaggc   360
```

```
tggtttgtgg agtgccaggt cagccaatgt gtcagcagtt caccctttcta ctgccaacca    420 tgcctagact gcggggccct gcaccgccac acacggctac tctgttcccg cagagatact    480
gactgtggga cctgcctgcc tggcttctat gaacatggcg atggctgcgt gtcctgcccc    540
acgccacccc cgtcccttgc aggagcaccc tggggagctg tccagagcgc tgtgccgctg    600
tctgtggctg gaggcagagt aggtgtgttc tgggtccagg tgctcctggc tggccttgtg    660 gtcccctcc tgcttggggc caccctgacc tacaca                                 696

<210> SEQ ID NO 6
<211> LENGTH: 633
<212> TYPE: DNA
<213> ORGANISM: Homo sapiens

<400> SEQUENCE: 6
atggagcagc ggccgcgggg ctgcgcggcg gtggcggcgg cgctcctcct ggtgctgctg     60
ggggcccggg cccagggcgg cactcgtagc cccaggtgtg actgtgccgg tgacttccac    120
aagaagattg gtctgttttg ttgcagaggc tgcccagcgg ggcactacct gaaggccct    180 tgcacggagc cctgcggcaa ctccacctgc cttgtgtgtc cccaagacac cttcttggcc    240
tgggagaacc accataattc tgaatgtgcc cgctgccagg cctgtgatga gcaggcctcc    300
caggtggcgc tggagaactg ttcagcagtg gccgacaccc gctgtggctg taagccaggc    360
tggtttgtgg agtgccaggt cagccaatgt gtcagcagtt caccctttcta ctgccaacca    420 tgcctagact gcggggccct gcaccgccac acacggctac tctgttcccg cagagatact    480
gactgtggga cctgcctgcc tggcttctat gaacatggcg atggctgcgt gtcctgcccc    540
acgccacccc cgtcccttgc aggagcaccc tggggagctg tccagagcgc tgtgccgctg    600
tctgtggctg gaggcagagt aggtgtgttc tgg                                  633

<210> SEQ ID NO 7
<211> LENGTH: 2016
<212> TYPE: DNA
<213> ORGANISM: Homo sapiens

<400> SEQUENCE: 7
gagagggaaa agggaaggag gagactgagt gattaagtca cccactgtga agagctggtc     60
ttctatttaa tgggggctct ctctgcccag gagtcagagg tgcctccagg agcagcagga    120
gcatggccga ggatctggga ctgagctttg ggaaacagc cagtgtggaa atgctgccag    180
agcacggcag ctgcaggccc aaggccagga gcagcagcgc acgctgggct ctcacctgct    240
gcctggtgtt gctccccttc cttgcaggac tcaccacata cctgcttgtc agccagctcc    300
gggcccaggg agaggcctgt gtgcagttcc aggctctaaa aggacaggag tttgcaccttt    360 cacatcagca agtttatgca cctcttagag cagacggaga taagccaagg gcacacctga    420
cagttgtgag acaaactccc acacagcact ttaaaaatca gttcccagct ctgcactggg    480
aacatgaact aggcctggcc ttcaccaaga accgaatgaa ctataccaac aaattcctgc    540
tgatcccaga gtcgggagac tacttcattt actcccaggt cacattccgt gggatgacct    600
ctgagtgcag tgaaatcaga caagcaggcc gaccaaacaa gccagactcc atcactgtgg    660
tcatcaccaa ggtaacagac agctaccctg agccaaccca gctcctcatg ggaccaagt    720 ctgtatgcga agtaggtagc aactggttcc agcccatcta cctcggagcc atgttctcct    780
tgcaagaagg ggacaagcta atggtgaacg tcagtgacat ctcttttggtg gattacacaa    840 aagaagataa aaccttcttt ggagccttct actatagga ggagagcaaa tatcattata    900
```

```
tgaaagtcct ctgccaccga gttcctaatt ttctttgttc aaatgtaatt ataaccaggg    960
gttttcttgg ggccgggagt aggggcatt ccacagggac aacggtttag ctatgaaatt   1020
tggggcccaa aatttcacac ttcatgtgcc ttactgatga gagtactaac tggaaaaggc   1080
tgaagagagc aaatatatta ttaagatggg ttggaggatt ggcgagtttc taaatattaa   1140
gacactgatc actaaatgaa tggatgatct actcgggtca ggattgaaag agaaatattt   1200
caacacctcc ctgctataca atggtcacca gtggtccagt tattgttcaa tttgatcata   1260
aatttgcttc aattcaggag ctttgaagga agtccaagga aagctctaga aacagtata    1320 aactttcaga ggcaaaatcc ttcaccaatt tttccacata ctttcatgcc ttgcctaaaa   1380
aaaatgaaaa gagagttggt atgtctcatg aatgttcaca cagaaggagt tggttttcat   1440
gtcatctaca gcatatgaga aaagctacct ttcttttgat tatgtacaca gatatctaaa   1500
taaggaagta tgagtttcac atgtatatca aaaatacaac agttgcttgt attcagtaga   1560
gttttcttgc ccacctattt tgtgctgggt tctaccttaa cccagaagac actatgaaaa   1620
acaagacaga ctccactcaa aatttatatg aacaccacta gatacttcct gatcaaacat   1680
cagtcaacat actctaaaga ataactccaa gtcttggcca ggcgcagtgg ctcacacctg   1740
taatcccaac actttgggag gccaaggtgg gtggatcatc taaggccggg agttcaagac   1800
cagcctgacc aacgtggaga aaccccatct ctactaaaaa tacaaaatta gccgggcgtg   1860
gtagcgcatg gctgtaatcc tggctactca ggaggccgag gcagaagaat tgcttgaact   1920
ggggaggcag aggttgcggt gagcccagat cgcgccattg cactccagcc tgggtaacaa   1980
gagcaaaact ctgtccaaaa aaaaaaaaaa aaaaaa                             2016
```

<210> SEQ ID NO 8
<211> LENGTH: 20
<212> TYPE: DNA
<213> ORGANISM: Artificial sequence
<220> FEATURE:
<223> OTHER INFORMATION: Chemically synsthesized

<400> SEQUENCE: 8
cagtgagtcc cagaagaggt                                                20

<210> SEQ ID NO 9
<211> LENGTH: 20
<212> TYPE: DNA
<213> ORGANISM: Artificial sequence
<220> FEATURE:
<223> OTHER INFORMATION: Chemically synthesized

<400> SEQUENCE: 9
ggatagcccc aaaaaggaac                                                20

<210> SEQ ID NO 10
<211> LENGTH: 20
<212> TYPE: DNA
<213> ORGANISM: Artificial sequence
<220> FEATURE:
<223> OTHER INFORMATION: Chemically synthesized

<400> SEQUENCE: 10
tcctttttgg ggctatcctg                                                20

<210> SEQ ID NO 11
<211> LENGTH: 20
<212> TYPE: DNA

<213> ORGANISM: Artificial sequence
<220> FEATURE:
<223> OTHER INFORMATION: Chemically synthesized

<400> SEQUENCE: 11
ggtatttctc catgacgctt                                                     20

<210> SEQ ID NO 12
<211> LENGTH: 20
<212> TYPE: DNA
<213> ORGANISM: Artificial sequence
<220> FEATURE:
<223> OTHER INFORMATION: Chemically synthesized

<400> SEQUENCE: 12
ttcacccttc tactgccaac                                                     20

<210> SEQ ID NO 13
<211> LENGTH: 20
<212> TYPE: DNA
<213> ORGANISM: Artificial sequence
<220> FEATURE:
<223> OTHER INFORMATION: Chemically synthesized

<400> SEQUENCE: 13
taaccagggg cttgtgaggc                                                     20

<210> SEQ ID NO 14
<211> LENGTH: 21
<212> TYPE: DNA
<213> ORGANISM: Artificial sequence
<220> FEATURE:
<223> OTHER INFORMATION: Chemically synthesized

<400> SEQUENCE: 14
cgctcttgct ctctgtgtat g                                                   21

<210> SEQ ID NO 15
<211> LENGTH: 19
<212> TYPE: DNA
<213> ORGANISM: Artificial sequence
<220> FEATURE:
<223> OTHER INFORMATION: Chemically synthesized

<400> SEQUENCE: 15
ctgccagccc tcttccatc                                                      19

<210> SEQ ID NO 16
<211> LENGTH: 702
<212> TYPE: DNA
<213> ORGANISM: Mouse

<400> SEQUENCE: 16
atggaggcac ggctgctgcg gggctgcgtg gtggagcctc tgttcctacc actgctgctg         60
ctgctgctgc tgctgcttgg tggccagggc cagggcggca tgtctggcag gtgtgactgt        120
gccagtgagt cccagaagag gtatggcccg ttttgttgca ggggctgccc aaagggacac        180
tacatgaagg cccctgcgc agaaccctgt ggcaactcca cctgccttcc ctgtccctcg         240
gacaccttct tgaccagaga caaccacttt aagactgact gtaccgctg ccaagtctgt        300 gatgaagagg cccttcaagt gacccttgag aactgctcgg caaagtcgga caccactgt        360 ggctgccagt caggctggtg tgttgactgc tccaccgagc catgtgggaa aagctcacct        420
ttctcttgtg tcccatgcgg ggctacaaca ccagtccatg aggctccaac ccccggccc         480

```
tgcctgcctg gcttctatat acgtggcaat gactgcacgt cctgccccac gggcttcagc    540
agcgtttgcc ctaaggcttg cactgctgtc tgtggctgga agcagatgtt ttgggtccag    600
gtgcttctag gagtcgcgtt ccttttgggg gctatcctga tctgtgcata tggctctgga    660
agcgggagcg tcgacgatct ttacgacgat gataaatagt aa                       702
```